(12) United States Patent
Ledbetter et al.

(10) Patent No.: US 11,980,466 B2
(45) Date of Patent: May 14, 2024

(54) NESTED AND PARALLEL FEEDBACK CONTROL LOOPS FOR ULTRA-FINE MEASUREMENTS OF MAGNETIC FIELDS FROM THE BRAIN USING A NEURAL DETECTION SYSTEM

(71) Applicant: HI LLC, Los Angeles, CA (US)

(72) Inventors: Micah Ledbetter, Sunnyvale, CA (US); Ricardo Jimenez-Martinez, Culver City, CA (US); Julian Kates-Harbeck, Marina Del Rey, CA (US); Benjamin Siepser, Los Angeles, CA (US); Benjamin Shapiro, Culver City, CA (US)

(73) Assignee: HI LLC, Los Angeles, CA (US)

( * ) Notice: Subject to any disclaimer, the term of this patent is extended or adjusted under 35 U.S.C. 154(b) by 616 days.

(21) Appl. No.: 17/160,109

(22) Filed: Jan. 27, 2021

(65) Prior Publication Data

US 2021/0244329 A1    Aug. 12, 2021

Related U.S. Application Data

(60) Provisional application No. 63/035,650, filed on Jun. 5, 2020, provisional application No. 62/975,693, filed on Feb. 12, 2020.

(51) Int. Cl.
*A61B 5/245* (2021.01)
*A61B 5/00* (2006.01)
(Continued)

(52) U.S. Cl.
CPC .............. *A61B 5/245* (2021.01); *A61B 5/248* (2021.01); *A61B 5/6803* (2013.01); *G01R 33/26* (2013.01); *A61B 2562/0223* (2013.01)

(58) Field of Classification Search
CPC ....... A61B 5/245; A61B 5/248; A61B 5/6803; A61B 5/7214; A61B 2562/0223; A61B 2562/046; G01R 33/26; G01N 24/006
See application file for complete search history.

(56) References Cited

U.S. PATENT DOCUMENTS 3,173,082 A   3/1965   Bell et al.
3,257,608 A   6/1966   Bell et al.
(Continued)

FOREIGN PATENT DOCUMENTS

EP   2738627 A3   6/2014
EP   2380029 B1   10/2015
(Continued)

OTHER PUBLICATIONS

Iivanainen, Joonas, et al. "On-scalp MEG system utilizing an actively shielded array of optically-pumped magnetometers." Neuroimage 194 (2019): 244-258. (Year: 2019).*

(Continued)

*Primary Examiner* — Sean D Mattson

(74) *Attorney, Agent, or Firm* — Michael J. Bolan; Vista IP Law Group, LLP

(57) ABSTRACT

An actuated magnetic field is generated at a plurality of distinct frequencies that at least partially cancels an outside magnetic field at the plurality of distinct frequencies, thereby yielding a total residual magnetic field. The total residual magnetic field is coarsely detected and a plurality of coarse error signals are respectively output. The total residual magnetic field is finely detected and a plurality of (Continued)

fine error signals are respectively output. The actuated magnetic field is controlled respectively at the plurality of distinct frequencies at least partially based on at least one of the plurality of coarse error signals, and finely controlled respectively at the plurality of distinct frequencies at least partially based on at least one of the plurality of fine error signals.

29 Claims, 13 Drawing Sheets

(51) Int. Cl.
    *A61B 5/248*     (2021.01)
    *G01R 33/26*     (2006.01)

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Challlout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keena et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okanden et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,256 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Komack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,371,764 B2 | 8/2019 | Morales et al. |
| 10,772,561 B2 | 9/2020 | Donaldson |
| 2002/0060635 A1* | 5/2002 | Gupta ............... H03M 1/14 341/133 |
| 2004/0232912 A1 | 11/2004 | Tsukmamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2009/0184709 A1* | 7/2009 | Kajola ............... G01R 33/025 324/244 |
| 2009/0318773 A1 | 12/2009 | Jung |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0197838 A1* | 8/2013 | Simola ............... A61B 5/055 702/65 |
| 2013/0265042 A1 | 10/2013 | Kawabata et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0219732 A1* | 8/2015 | Diamond ............ G01R 33/16 324/201 |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parasa et al. |
| 2017/0261564 A1 | 9/2017 | Gabrys et al. |
| 2017/0299662 A1* | 10/2017 | Nagasaka ........... G01R 33/035 |
| 2017/0331485 A1 | 11/2017 | Gobet et al. |
| 2017/0332933 A1 | 11/2017 | Krishnaswamy |
| 2017/0343617 A1 | 11/2017 | Manickman et al. |
| 2017/0343695 A1 | 11/2017 | Stetson et al. |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe |
| 2018/0313913 A1 | 11/2018 | DeNatale et al. |
| 2019/0391213 A1 | 12/2019 | Alford |
| 2020/0025844 A1 | 1/2020 | Alford et al. |
| 2020/0057115 A1 | 2/2020 | Jimenez-Martinez et al. |

(56) References Cited

U.S. PATENT DOCUMENTS

| | | |
|---|---|---|
| 2020/0057116 A1 | 2/2020 | Zorzos et al. |
| 2020/0072916 A1 | 3/2020 | Alford et al. |
| 2020/0088811 A1 | 3/2020 | Mohseni |

FOREIGN PATENT DOCUMENTS

| | | |
|---|---|---|
| EP | 3037836 B1 | 9/2017 |
| WO | 2005081794 | 9/2005 |
| WO | 2014031985 | 2/2014 |
| WO | 2017095998 | 6/2017 |

OTHER PUBLICATIONS

Holmes, Niall, et al. "Balanced, bi-planar magnetic field and field gradient coils for field compensation in wearable magnetoencephalography." Scientific reports 9.1 (2019): 14196. (Year: 2019).*

Matti S. Hämäläinen, "Magnetoencephalography: A Tool For Functional Brain Imaging", Brain Topography, vol. 5. No. 2. 1992; 8 pages.

Martin W. Hess and Peter Benner, "Fast Evaluation of Time-Harmonic Maxwell's Equations Using the Reduced Basis Method", IEEE Transactions on N. 1ICROWAVE Theory and Techniques, vol. 61, No. 6, Jun. 2013; 10 pages.

Dipankar Sarkar and N. J. Halas, "General vector basis function solution of Maxwell's equations", Physical Review E, vol. 56, No. I, Jul. 1997; 11 pages.

M. Ortner, A. Nehorai, and H. Preissl, "A spatial point process model for solving the MEG inverse problem". Washington University in St. Louis, St. Louis, Missouri, USA, University of Arkansas for Medical Sciences, Little Rock, Arkansas, USA, University of Tuebingen, Tuebingen, Germany; Elsevier; International Congress Series I300 (2007) 253-256; 4 pages.

Non-Final Office Action for U.S. Appl. No. 17/160,179 dated Dec. 5, 2022 38 pages.

Restriction Requirement for U.S. Appl. No. 17/160,152 dated Dec. 5, 2022 8 pages.

Kiwoong Kim, Samo Begus, Hui Xia, Seung-Kyun lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014. pdf.

Sheng, Dong & R. Perry, Abigail & Krzyzewski, Sean & Geller, Shawn & Kitching, John & Knappe, Svenja. (2017). A microfabricated optically-pumped magnatic gradiometer. Applied Physics Letters. 110. 10.1063/1.4974349.

Sheng, Dehong & Li, S & Dural, Nezih & Romalis, Michael. (2013). Subfemtotesla Scalar Atomic Magoetometoy Using Multipass Cells. Physical review letters. 110. 160802. 10.1103/PhysRevLett. 110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J. 2012. In situ triaxial magnetic field compensation for the spin-exchange-relaxation-free atomic magnetometer. Review of Scientific Instruments, 83(10), p. 103104.

Joan Lee, Hyun & Shim, Jeong & Moon, Han Seb & Kim, Kiwoong. (2014). Flat-response spin-exchange relaxation free atomic magnetometer under negative feedback. Optics Express. 22. 10.1364/0E.22.019887.

Griffith, Clark & Jimenez-Martinez, Ricardo & Shah, Vishal & Knappe, SvenJa & Kitching, John. (2009). Miniature atomic magnetometer integrated with flux concentrators. Applied Physics Letters—Appl Phys Lett. 94. 10.105311.2885711.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.3056152.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-X.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett. 109.263903.

Orang Alem, Rahul Mhaskar, Ricardo Jimenez-Martinez, Dong Sheng, John LeBlanc, Lutz Trahms, Tilmann Sander, John Kitching, and Svenja Knappe, "Magnetic field imaging with microfabricated optically-pumped magnetometers," Opt Express 25, 7849-7858 (2017).

Slocum et al., Self-Calibrating Vector Magnetometer for Space, https://esto.nasa.gov/conferences/estc-2002/Papers/B3P4(Slocum).pdf.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

R.E. Slocum & L.J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/A0.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

Larry J. Ryan, Robert E. Slocum, and Robert B. Steves, Miniature Vector Laser Magnetometer Measurements of Earth's Field, May 10, 2004, 4 pgs.

Lorenz, V.O., Dai, X., Green, H., Asnicar, T.R., & Cundiff, S.T. (2008). High-density, high temperature alkali vapor cell. Review of Scientific Instruments, 79(12), 4 pages. .

F. Jackson Kimball, D & Dudley, J & Li, Y & Thulasi, Swecha & Pustelny, Szymon & Budker, Dmitry & Zoloterev, Max. (2016). Magnetic shielding and exotic spin-dependent interactions. Physical Review D. 94. 10.1103/PhysRevD.94.082005.

Huang, Haichao, et al. "Single-beam three axis atomic magnetometer." Applied Physics Letters 109.6 (2016): 062404. (Year:2016).

Scott Jeffrey Seltzer: "Developments in Alkali-Metal Atomic Magnetometry", Nov. 2008 (Nov. 1, 2008 ), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Kitching, J., "Chip-scale atomic devices." Applied Physics Reviews, 5(3), 031302 (2018).

(56) References Cited

OTHER PUBLICATIONS

Hill, R.M., Boto, E., Rea, M., Holmes, N., Leggett, J., Coles, L.A., Papastavrou, M., Everton, S.K., Hunt, B.A.E., Sims, D. and Osborne J., "Multi-channel whole-head OPM-MEG: helmet design and a comparison with a conventional system." Neuroimage 219, 116995 (2020).
Griffith, W.C., Knappe, S. and Kitching, J., "Femtotesla atomic magnetometry in a microfabricated vapor cell." Optics express 18, (26), 27167-27172 (2010).
Boto, E., Holmes, N., Leggett, J., Roberts, G., Shah, V., Meyer, S.S., Muñoz, L.D., Mullinger, K.J., Tierney, T.M., Bestmann, S. and Barnes, G.R., "Moving magnetoencephalography towards real-world applications with a wearable system." Nature, 555(7698), 657-661 (2018).
Sander, T.H., Preusser, J., Mhaskar, R., Kitching, J., Trahms, L., and Knappe, S., "Magnetoencephalography with a chip-scale atomic magnetometer." Biomedical Optics Express 3, (5), 981-990 (2012).
Borna, A, Carter, T.R., Colombo, A.P., Jau, Y.Y., McKay, J., Weisend, M., Taulu, S., Stephen, J.M., and Schwindt, P.D., "Non-invasive functional-brain-imaging with an OPM-based magnetoencephalography system." Plos one 15 (1), (2020).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Dupont-Roc, J., Haroche, S. & Cohen-Tannoudji, C., "Detection of very weak magnetic fields (10-9 gauss) by Rb zero-field level crossing resonances", Phys. Lett. A 28, 638-639 (1969).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Kominis, I.K., Kornack, T.W., Allred, J.C. and Romalis, M.V., "A subfemtotesla multichannel atomic magnetometer." Nature, 422(6932), 596-599 (2003).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
de Cheveigne, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Tierney, T.M., Holmes, N., Mellor, S., Lopez, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Allred, J, C., Lyman, R. N., Kornack, T. W., & Romalis, M. V. (2002). High-sensitivity atomic magnetometer unaffected by spin-exchange relaxation. Physical review letters, 89(13), 130801.
Balabas et al. Polarized alkali vapor with minute-long transverse spin-relaxation time, Phys. Rev. Lett. 105, 070801—Published Aug. 12, 2010.
Barbieri, F., Trauchessec, V. Caruso, L. Trejo-Rosillo, J. Telenczuk, B. Paul E., . . . & Ouanounou, G. (2016). Local recording of biological magnetic fields using Giant Magneto Resistance-based micro-probes. Scientific reports, 6, 39330.
Dmitry Budker and Michael Romalis, "Optical Magnetometry," Nature Physics, 2008, https://arxiv.org/abs/physics/0611246v1.
Anthony P. Colombo, Tony R. Carter, Amir Barna, Yuan-Yu Jau, Cort N. Johnson, Amber L. Dagel, and Peter D. D. Schwindt, "Four-channel optically pumped atomic magnetometer for magnetoencephalography," Opt Express 24, 15403-15416(2016).
Dang, H.B. & Maloof, AC. & Romalis, Michael. (2009). Ultra-high sensitivity magnetic field and magnetization measurements with an atomic magnetometer. Applied Physics Letters. 97.10.1063/1. 3491215.
Donley, E.A. & Hodby, E & Hollberg, L & Kitching, J. (2007). Demonstration of high-performance compact magnetic shields for chip-scale atomic devices. The Review of scientific instruments. 78.083102.
Hamalainen, Matti & Ritta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2.413-497.
Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (1 O).ISSN 2331-7019.
Jimenez-Martinez, R., Griffith, W.C., Wang, Y.J., Knappe, S., Kitching, J., Smith, K, & Prouty, M.D. (2010). Sensitivity comparison of Mix and frequency-modulated bell-bloom Cs magnetometers in a microfabricated cell. IEEE Transactions on Instrumentation and Measurement, 59(2), 372-378.
Knappe, Svenja & Sander, Tilmann & Trahms, Lutz. (2012). Optically-Pumped Magnetometers for MEG. Magnetoencephalography: From Signals to Dynamic Cortical Networks. 993-999. 10.10071978-3-642-33045-2_ 49.
Korth, H., K. Strohbehn, F. Tejada, A.G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.
Lenz, J. and Edelstein, S., 2006. Magnetic sensors and their applications. IEEE Sensors journal, 6(3), pp. 631-649.
Li, S & Vachaspati, Pranjal & Sheng, Dehong & Dural, Nezih & Romalis, Michael. (2011 ). Optical rotation in excess of 100 rad generated by Rb vapor in a multipass cell. Phys. Rev. A. 84. 10.1103/PhysRevA.84.061403.

(56) References Cited

OTHER PUBLICATIONS

Maze, J. R., Stanwix, P. I., Hodges, J. S., Hong, S., Taylor, J.M., Cappellaro, P., . . . & Yacoby, A. (2008). Nanoscale magnetic sensing with an individual electronic spin in diamond. Nature, 455(7213), 644.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, s. J., and Romalis, M.V., "Unshielded three-axis vector operation of a spin-exchange-relaxation-free atomic magnetometer." Applied physics letters 85.20 (2004): 4804-4806.

\* cited by examiner

NESTED AND PARALLEL FEEDBACK CONTROL LOOPS FOR ULTRA-FINE MEASUREMENTS OF MAGNETIC FIELDS FROM THE BRAIN USING A NEURAL DETECTION SYSTEM

RELATED APPLICATION DATA

Pursuant to 35 U.S.C. § 119(e), this application claims the benefit of U.S. Provisional Patent Application 62/975,693, filed Feb. 12, 2020, and U.S. Provisional Patent Application 63/035,650, filed Jun. 5, 2020, which are expressly incorporated herein by reference.

FIELD OF THE INVENTION

The present inventions relate to methods and systems for non-invasive measurements from the human body, and in particular, methods and systems related to detecting physiological activity from the human brain, animal brain, and/or peripheral nerves.

BACKGROUND OF THE INVENTION

Measuring neural activity in the brain is useful for medical diagnostics, neuromodulation therapies, neuroengineering, and brain-computer interfacing. Conventional methods for measuring neural activity in the brain include X-Ray Computed Tomography (CT) scans, positron emission tomography (PET), functional magnetic resonance imaging (fMRI), or other methods that are large, expensive, require dedicated rooms in hospitals and clinics, and are not wearable or convenient to use.

In contrast to these techniques, one promising technique for measuring neural activity in the brain is magnetoencephalography (MEG), which is capable of non-invasively detecting neural activity in the brain without potentially harmful ionizing radiation, and without use of heavy or large equipment. Thus, MEG-based neural activity measurement systems can be scaled to wearable or portable form factors, which is especially important in brain-computer interface (BCI) applications that require subjects to interact freely within their environment. MEG operates under the principle that time-varying electrical current within activated neurons inherently generate magnetic signals in the form of a magnetic field that can be detected by very sensitive magnetometers located around the head.

Measuring the small magnetic fields emanating from the brain, and doing so non-invasively (without surgically penetrating the skin and bone of the head) and doing so with high spatial and temporal resolution, is difficult. The magnetic fields produced by the brain are small, and they are smaller still by the time they propagate out past the skull and the skin surface of the head. In comparison, the magnetic field emitted from various outside magnetic sources in the environment, including from global sources, such as the Earth's magnetic field, and from localized sources, such as electrical outlets and sockets, electrical wires or connections in the wall, and everyday electrical equipment in a home, office, or laboratory setting, far exceed the strength of the magnetic signals generated in the brain by many orders of magnitude, and has a distribution in space and time that is not known a-priori. Hence, it is a difficult challenge to extract the small desired signal from the brain, and to discriminate it from much larger unwanted magnetic field signals from the rest of the user's natural environment.

One type of system that can be used for MEG is a Superconductive Quantum Interference Device (SQUID), which is sensitive enough to measure magnetic fields as small as $5 \times 10^{-18}$ Tesla, which can be compared to magnetic fields resulting from physiological processes in animals, which may be in the range of $10^{-9}$ to $10^{-6}$ Tesla. However, SQUIDs rely on superconducting loops, and thus require cryogenic cooling, which may make it prohibitively costly and too large to be incorporated into a wearable or portable form factor. Thus, neural activity measurement systems that utilize SQUIDs may not be appropriate for BCI applications.

Optically pumped magnetometers (OPMs) have emerged as a viable and wearable alternative to cryogenic, superconducting, SQUID-based MEG systems, and have an advantage of obviating the need for cryogenic cooling, and as a result, may be flexibly placed on any part of the body, including around the head, which is especially important for BCI applications. Because cryogenic cooling is not required, OPMs may be placed within millimeters of the scalp, thereby enabling measurement of a larger signal from the brain (brain signals dissipate with distance), especially for sources of magnetic signals at shallow depths beneath the skull, as well as providing consistency across different head shapes and sizes.

OPMs optically pump a sample (usually a vapor formed of one of the alkali metals (e.g., rubidium, cesium, or potassium) due to their simple atomic structure, low melting point, and ease of pumping with readily available lasers) with circularly polarized light at a precisely defined frequency, thereby transferring polarized light to the vapor, and producing a large macroscopic polarization in the vapor in the direction of the light (i.e., the alkali metal atoms in the vapor will all have spins that are oriented in the direction of the light) that induces a magnetically sensitive state in the vapor. Once this magnetically sensitive state is established, polarized light is no longer transferred to the vapor, but instead, passes transparently through the vapor. In the presence of an ambient magnetic field, the spin orientation (or precession) of the alkali metal atoms in the optically pumped vapor will uniformly change, thereby disrupting the magnetically sensitive state, which is then subsequently reestablished by the transfer of the polarized light to the vapor. Because the transmission of light through the vapor varies as the spin precession of the alkali metal atoms in the vapor (and thus the magnetically sensitive state) changes in response to changes in the ambient magnetic field, the transmission of light (either the pumping light or a separate probe light) through the vapor represents a magnetic field-dependent signal (i.e., a MEG signal) that may be detected, thereby providing a measure of magnitude changes in the magnetic field.

To maintain the magnetically sensitive state of the vapor, it is important that spin relaxation due to spin exchange collisions be suppressed. In low magnetic fields (<10 nT), spin relaxation due to spin exchange collisions can be suppressed greatly, and thus, some OPMs are operated as zero-field magnetometers or Spin Exchange Relaxation Free (SERF) OPMs (referred to as "SERF OPMs"), thereby allowing for very high magnetometer sensitivities. Furthermore, because OPM measurements can be quite sensitive to low-frequency noise, the polarization of the vapor may be modulated to move the MEG signal away from the low-frequency end of the spectrum. SERF OPMs typically amplitude modulate the vapor polarization using magnetic coils that generate oscillating magnetic fields that vary at a frequency (e.g., 2000 Hz) much greater than the relaxation rate of the vapor (approximately 100 Hz). The amplitude modulated MEG signal can then be demodulated using lock-in detection to recover the MEG signal.

Although SERF OPMs allow for very high magnetometer sensitivities, they have a small dynamic range and bandwidth compared to SQUIDs, and can thus only operate in small magnetic fields (tens of nT, and often lower, to stay in the linear range of the OPMs). This becomes problematic when attempting to detect a very weak neural activity-induced magnetic field from the brain against an outside magnetic field.

For example, referring to FIG. 1, the magnitude of the magnetic field generated by a human brain (i.e., the MEG signal) may range from below 5 fT to just below 1 pT, while the magnitude of the outside magnetic field, including the Earth's magnetic field, may range from just above 5 μT to 100 μT. It should be appreciated that Earth's magnetic field covers a large range as it depends on the position of the Earth, as well as the materials of the surrounding environment where the magnetic field is measured. There are also magnetic fields from electrical power lines, everyday electric objects (microwaves, fridges, cell phones), and their interaction with magnetizable objects (metal chair legs, tables, metal posts, wall rebar, etc.). In the United States these magnetic fields appear at 60 Hz and its harmonics (120 Hz, 180 Hz, etc.) and can range in amplitude from about 500 nT to below 10 nT. In Europe electrical power is at 50 Hz, with harmonics at 100 Hz, 150 Hz, etc., and similar magnitudes.

The approximate operating range of a SERF OPM (i.e., the range in which the metallic alkali vapor resonates) extends from below 1 fT up to 200 nT. Outside of this range, the metallic alkali vapor in the OPM loses sensitivity to magnetic fields. In contrast, the approximate operating range of a less sensitive sensor, such as a flux gate magnetometer, extends from around 100 fT to close to 100 μT. Thus, in contrast to flux gate magnetometers, the limited dynamic range of a SERF OPM presents a challenge in measuring signals having a high dynamic range, e.g., approximately $2 \times 10^{10}$, which corresponds to the ratio of the lower range magnitude of the MEG signal (approximately 5 fT) to the higher range magnitude of the outside magnetic field (approximately 100 μT).

Thus, to take advantage of SERF OPMs for MEG, the outside magnetic field must be suppressed to near-zero. Otherwise, the SERF OPM cannot operate. One conventional technique for suppressing the outside magnetic field involves using large, immobile, and expensive magnetically shielded rooms to passively isolate the SERF OPMs from the sources of the outside magnetic field, effectively reducing the dynamic range requirements of the SERF OPMs used to measure the weak MEG signals. These shielded rooms, however, are generally not viable for the consumer market, especially with regard to BCI applications, where it desirable that the MEG-based neural activity measurement system be incorporated into a wearable or portable form factor. Thus, for BCI applications, SERF OPMs must be capable of operating in the ambient background magnetic field of the native environment, including the Earth's magnetic field and other local sources of magnetic fields.

Another technique for suppressing the outside magnetic field without using magnetically shielded rooms involves incorporating a direct broadband feedback control system to actively null the outside magnetic field at the SERF OPM. In this case, the system actuators attempt to cancel the entire bandwidth of the outside magnetic field by applying a noise-cancelling, broadband, magnetic field to the sensors. However, such feedback control for OPM systems has not been implemented in a wearable system.

There, thus, remains a need to provide means for more effectively suppressing an outside magnetic field in a wearable neural detection system.

SUMMARY OF THE INVENTION

In accordance with a first aspect of the present inventions, a system comprises at least one magnetic field actuator (e.g., three orthogonal magnetic field actuators) configured for generating an actuated magnetic field that at least partially cancels an outside magnetic field, thereby yielding a total residual magnetic field. In one embodiment, each of the magnetic field actuator(s) comprises a uniform magnetic field actuator.

The system further comprises a plurality of coarse magnetometers (e.g., flux gate magnetometers) respectively configured for coarsely detecting the total residual magnetic field and outputting a plurality of coarse error signals, and a plurality of fine magnetometers (e.g., optically pumped magnetometers (OPMs)) respectively configured for finely detecting the total residual magnetic field and outputting a plurality of fine error signals.

In one embodiment, the system further comprises a signal acquisition unit configured for being worn on a head of a user. The signal acquisition unit comprises a support structure, the magnetic field actuator(s) affixed to the support structure, the plurality of coarse magnetometers affixed to the support structure, and the plurality of fine magnetometers affixed to the support structure. For example, the plurality of coarse magnetometers may be affixed to an outside of the support structure, and the plurality of fine magnetometers may be affixed to an inside of the support structure. The signal acquisition unit may be configured for deriving a plurality of magnetoencephalography (MEG) signals respectively from the plurality of fine error signals. In this embodiment, the system may further comprise a signal processing unit configured for determining an existence of neural activity in the brain of the user based on the plurality of MEG signals.

The system further comprises a coarse feedback control loop configured for coarsely controlling the actuated magnetic field at least partially based on at least one of the plurality of coarse error signals respectively output by at least one of the plurality of coarse magnetometers, and a fine feedback control loop configured for finely controlling the actuated magnetic field at least partially based on at least one of the plurality of fine error signals respectively output by at least one of the plurality of fine magnetometers. In one embodiment, the system further comprises a processor containing the coarse feedback control loop and the fine feedback control loop. In another embodiment, the coarse feedback control loop is configured for estimating the total residual magnetic field at at least one of the plurality of fine magnetometers based on the coarse error signal(s). In this case, the coarse feedback control loop may be configured for coarsely controlling the actuated magnetic field at least partially based on the estimated total residual magnetic field at the fine magnetometer(s).

In an optional embodiment, the system further comprises a management control loop configured for managing the operation of the coarse feedback control loop and the operation of the fine feedback control loop.

For example, the management control loop may be configured for activating the fine feedback control loop after initiating activation of the coarse feedback control loop. The coarse feedback control loop may be configured for coarsely controlling the actuated magnetic field in a manner that suppresses the total residual magnetic field at the fine magnetometer(s) to a baseline level, such that the fine magnetometer(s) comes in-range. The management control loop may be further configured for activating the fine feedback control loop to finely control the actuated magnetic field in a manner that further suppresses the total residual magnetic field at the fine magnetometer(s) to a lower level.

As another example, the management control loop may be configured for determining whether each of the plurality of fine magnetometers is in-range (e.g., in a linear operating range) or out-of-range, and finely controlling the actuated magnetic field based on the in-range or out-of-range determination. Finely controlling the actuated magnetic field based on the in-range or out-of-range determination may comprise considering the fine error signals output by the fine magnetometers that come in-range and ignoring the fine error signals output by the fine magnetometers that go out-of-range.

As still another example, finely controlling the actuated magnetic field based on the in-range or out-of-range determination may comprise determining whether each fine magnetometer is in a linear operating range, in a non-linear operating range, or saturated, and assigning a weighting to each fine magnetometer based on the linear operating range, non-linear operating range, or saturated determination.

In accordance with a second aspect of the present inventions, a method comprises generating an actuated magnetic field that at least partially cancels an outside magnetic field, thereby yielding a total residual magnetic field. In one method, the actuated magnetic field is generated in three orthogonal directions. In another method, the actuated magnetic field is uniform.

The method further comprises coarsely detecting the total residual magnetic field and outputting a plurality of coarse error signals, and finely detecting the total residual magnetic field and outputting a plurality of fine error signals. One method further comprises deriving a plurality of magnetoencephalography (MEG) signals respectively from the plurality of fine error signals, and determining an existence of neural activity in the brain of a user based on the plurality of MEG signals.

The method further comprises coarsely controlling the actuated magnetic field at least partially based on at least one of the plurality of coarse error signals, and finely controlling the actuated magnetic field at least partially based on at least one of the plurality of fine error signals. One method further comprises estimating the total residual magnetic field at at least one detection location where the total residual magnetic field is finely detected based on the coarse error signal(s), and coarsely controlling the actuated magnetic field at least partially based on the estimated total residual magnetic field at the detection location(s).

Another method further comprises managing the coarse control of the actuated magnetic field and the fine control of the actuated magnetic field.

For example, managing the coarse control of the actuated magnetic field and the fine control of the actuated magnetic field may comprise activating the fine control of the actuated magnetic field after initiating the coarse control of the actuated magnetic field. In this example, the actuated magnetic field may be coarsely controlled in a manner that suppresses the total residual magnetic field at at least one detection location to a baseline level, such that the accuracy of at least one fine error signal increases, and the actuated magnetic field may be finely controlled in a manner that further suppresses the total residual magnetic field at the detection location(s) to a lower level, such that the accuracy of the fine error signal(s) further increases.

As another example, managing the coarse control of the actuated magnetic field and the fine control of the actuated magnetic field may comprise determining an accuracy of each of the plurality of fine error signals, and finely controlling the actuated magnetic field based on the accuracy determination. In this case, finely controlling the actuated magnetic field based on the accuracy determination may comprise comparing the determined accuracies of the plurality of fine error signals to a first accuracy threshold, and considering the fine error signals having accuracies that rise above the first accuracy threshold when finely controlling the actuated magnetic field. Controlling the actuated magnetic field based on the accuracy determination may comprise comparing the determined accuracies of the plurality of fine error signals to a second accuracy threshold, and ignoring the fine error signals having accuracies that drop below the first accuracy threshold when finely controlling the actuated magnetic field.

As still another example, finely controlling the actuated magnetic field based on the comparison may comprise assigning a weighting to each fine error signal based on the comparison.

In accordance with a third aspect of the present inventions, a system comprises at least one magnetic field actuator (e.g., three orthogonal magnetic field actuators) configured for generating an actuated magnetic field at a plurality of distinct frequencies (e.g., a frequency in the range of 0 Hz-5 Hz, and a plurality of harmonic frequencies (e.g., 60 Hz harmonic frequencies)) that at least partially cancels an outside magnetic field, thereby yielding a total residual magnetic field. In one embodiment, each of the magnetic field actuator(s) comprises a uniform magnetic field actuator.

The system further comprises a plurality of magnetometers respectively configured for detecting the total residual magnetic field and outputting a plurality of error signals. In one embodiment, the system further comprises a signal acquisition unit configured for being worn on a head of a user. The signal acquisition unit comprises a support structure, the magnetic field actuator(s) affixed to the support structure, and the plurality of magnetometers affixed to the support structure. The signal acquisition unit is configured for deriving a plurality of magnetoencephalography (MEG) signals respectively from the plurality of error signals. In this embodiment, the system may further comprise a signal processing unit configured for determining an existence of neural activity in the brain of the user based on the plurality of MEG signals.

The system further comprises a plurality of feedback control loops configured for controlling the actuated magnetic field respectively at the plurality of distinct frequencies at least partially based on at least one of the plurality of error signals respectively output by at least one of the plurality of magnetometers. In one embodiment, the system further comprises a processor containing the plurality of feedback control loops.

In another embodiment, the plurality of feedback control loops are respectively configured for extracting characteristics of a plurality of frequency components respectively corresponding to the plurality of distinct frequencies from each of the error signal(s), and generating a plurality of noise-cancelling drive signals at the plurality of distinct frequencies based on the extracted characteristics of the plurality of frequency components. In this case, the magnetic field actuator(s) may be configured for generating an actuated magnetic field at the plurality of distinct frequencies respectively in response to the noise-cancelling drive signals at the plurality of distinct frequencies.

The extracted characteristics may comprise an envelope amplitude and a phase, in which case, the plurality of feedback control loops may be configured for respectively generating a plurality of noise-cancelling control signals that respectively vary in accordance with the envelopes and phases of the plurality of frequency components extracted from the each error signal, and respectively generating the plurality of noise-cancelling drive signals based on the plurality of noise-cancelling control signals. The plurality of noise-cancelling drive signals may comprise generating a plurality of oscillation signals and respectively multiplying the plurality of oscillation signals and the plurality of noise-cancelling drive signals.

In accordance with a fourth aspect of the present inventions, a method comprises generating an actuated magnetic field at a plurality of distinct frequencies (e.g., a frequency in the range of 0 Hz-5 Hz, and a plurality of harmonic frequencies (e.g., 60 Hz harmonic frequencies)) that at least partially cancels an outside magnetic field at the plurality of distinct frequencies, thereby yielding a total residual magnetic field. In one method, the actuated magnetic field is generated in three orthogonal directions. In another method, the actuated magnetic field is uniform.

The method further comprises detecting the total residual magnetic field and outputting a plurality of error signals, and controlling the actuated magnetic field respectively at the plurality of distinct frequencies at least partially based on at least one of the plurality of error signals. One method further comprises deriving a plurality of magnetoencephalography (MEG) signals respectively from the plurality of fine error signals, and determining an existence of neural activity in the brain of a user based on the plurality of MEG signals.

One method further comprises extracting characteristics of a plurality of frequency components respectively corresponding to the plurality of distinct frequencies from each of the error signal(s), and generating a plurality of noise-cancelling drive signals at the plurality of distinct frequencies based on the extracted characteristics of the plurality of frequency components. In this case, the actuated magnetic field may be generated at the plurality of distinct frequencies respectively in response to the plurality of noise-cancelling drive signals at the plurality of distinct frequencies. The extracted characteristics may comprise an envelope amplitude and a phase, in which case, the method may further comprise generating a plurality of noise-cancelling control signals that respectively vary in accordance with envelopes and phases of the plurality of frequency components extracted from each error signal, and the plurality of noise-cancelling drive signals may be respectively generated based on the plurality of noise-cancelling control signals. Generating the plurality of noise-cancelling drive signals may comprise generating a plurality of oscillation signals and respectively multiplying the plurality of oscillation signals and the plurality of noise-cancelling drive signals.

In accordance with a fifth aspect of the present inventions, a system comprises at least one magnetic field actuator (e.g., three orthogonal magnetic field actuators) configured for generating an actuated magnetic field at a plurality of distinct frequencies (e.g., a frequency in the range of 0 Hz-5 Hz, and a plurality of harmonic frequencies (e.g., 60 Hz harmonic frequencies)) that at least partially cancels an outside magnetic field at the plurality of distinct frequencies, thereby yielding a total residual magnetic field. In one embodiment, each of the magnetic field actuator(s) comprises a uniform magnetic field actuator.

The system further comprises a plurality of coarse magnetometers (e.g., flux gate magnetometers) respectively configured for coarsely detecting the total residual magnetic field and outputting a plurality of coarse error signals, and a plurality of fine magnetometers (e.g., optically pumped magnetometers (OPMs)) respectively configured for finely detecting the total residual magnetic field and outputting a plurality of fine error signals.

In one embodiment, the system further comprises a signal acquisition unit configured for being worn on a head of a user. The signal acquisition unit comprises a support structure, the magnetic field actuator(s) affixed to the support structure, the plurality of coarse magnetometers affixed to the support structure, and the plurality of fine magnetometers affixed to the support structure. For example, the plurality of coarse magnetometers may be affixed to an outside of the support structure, and the plurality of fine magnetometers may be affixed to an inside of the support structure. The signal acquisition unit may be configured for deriving a plurality of magnetoencephalography (MEG) signals respectively from the plurality of fine error signals. In this embodiment, the system may further comprise a signal processing unit configured for determining an existence of neural activity in the brain of the user based on the plurality of MEG signals.

The system further comprises a plurality of coarse feedback control loops configured for coarsely controlling the actuated magnetic field respectively at the plurality of distinct frequencies at least partially based on at least one of the plurality of coarse error signals respectively output by at least one of the plurality of coarse magnetometers, and a plurality of fine feedback control loops configured for finely controlling the actuated magnetic field respectively at the plurality of distinct frequencies at least partially based on at least one of the plurality of fine error signals respectively output by at least one of the plurality of fine magnetometers. In one embodiment, the system further comprises a processor containing the plurality of coarse feedback control loops and the plurality of fine feedback control loops. In another embodiment, the plurality of coarse feedback control loops are configured for estimating the total residual magnetic field respectively at the plurality of distinct frequencies at at least one of the plurality of fine magnetometers based on the coarse error signal(s). In this case, the plurality of coarse feedback control loops may be configured for coarsely controlling the actuated magnetic field respectively at the plurality of distinct frequencies at least partially based on the estimated total residual magnetic field at the fine magnetometer(s).

In an optional embodiment, the system further comprises a management control loop configured for managing the operation of the plurality of coarse feedback control loops and the operation of the plurality of fine feedback control loops.

For example, the management control loop may be configured for activating the plurality of fine feedback control loops after initiating activation of the plurality of coarse feedback control loops. The plurality of coarse feedback control loops may be configured for coarsely controlling the actuated magnetic field respectively at the plurality of distinct frequencies in a manner that suppresses the total residual magnetic field at the plurality of distinct frequencies at the fine magnetometer(s) to a baseline level, such that the fine magnetometer(s) comes in-range. The management control loop may be further configured for activating the plurality of fine feedback control loop to finely control the actuated magnetic field respectively at the plurality of distinct frequencies in a manner that further suppresses the total residual magnetic field at the plurality of distinct frequencies at the fine magnetometer(s) to a lower level.

As another example, the management control loop may be configured for determining whether each of the plurality of fine magnetometers is in-range (e.g., in a linear operating range) or out-of-range, and finely controlling the actuated magnetic field based on the in-range or out-of-range determination. Finely controlling the actuated magnetic field based on the in-range or out-of-range determination may comprise considering the fine error signals output by the fine magnetometers that come in-range and ignoring the fine error signals output by the fine magnetometers that go out-of-range.

As still another example, finely controlling the actuated magnetic field based on the in-range or out-of-range determination may comprise determining whether each fine magnetometer is in a linear operating range, in a non-linear operating range, or saturated, and assigning a weighting to each fine magnetometer based on the linear operating range, non-linear operating range, or saturated determination.

In another embodiment, the plurality of coarse feedback control loops and the plurality of fine feedback control loops are respectively configured for extracting characteristics of a plurality of frequency components respectively corresponding to the plurality of distinct frequencies from each of the error signal(s), and generating a plurality of noise-cancelling drive signals at the plurality of distinct frequencies based on the extracted characteristics of the plurality of frequency components. In this case, the magnetic field actuator(s) may be configured for generating an actuated magnetic field at the plurality of distinct frequencies respectively in response to the noise-cancelling drive signals at the plurality of distinct frequencies.

The extracted characteristics may comprise an envelope amplitude and a phase, in which case, the plurality of coarse feedback control loops and plurality of fine feedback control loops may be configured for respectively generating a plurality of noise-cancelling control signals that respectively vary in accordance with the envelopes and phases of the plurality of frequency components extracted from the each error signal, and respectively generating the plurality of noise-cancelling drive signals based on the plurality of noise-cancelling control signals. The plurality of noise-cancelling drive signals may comprise generating a plurality of oscillation signals and respectively multiplying the plurality of oscillation signals and the plurality of noise-cancelling drive signals.

In accordance with a sixth aspect of the present inventions, a method comprises generating an actuated magnetic field at a plurality of distinct frequencies (e.g., a frequency in the range of 0 Hz-5 Hz, and a plurality of harmonic frequencies (e.g., 60 Hz harmonic frequencies)) that at least partially cancels an outside magnetic field at the plurality of distinct frequencies, thereby yielding a total residual magnetic field. In one method, the actuated magnetic field is generated in three orthogonal directions. In another method, the actuated magnetic field is uniform.

The method further comprises coarsely detecting the total residual magnetic field and outputting a plurality of coarse error signals, and finely detecting the total residual magnetic field and outputting a plurality of fine error signals. One method further comprises deriving a plurality of magnetoencephalography (MEG) signals respectively from the plurality of fine error signals, and determining an existence of neural activity in the brain of a user based on the plurality of MEG signals.

The method comprises coarsely controlling the actuated magnetic field respectively at the plurality of distinct frequencies at least partially based on at least one of the plurality of coarse error signals, and finely controlling the actuated magnetic field respectively at the plurality of distinct frequencies at least partially based on at least one of the plurality of fine error signals. One method further comprises estimating the total residual magnetic field respectively at the plurality of distinct frequencies at at least one detection location where the total residual magnetic field is finely detected based on the coarse error signal(s), and coarsely controlling the actuated magnetic field respectively at the plurality of distinct frequencies at least partially based on the estimated total residual magnetic field at the detection location(s).

Another method further comprises managing the coarse control of the actuated magnetic field and the fine control of the actuated magnetic field.

For example, managing the coarse control of the actuated magnetic field and the fine control of the actuated magnetic field may comprise activating the fine control of the actuated magnetic field after initiating the coarse control of the actuated magnetic field. In this example, the actuated magnetic field may be coarsely controlled in a manner that suppresses the total residual magnetic field at at least one detection location to a baseline level, such that the accuracy of at least one fine error signal increases, and the actuated magnetic field may be finely controlled in a manner that further suppresses the total residual magnetic field at the detection location(s) to a lower level, such that the accuracy of the fine error signal(s) further increases.

As another example, managing the coarse control of the actuated magnetic field and the fine control of the actuated magnetic field may comprise determining an accuracy of each of the plurality of fine error signals, and finely controlling the actuated magnetic field based on the accuracy determination. In this case, finely controlling the actuated magnetic field based on the accuracy determination may comprise comparing the determined accuracies of the plurality of fine error signals to a first accuracy threshold, and considering the fine error signals having accuracies that rise above the first accuracy threshold when finely controlling the actuated magnetic field. Controlling the actuated magnetic field based on the accuracy determination may comprise comparing the determined accuracies of the plurality of fine error signals to a second accuracy threshold, and ignoring the fine error signals having accuracies that drop below the first accuracy threshold when finely controlling the actuated magnetic field.

As still another example, finely controlling the actuated magnetic field based on the comparison may comprise assigning a weighting to each fine error signal based on the comparison.

Still another method further comprises extracting characteristics of a plurality of frequency components respectively corresponding to the plurality of distinct frequencies from each of the coarse error signal(s), extracting characteristics of a plurality of frequency components respectively corresponding to the plurality of distinct frequencies from each of the fine error signal(s), and generating a plurality of noise-cancelling drive signals at the plurality of distinct frequencies based on the extracted characteristics of the plurality of frequency components from each of the coarse error signal(s) and the extracted characteristics of the plurality of frequency components from each of the fine error signal(s). In this case, the actuated magnetic field may be generated at the plurality of distinct frequencies respectively in response to the plurality of noise-cancelling drive signals at the plurality of distinct frequencies.

The extracted characteristics may comprise an envelope amplitude and a phase, in which case, the method may further comprise generating a plurality of noise-cancelling control signals that respectively vary in accordance with envelopes and phases of the plurality of frequency components extracted from each coarse error signal and the each fine error signal, and the plurality of noise-cancelling drive signals may be respectively generated based on the plurality of noise-cancelling control signals. Generating the plurality of noise-cancelling drive signals may comprise generating a plurality of oscillation signals and respectively multiplying the plurality of oscillation signals and the plurality of noise-cancelling drive signals.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the present inventions and are not therefore to be considered limiting of its scope, the present inventions will be described and explained with additional specificity and detail through the use of the accompanying drawings in which.

DETAILED DESCRIPTION OF THE EMBODIMENTS

Significantly, the neural activity measurement systems (and variations thereof) described herein are configured for non-invasively acquiring magnetoencephalography (MEG) signals from a brain of a user while effectively suppressing the outside magnetic field without the use of magnetically shielded rooms, and identifying and localizing the neural activity within the cortical structures of the brain of the user based on the acquired magnetoencephalography (MEG) signals.

The neural activity measurement system described herein may take the form of a brain computer interface (BCI) (also known as a neural-controlled interface (NCI), mind-machine interface (MMI), direct neural interface (DNI), or brain-machine interface (BMI)), which converts the neural activity information into commands that are output to an external device or devices for carrying out desired actions that replace, restore, enhance, supplement, or improve natural central nervous system (CNS) output, and thereby changes the ongoing interactions between the CNS of a user and an external or internal environment.

Figure 1:
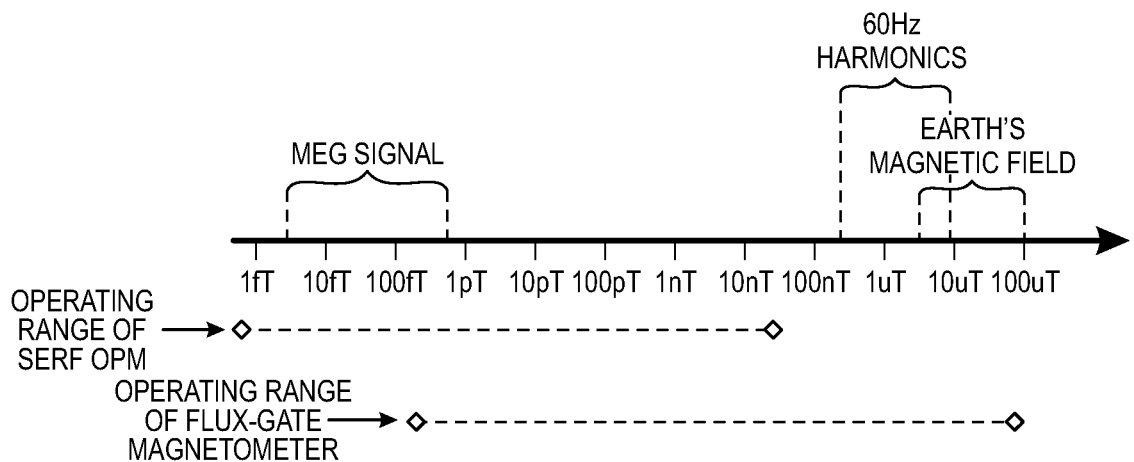
FIG. 1 is a diagram of illustrating dynamic ranges of a magnetoencephalography (MEG) signal and a typical outside magnetic field, and the operating ranges of a Spin Exchange Relaxation Free (SERF) optically-pumped magnetometer (OPM) and flux gate magnetometer, plotted on a magnetic spectrum.
Figure 2:
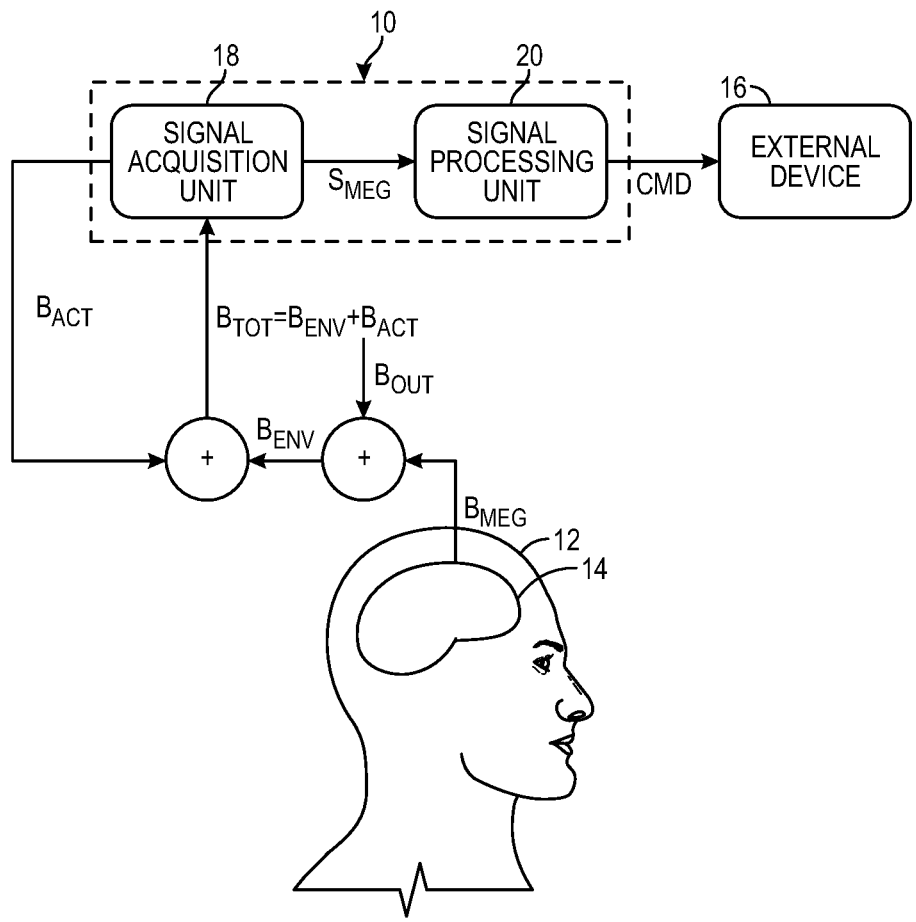
FIG. 2 is a block diagram of a neural activity measurement system constructed in accordance with one embodiment of the present inventions, particularly shown in the context of a brain computer interface (BCI)

For example, as illustrated in FIG. 2, one embodiment of a neural activity measurement system 10 constructed in accordance with the present inventions will be described. The neural activity measurement system 10 is configured for measuring neural activity in the brain 14 of a user 12, generating commands CMD in response to the measured neural activity information, and sending the commands CMD to an external device 16 in the context of a BCI.

To this end, the neural activity measurement system 10 generally comprises a signal acquisition unit 18 configured for at least partially cancelling a relatively strong outside magnetic field $B_{OUT}$ within an environmental magnetic field $B_{ENV}$ that also includes a relatively weak MEG magnetic field $B_{MEG}$ induced by electrical current (indicative of neural activity) in a brain 14 of a user 12. That is, $B_{TOT}=B_{ENV}+B_{ACT}=B_{OUT}+B_{MEG}+B_{ACT}$. The outside magnetic field $B_{OUT}$ may emanate from global sources (e.g., the Earth's magnetic field), and from localized sources, including, but not limited to, from electromagnetic radiation emanating from electrical outlets and sockets, electrical wires or connections in the wall, and everyday electrical equipment (microwave ovens, televisions, refrigerators, environmental systems (air conditioning, etc.) in a home, office, or laboratory setting, as well as from cell phones, biomagnetics unrelated to neural signals (such as facial muscles, magnetic fields produced by the heart or nerves firing), everyday objects encountered inside (metal and magnetic objects, including steel supports, rebar, studs, utility boxes, etc.,) and outside spaces, such as cell phone towers, power lines, transformers, and moving vehicles (e.g., cars, trains, bikes, electric bikes and scooters, electric cars, etc.), user motion/rotation/translation in a background field (earth field), user clothing and eyeglasses, personal electronics (e.g., laptop computers, watches, phones, smart rings, etc.), active implantable medical devices (pacemakers), augmented reality/virtual reality, sound systems (that use magnets), etc.

The signal acquisition unit 18 is configured for generating an actuated magnetic field $B_{ACT}$ that at least partially cancels the relative strong outside magnetic field $B_{OUT}$ within the environmental magnetic field $B_{ENV}$, yielding a total residual magnetic field $B_{TOT}$ (which is preferably zero or near-zero due to the summation of the environmental magnetic field $B_{ENV}$ and the actuated magnetic field $B_{ACT}$). The signal acquisition unit 18 is further configured for detecting the total residual magnetic field $B_{TOT}$ as feedback to cancel the outside magnetic field $B_{OUT}$, and ultimately, to suppress the total residual magnetic field $B_{TOT}$. The signal acquisition unit 18 is also configured for extracting and outputting a clean (i.e., reduced-noise) electrical MEG signals $S_{MEG}$ of the MEG magnetic field $B_{MEG}$ from the total residual magnetic field $B_{TOT}$.

The signal acquisition unit 18 may utilize any suitable technique for acquiring the MEG magnetic field $B_{MEG}$, including, but not limited to the techniques described in U.S. patent application Ser. No. 16,428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(s)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Application Ser. No. 62/858,636, entitled "Integrated Magnetometer Arrays for Magnetoencephalography (MEG) Detection Systems and Methods," U.S. Provisional Application Ser. No. 62/836,421, entitled "Systems and Methods for Suppression of Non-Neural Interferences in Magnetoencephalography (MEG) Measurements," U.S. Provisional Application Ser. No. 62/842,818 entitled "Active Shield Arrays for Magnetoencephalography (MEG)," U.S. Provisional Application Ser. No. 62/926,032 entitled "Systems and Methods for Multiplexed or Interleaved Operation of Magnetometers," U.S. Provisional Application Ser. No. 62/896,929 entitled "Systems and Methods having an Optical Magnetometer Array with Beam Splitters," and U.S. Provisional Application Ser. No. 62/960,548 entitled "Methods and Systems for Fast Field Zeroing for Magnetoencephalography (MEG)," which are all expressly incorporated herein by reference.

The neural activity measurement system 10 further comprises a signal processing unit 20 configured for processing the electrical MEG signal $S_{MEG}$ to identify and localize neural activity within the cortex of the brain 14 of the user 12, and issuing the commands CMD to the external device 16 in response to the identified and localized neural activity in the brain 14 of the user 12.

It should be appreciated that, although the neural activity measurement system 10 is described herein in the context of a BCI, the present inventions should not be so limited, and may be applied to any system used for any application (including, but not limited to, medical, entertainment, neuromodulation stimulation, lie detection devices, alarm, educational, etc.), where it is desirable to perform measurements on a magnetic field induced by any physiological process in a person that would benefit from canceling an outside magnetic field. For example, instead of deriving neural activity information from MEG signals, magnetic fields induced by electrical heart activity can be measured to determine heart activity information of a person.

Figure 3:
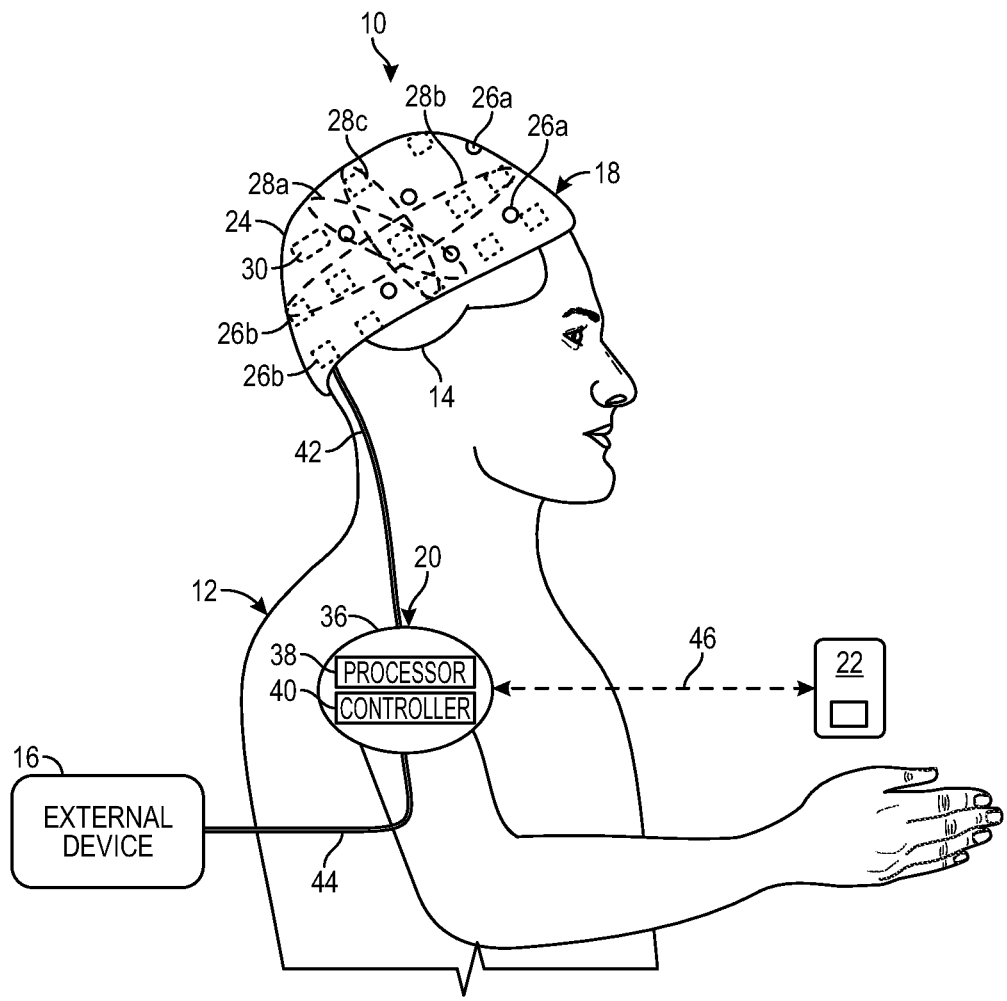
FIG. 3 is a side view of a physical implementation of the BCI of FIG. 2.

Referring now to FIG. 3, an exemplary physical implementation of the neural activity measurement system 10 will be described.

As shown, the signal acquisition unit 18 is configured for being applied to the user 12, and in this case, worn on the head of the user 12. The signal acquisition unit 18 comprises a support structure 24, a plurality of magnetometers 26 (divided between a plurality of coarse magnetometers 26a and a plurality of fine magnetometers 26b) distributed about the support structure 24, a set of magnetic field actuators 28 in proximity to the fine magnetometers 26b, and a processor 30 electrically coupled between the magnetometers 26 and the set of actuators 28.

The support structure 24 may be shaped, e.g., have a banana, headband, cap, helmet, beanie, other hat shape, or other shape adjustable and conformable to the user's head, such that at least some of the magnetometers 26 are in close proximity, preferably in contact, with the outer skin of the head, and in this case, the scalp of the user 12. The support structure 24 may be made out of any suitable cloth, soft polymer, plastic, hard shell, and/or any other suitable material as may serve a particular implementation. An adhesive, strap, or belt (not shown) can be used to secure the support structure 24 to the head of the user 12.

Each of the magnetometers 26 is configured for detecting a spatial component of the total residual magnetic field $B_{TOT}$, and outputting a corresponding electrical signal representative of the spatial component of the total residual magnetic field $B_{TOT}$. In the illustrated embodiment, the plurality of coarse magnetometers 26a is distributed on the outside of the support structure 24 for detecting the respective spatial components of the total residual magnetic field $B_{TOT}$ mainly from outside of the support structure 24, whereas the plurality of fine magnetometers 26b is distributed on the inside of the support structure 24 for detecting the respective spatial components of the total residual magnetic field $B_{TOT}$ mainly from inside the support structure 24 (i.e. they are closer to the brain 14 of the user 12).

Each of the coarse magnetometers 26a has a relatively low sensitivity, but high dynamic sensitivity range, to magnetic fields, whereas each of the fine magnetometers 26b has a relatively high sensitivity, but low dynamic sensitivity range. The signal 10 acquisition unit 18 may have any suitable number of magnetometers 26. For example, the signal acquisition unit 18 may have twelve coarse magnetometers 26a and twenty-five fine magnetometers 26b, although one of ordinary skill in the art would understand that signal acquisition unit 18 may have any suitable number of coarse magnetometers 26a and magnetometers 26b, including more coarse magnetometers 26a than fine magnetometers 26b. In alternative embodiments of the signal acquisition unit 18, the plurality of magnetometers 26 may only comprise a plurality of fine magnetometers 26b distributed on the inside of the support structure 24.

As will be described in further detail below, the clean (i.e., reduced-noise) electrical MEG signals $S_{MEG}$ that are representative of the spatial components of the MEG magnetic field $B_{MEG}$, and that will be processed by the signal processing unit 20 for determining and localizing neural activity in the brain 14 of the user 12, will be respectively derived from the electrical signals output by the respective fine magnetometers 26b, and in some cases, from the electrical signals output by the coarse magnetometers 26a; whereas the characteristics (namely amplitude and phase) of the actuated magnetic field $B_{ACT}$ will be derived from the electrical signals output by the respective coarse magnetometers 26a and/or the electrical signals output by at least some of the respective fine magnetometers 26b.

The set of magnetic field actuators 28 is configured for generating the actuated magnetic field $B_{ACT}$ to at least partially cancel the outside magnetic field $B_{OUT}$ in the vicinity of the plurality of fine magnetometers 26b. The set of magnetic field actuators 28 may, e.g., comprise at least one coil (not shown in FIG. 3) and at least one driver (not shown in FIG. 3) that drives the coil(s) with electrical current at a defined amperage, voltage, or some other variable, and at a defined frequency, thereby setting the actuation strengths of the magnetic field actuators 28. In the illustrated embodiment, the set of magnetic field actuators 28 comprises three uniform magnetic field actuators 28a-28c for respectively generating x-, y-, and z-components of the actuated magnetic field $B_{ACT}$ to cancel the outside magnetic field $B_{OUT}$ in all three dimensions. In an optional embodiment, the set of magnetic field actuators 28 may also comprise six gradient magnetic field actuators (not shown) for generating first-order x-, y-, and z-gradient components of the actuated magnetic field $B_{ACT}$. One of ordinary skill in the art would appreciate that the set of field actuators 28 may include any suitable and type of magnetic field actuators capable of cancelling the outside magnetic field $B_{OUT}$ at the magnetometers 26.

The processor 30 is electrically coupled between the magnetometers 26 and magnetic field actuators 28 via electrical wires (not shown), and is configured for processing the electrical signals respectively output by the coarse magnetometers 26a (and in some cases the electrical signals output by the fine magnetometers 26b) in response to the detection of the spatial components of the total residual magnetic field $B_{TOT}$, determining the characteristics of the actuated magnetic field $B_{ACT}$ required to cancel the outside magnetic field $B_{OUT}$, and generating noise-cancelling control signals based on this determination that are output to the set of magnetic field actuators 28.

To minimize the size, weight, and cost of the signal acquisition unit 18, the functions of the processor 30 are preferably performed digitally (e.g., in firmware, such as a programmable logic device (e.g., a field programmable gate array (FPGA), or an ASIC (application specific integrated circuit) device, or in a micro-processor)), in which case, one or more analog-to-digital converters (not shown) can be employed between the magnetometers 26 and the processor 30, and one or more digital-to-analog converters (not shown) can be employed between the magnetic field actuators 28 and the processor 30. However, it should be appreciated that, in alternative embodiments, the functions of the processor 30 may be at least partially performed in an analog fashion.

It should be noted that, although the signal acquisition unit 18 is illustrated in FIG. 3 as having a single set of magnetic field actuators 28 and a single processor 30, the signal acquisition unit 18 may comprise more than one set of magnetic field actuators 28 and more than one processor 30. In this case, each set of magnetic field actuators 28 and each corresponding processor 30 may be associated with a subset of magnetometers 26. In one embodiment, the fine magnetometers 26b, set(s) of magnetic field actuators 28, and processor(s) 30 may be fabricated as integrated module(s). For example, each integrated module may comprise a rectangular substrate containing a subset or all of the fine magnetometers 26b, a set of the magnetic field actuators 28 incorporated into the rectangular substrate, such that coils of the magnetic field actuators 28 respectively wrap around the orthogonal dimensions of the rectangular substrate, and the processor 30 affixed to the surface of the rectangular substrate between the coils.

The signal processing unit 20 is configured for being applied to the user 12, and in this case, worn remotely from the head of the user 12, e.g., worn on the neck, shoulders, chest, or arm) of the user 12. The signal processing unit 20 comprises a housing 36 containing its own processor 38 and a controller 40. The processor 38 is configured for identifying and localizing neural activity within the cortex of the brain 14 of the user 12, and the controller 40 is configured for issuing commands CMD to an external device 16 in response to the identified and localized neural activity in the brain 14 of the user 12, as well as controlling the high-level operational functions of the signal acquisition unit 18. The signal processing unit 20 may additionally include a power supply (which if head-worn, may take the form of a rechargeable or non-chargeable battery), a control panel with input/output functions, a display, and memory. Alternatively, power may be provided to the signal processing unit 20 wirelessly (e.g., by induction).

In the illustrated embodiment, the neural activity measurement system 10 further comprises a wired connection 42 (e.g., electrical wires) for providing power from the signal processing unit 20 to the signal acquisition unit 18 and communicating between the signal processing unit 20 and the signal acquisition unit 18. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the signal acquisition unit 18 and/or communicating between the signal processing unit 20 and the signal acquisition unit 18.

In the illustrated embodiment, the neural activity measurement system 10 further comprises a wired connection 44 (e.g., electrical wires) for providing power from the signal processing unit 20 to the external device 16 and communicating between the signal processing unit 20 and the external device 16. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the external device 16 and/or communicating between the signal processing unit 20 and the external device 16.

The neural activity measurement system 10 may optionally comprise a remote processor 22 (e.g., a Smartphone, tablet computer, or the like) in communication with the signal processing unit 20 coupled via a wired connection (e.g., electrical wires) or a non-wired connection (e.g., wireless radio frequency (RF) signals (e.g., Bluetooth, Wifi, cellular, etc.) or optical links (e.g., fiber optic or infrared (IR)) 46. The remote processor 22 may store data from previous sessions, and include a display screen.

It should be appreciated that at least a portion of the signal acquisition and magnetic field cancellation functionality of the processor 30 in the signal acquisition unit 18 may be implemented in the signal processing unit 20, and/or at least a portion of the neural activity determination and localization functionality of the signal processing unit 20 may be implemented in the signal acquisition unit 18. In the preferred embodiment, the functionalities of the processor 30 in the signal acquisition unit 18, as well as the processor 38 and a controller 40 in the signal processing unit 20, may be implemented using one or more suitable computing devices or digital processors, including, but not limited to, a microcontroller, microprocessor, digital signal processor, graphical processing unit, central processing unit, application specific integrated circuit (ASIC), field programmable gate array (FPGA), and/or programmable logic unit (PLU). Such computing device(s) or digital processors may be associated with non-transitory computer- or processor-readable medium that stores executable logic or instructions and/or data or information, which when executed, perform the functions of these components. The non-transitory computer- or processor-readable medium may be formed as one or more registers, for example of a microprocessor, FPGA, or ASIC, or can be a type of computer-readable media, namely computer-readable storage media, which may include, but is not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Significantly, the signal acquisition unit 18 utilizes one or more novel techniques for cancelling the outside magnetic field $B_{OUT}$ in the detected total residual magnetic field $B_{TOT}$, such that the magnitude of the detected total residual magnetic field $B_{TOT}$ is at a level that allows the fine magnetometers 26b to be in-range.

Figure 4:
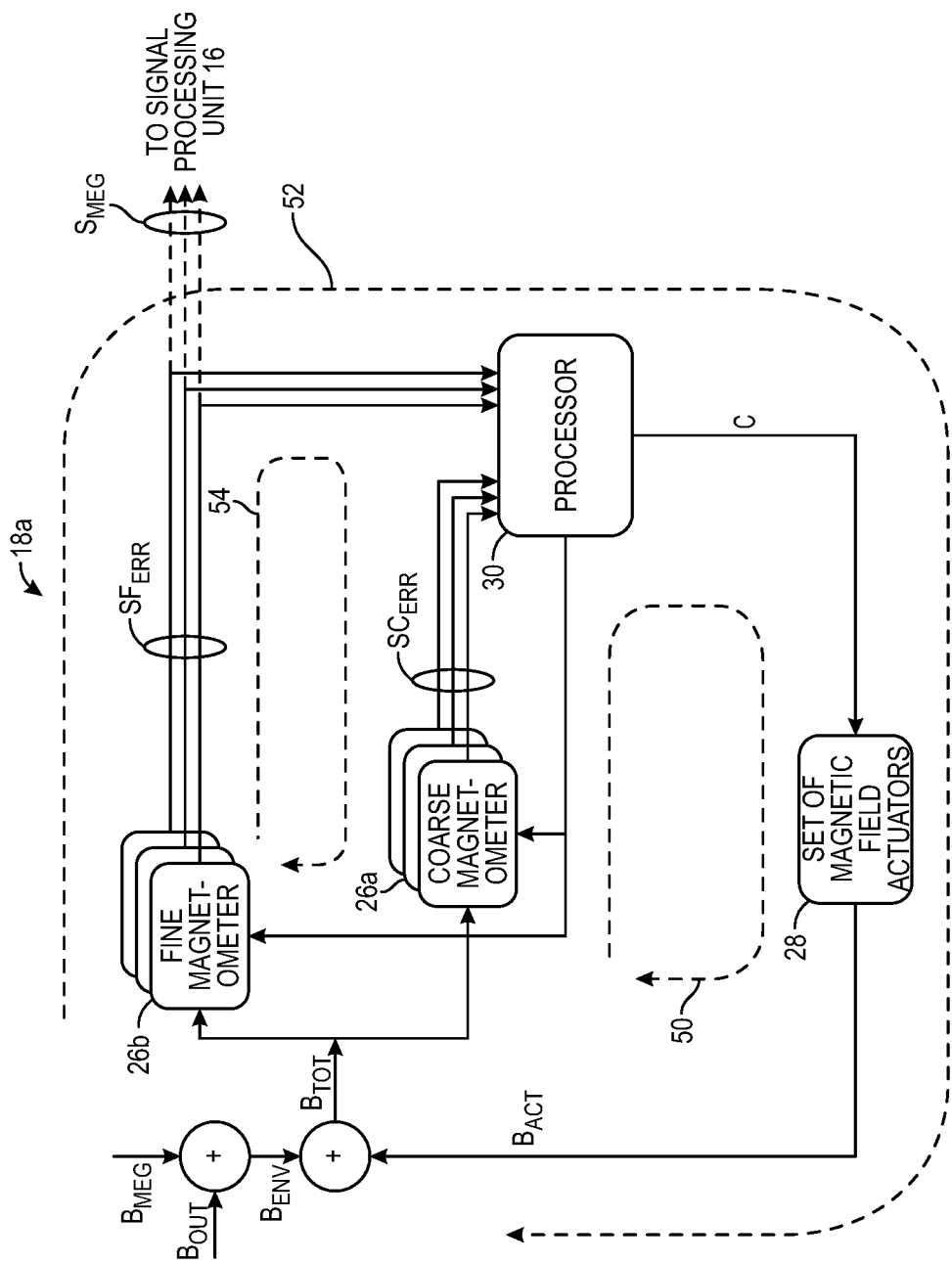
FIG. 4 is a block diagram of one exemplary embodiment of a signal acquisition unit used by the neural activity measurement system of FIG. 2.

As shown in FIG. 4, one embodiment of a signal acquisition unit 18a takes advantage of the high dynamic range of the coarse magnetometers 26a to compensate for the relatively low dynamic range of the fine magnetometers 26b to cancel the large outside magnetic field $B_{OUT}$, while also taking advantage of high sensitivity of the fine magnetometers 26b to compensate for the low sensitivity of the coarse magnetometers 26a to measure the MEG signal $S_{MEG}$.

In particular, the signal acquisition unit 18a is configured for at least partially cancelling the outside magnetic field $B_{OUT}$ at the locations of the fine magnetometers 26b by initially employing a coarse feedback control loop 50 having a relatively low sensitivity, but relatively high dynamic range, for coarsely cancelling the outside magnetic field $B_{OUT}$ (e.g., low-frequency cancellation of the outside magnetic field $B_{OUT}$ contributed by the Earth's magnetic field (e.g., any of the techniques described in U.S. patent application Ser. No. 16/752,393, entitled "Neural Feedback Loop Filters for Enhanced Dynamic Range Magnetoencephalography (MEG) Systems and Methods," which is expressly incorporated herein by reference, a broadband cancellation technique, and/or the harmonic frequency band cancellation techniques described below), such that the spatial components of the total residual magnetic field $B_{TOT}$ at the fine magnetometers 26b drop to a baseline level within the operating range of the fine magnetometers 26b, and subsequently employing a fine feedback control loop 52 having a relatively high sensitivity, but a low dynamic range that encompasses this baseline level for finely cancelling the outside magnetic field $B_{OUT}$ (e.g., low-frequency cancellation of the outside magnetic field $B_{OUT}$ contributed by the Earth's magnetic field, broadband cancellation, and/or the harmonic frequency band cancellation techniques described below), such that the spatial components of the total residual magnetic field $B_{TOT}$ at the fine magnetometers 26b further drop from the baseline level to an even lower level, which can make operation of the magnetometers 26 more reliable. The signal acquisition unit 18a is also configured for managing the coarse feedback control loop 50 and fine feedback control loop 52 by employing a management control loop 54.

In particular, the coarse feedback control loop 50 and fine feedback control loop 52 are implemented in the processor 30, with the coarse feedback control loop 50 coarsely controlling the set of magnetic field actuators 28 in response to input from the coarse magnetometers 26a, and the fine feedback control loop 52 finely controlling the set of magnetic field actuators 28 in response to input from the fine magnetometers 26b. Although the coarse feedback control loop 50 is illustrated as receiving input from three coarse magnetometers 26a, and the fine feedback control loop 52 is illustrated as receiving input from three fine magnetometers 26b, it should be appreciated that the coarse feedback control loop 50 can receive input from more or less coarse magnetometers 26a, including only one coarse magnetometer 26a, and the fine feedback control loop 52 can receive input from more or less fine magnetometers 26b, including only one fine magnetometer 26b. Furthermore, although the coarse feedback control loop 50 and fine feedback control loop 52 are illustrated as receiving input from an equal number of coarse magnetometers 26a and fine magnetometers 26b, the coarse feedback control loop 50 and fine feedback control loop 52 may receive input from an unequal number of coarse magnetometers 26a and fine magnetometers 26b, including a number of coarse magnetometers 26a that is greater or less the number of fine magnetometers 26b.

Initially, due to the relatively low dynamic range of the fine magnetometers 26b, the magnitude of the total residual magnetic field $B_{TOT}$ is too great for the fine magnetometers 26b to detect the total residual magnetic field $B_{TOT}$. However, due to the relatively high dynamic range of the coarse magnetometers 26a, the spatial components of the total residual magnetic field $B_{TOT}$ can be respectively detected by the coarse magnetometers 26a, which outputs coarse error signals $SC_{ERR}$ corresponding to the spatial components of the detected total residual magnetic field $B_{TOT}$.

When the magnitude of the total residual magnetic field $B_{TOT}$ is above the dynamic range of the fine magnetometers 26b, the processor 30 acquires the coarse error signals $SC_{ERR}$ output by the coarse magnetometers 26a in response to detecting the spatial components of the total residual magnetic field $B_{TOT}$, computes the characteristics (namely, the amplitude and phase) of the actuated magnetic field $B_{ACT}$ estimated to minimize the coarse error signals $SC_{ERR}$ output by the coarse magnetometers 26a, and generates a corresponding noise-cancelling control signal C for output to the set of magnetic field actuators 28 for at least partially cancelling the outside magnetic field $B_{OUT}$ at the fine magnetometers 26b, and ultimately suppressing the total residual magnetic field $B_{TOT}$ to a baseline level at the fine magnetometers 26b.

In one embodiment, the processor 30 may estimate the spatial components of the total residual magnetic field $B_{TOT}$ respectively at each fine magnetometer 26b based on the coarse error signals $SC_{ERR}$ output by the coarse magnetometers 26a or fine error signals $SF_{ERR}$ of other fine magnetometers 26b, e.g., using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", which is expressly incorporated herein by reference.

In the embodiment illustrated in FIG. 3, the set of magnetic field actuators 28 are spatially much closer to the fine magnetometers 26b (and, in fact, may be integrated with the fine magnetometers 26b as a single unit) than the coarse magnetometers 26a. Despite the fact that the coarse magnetometers 26a and fine magnetometers 26b may essentially experience the same outside magnetic field $B_{OUT}$, due to the spatial differences between coarse magnetometers 26a and fine magnetometers 26b relative to the proximate magnetic field actuators 28, the coarse magnetometers 26a will be affected by the actuated magnetic field $B_{ACT}$ generated by the magnetic field actuators 28 much less than the fine magnetometers 26b will be affected by the same actuated magnetic field $B_{ACT}$ (e.g., 20%).

Hence, in this example, ignoring the minute contribution of the MEG magnetic field $B_{MEG}$ for purposes of simplicity, the coarse magnetometers 26a and fine magnetometers 26b will measure a different total residual magnetic field $B_{TOT}=B_{OUT}+B_{ACT}$, because even though the outside magnetic field $B_{OUT}$ may be the same at both coarse magnetometers 26a and fine magnetometers 26b, the actuated magnetic field $B_{ACT}$ will differ between the coarse magnetometers 26a and fine magnetometers 26b based on their different proximities to the magnetic field actuators 28. Thus, absent estimation of the spatial components of the total residual magnetic field $B_{TOT}$ respectively at each fine magnetometer 26b, cancellation of the outside magnetic field $B_{OUT}$, and the resulting suppression of the total residual magnetic field $B_{TOT}$, at the fine magnetometers 26b based directly (i.e., without correction) on the coarse error signals $SC_{ERR}$ output by the coarse magnetometers 26a may be insufficient.

In accordance with the noise-cancelling control signal C output by the processor 30, the set of magnetic field actuators 28 generates the actuated magnetic field $B_{ACT}$, which combines with the outside magnetic field $B_{OUT}$ (along with weak MEG magnetic field $B_{MEG}$ from the brain 14) to create a total residual magnetic field $B_{TOT}$ at the fine magnetometers 26b having spatial components that are at baseline level within the operating range of the fine magnetometers 26b.

Once the spatial components of the total residual magnetic field $B_{TOT}$ are at the baseline level, they can be respectively detected by the fine magnetometers 26b, which outputs fine error signals $SF_{ERR}$ corresponding to the spatial components of the detected total residual magnetic field $B_{TOT}$. The processor 30 then acquires the fine error signals $SF_{ERR}$ output by the fine magnetometers 26b in response to detecting the spatial components of the total residual magnetic field $B_{TOT}$, computes the characteristics of the actuated magnetic field $B_{ACT}$ estimated to minimize the fine error signals $SF_{ERR}$ output by the fine magnetometers 26b, and generates a corresponding noise-cancelling control signal C for output to the set of magnetic field actuators 28 for at least partially cancelling the outside magnetic field $B_{OUT}$ at the fine magnetometers 26b, and ultimately suppressing the total residual magnetic field $B_{TOT}$ to a lower level than the baseline level at the fine magnetometers 26b.

In one embodiment, even when the spatial components of the total residual magnetic field $B_{TOT}$ are at the baseline level, and the fine error signals $SF_{ERR}$ output by the fine magnetometers 26b are being actively acquired, the processor 30 may be further configured for correcting or refining the fine error signals $SF_{ERR}$ using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", and/or U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which are expressly incorporated herein by reference.

In accordance with the noise-cancelling control signal C output by the processor 30, the set of magnetic field actuators 28 generates the actuated magnetic field $B_{ACT}$, which combines with the outside magnetic field $B_{OUT}$ (along with weak MEG magnetic field $B_{MEG}$ from the brain 14) to create a total residual magnetic field $B_{TOT}$ having spatial components at the fine magnetometers 26b that are at the baseline level. At this point, the fine error signals $SF_{ERR}$ can serve to collect MEG signals $S_{MEG}$ representative of the spatial components of the MEG magnetic field $B_{MEG}$ for further processing by the signal processing unit 20 to identify and localize neural activity in the brain 14 of the user 12.

It should be appreciated that, in the illustrated embodiment, the coarse magnetometers 26a and fine magnetometers 26b are capable of detecting the total residual magnetic field $B_{TOT}$ in three dimensions (x, y, and z), and the set of magnetic field actuators 28 includes three magnetic field actuators 28a-28c (shown in FIG. 2) capable of generating the actuated magnetic field $B_{ACT}$ in three dimensions (x, y, and z). As such, each of the coarse error signals $SC_{ERR}$ and fine error signals $SF_{ERR}$ respectively output by the coarse magnetometers 26a and fine magnetometers 26b to the processor 30, and the control signal C output by the processor 30 to the respective magnetic field actuators 28a-28c, is a vector (i.e., comprises an x-component, y-component, and z-component), such that the outside magnetic field $B_{OUT}$ can be cancelled, and thus the total residual magnetic field $B_{TOT}$ suppressed, in three dimensions.

In an alternative embodiment, the signal acquisition unit 18a (shown in FIG. 4) only employs the coarse feedback control loop 50 for at least partially cancelling the outside magnetic field $B_{OUT}$, such that the spatial components of the total residual magnetic field $B_{TOT}$ at the fine magnetometers 26b drop to a baseline level within the operating range of the fine magnetometers 26b. In this case, the signal acquisition unit 18a does not have a fine feedback control loop 52, and the processor 30 only uses the coarse error signals $SC_{ERR}$ output by the coarse magnetometers 26a to compute the characteristics of the actuated magnetic field $B_{ACT}$ estimated to suppress the total residual magnetic field $B_{TOT}$ to near-zero at the fine magnetometers 26b, even after the spatial components of the total residual magnetic field $B_{TOT}$ at the fine magnetometers 26b are already at the baseline level, such that the fine magnetometers 26b remain in an operating range.

Whether the signal acquisition unit 18a employs both the coarse feedback control loop 50 and the fine feedback control loop 52 to cancel the outside magnetic field $B_{OUT}$, or employs only the coarse feedback control loop 50 to cancel the outside magnetic field $B_{OUT}$, it can be appreciated that the signal acquisition unit 18a is capable of coarsely canceling a large portion of the outside magnetic field $B_{OUT}$, while still collecting signals from the fine magnetometers 26b sensitive enough to measure the weaker MEG magnetic field $B_{MEG}$ generated by the neural activity in the brain 14 of the user 12.

The processor 30 employs the management control loop 54 to manage how the coarse feedback control loop 50 and fine feedback control loop 52 are employed (e.g., how the coarse error signals $SC_{ERR}$ output by the coarse magnetometers 26a and the fine error signals $SF_{ERR}$ output by the fine magnetometers 26b are to be used) for optimal cancellation of the outside magnetic field $B_{OUT}$, and thus optimal suppression of the total residual magnetic field $B_{TOT}$, and corrects additional factors that can change more slowly over time, such as, e.g., calibrating the magnetometers 26 (e.g., using calibration techniques described in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference), and optimizing performance metrics in the signal acquisition unit 18, either globally or locally (e.g., using optimal control methods disclosed in U.S. Provisional Application Ser. No. 62/975,727, entitled "Optimal Methods to Feedback Control and Estimate Magnetic Fields to Enable a Wearable MEG System to Measure Magnetic Fields from the Brain", which is expressly incorporated herein by reference), adapting to changing time delays in computations, etc.

The management control loop 54 manages the coarse feedback control loop 50 and fine feedback control loop 52 based on whether the fine magnetometers 26b are in-range or out-of-range, e.g., by considering coarse error signals $SC_{ERR}$ from the coarse magnetometers 26a and ignoring fine error signals $SF_{ERR}$ if the fine magnetometers 26b are out-of-range, and ignoring coarse error signals $SC_{ERR}$ from the coarse magnetometers 26a and considering fine error signals $SC_{ERR}$ from the fine magnetometers 26b if the fine magnetometers 26 are in-range. The management control loop 54 may monitor the spatial component of the total residual magnetic field $B_{TOT}$ and the overall behavior and history of the signal at each fine magnetometer 26b to determine whether or not the fine magnetometer 26b is in-range or out-of-range. It is noted that the spatial components of the total residual magnetic field $B_{TOT}$ at the fine magnetometers 26b may be substantially different from each other, and thus, some of the fine magnetometers 26b may be in-range, while other fine magnetometers 26b may be out-of-range.

With knowledge of whether each of the fine magnetometers 26b are in-range or out-of-range, the management control loop 54 may generally activate the fine feedback control loop 52 after initiating activation of the coarse feedback control loop 50. In this manner, as discussed above, the coarse feedback control loop 50 may coarsely control the actuated magnetic field $B_{ACT}$ in a manner that at least partially cancels the outside magnetic field $B_{OUT}$, and thus suppresses the total residual magnetic field $B_{TOT}$ at the fine magnetometers 26b to a baseline level, such that the at least one of magnetometers 26b comes in-range. The management control loop 54 may then activate the feedback control loop 52 to finely control the actuated magnetic field $B_{ACT}$ in a manner that further suppresses the total residual magnetic field $B_{TOT}$ at the fine magnetometer(s) 26b that just came in-range to a lower level.

In one embodiment, the management control loop 54 strictly activates only the coarse feedback control loop 50 (e.g., if one of the fine magnetometers 26b is out-of-range) or only the fine feedback control loop (e.g., if all of the fine magnetometers 26 are in-range), but not both the coarse feedback control loop 50 and the fine feedback control loop 52 at the same time. In this case, the management control loop 54 will only consider coarse error signals $SC_{ERR}$ from the coarse magnetometers 26a when the coarse feedback control loop 50 is active, and will only consider fine error signals $SF_{ERR}$ from the fine magnetometers 26b when the fine feedback control loop 52 is active.

In another particularly preferred embodiment, however, the management control loop 54, at any given time, may not strictly activate only the coarse feedback control loop 50 or strictly activate only the fine feedback control loop 52, and thus, both of the coarse feedback control loop 50 and fine feedback control loop 52 may be at least partially activated. The management control loop 54 may choose to consider only the fine error signals $SF_{ERR}$ from the fine magnetometers 26b that are in-range. In this case, the management control loop 54 may determine whether or not the fine magnetometer 26b is in-range, and performs a "sensor hand-off" procedure, and in particular, switches back and forth between consideration of a coarse error signal $SC_{ERR}$ from any given coarse magnetometer 26a and consideration of a fine error signal $SF_{ERR}$ from any given fine magnetometer 26b. It is understood that only some of the fine magnetometers 26b may be out-of-range at any given moment, so the sensor hand-off procedure can be from one, some, or all coarse magnetometers 26a to one, some, or all of the fine magnetometers 26b.

For example, if the management control loop 54 is currently considering a coarse error signal $SC_{ERR}$ from a coarse magnetometer 26, and a previously unavailable fine magnetometer 26b is deemed to be in-range, the processor 30 may then ignore a coarse error signal $SC_{ERR}$ from at least one coarse magnetometer 26a that is in proximity to the previously unavailable fine magnetometer 26b, and instead consider the more accurate fine error signal $SF_{ERR}$ from this previously unavailable fine magnetometer 26b (in essence, passing or handing off detection of the total residual magnetic field $B_{TOT}$ from the coarse magnetometer(s) 26b to the fine magnetometer 26b).

On the contrary, if the management control loop 54 is currently considering a fine error signal $SF_{ERR}$ from a fine magnetometer 26b, and the fine magnetometer 26b is subsequently deemed to fall out-of-range for any one of a variety of reasons (e.g., if the user 12, and thus the fine magnetometer 26b, gets too close to a power outlet, a fridge magnet, a cell phone, or perhaps if the user 12 turns their head so suddenly that the total residual magnetic field $B_{TOT}$ to which the fine magnetometer 26b varies too quickly), the management control loop 54 may then ignore the fine error signal $SF_{ERR}$ from that fine magnetometer 26b, and instead consider the coarse error signal $SC_{ERR}$ from at least one coarse magnetometer 26a in proximity to the now unavailable fine magnetometer 26b (in essence, passing or handing off detection of the total residual magnetic field $B_{TOT}$ from the fine magnetometer 26b to the coarse magnetometer 26a).

Thus, in this manner, the management control loop 54 may operate the fine feedback control loop 52 to control the actuated magnetic field $B_{ACT}$ based on the fine error signals $SF_{ERR}$ respectively output by fine magnetometers 26b as they come in-range. The management control loop 54 may operate the fine feedback control loop 52 to prevent control of the actuated magnetic field $B_{ACT}$ based on the fine error signals $SF_{ERR}$ respectively output by fine magnetometers 26b as they go out-of-range.

In an optional embodiment, the management control loop 54 may weight the fine magnetometers 26b, in which case, the management control loop 54 may not perform a "sensor hand-off" procedure, per se, but may assign a weight a to any given fine magnetometer 26b between a value 0 (no weight) and 1 (full weight). For example, the management control loop 54 may monitor different operating parameters of a fine magnetometer 26b to determine whether the fine magnetometer 26b is in a linear operating range, or outside of the linear operating range, but not saturated (non-linear operating range), or is saturated. If the fine magnetometer 26b is found to be in the linear operating range, the weighting a assigned to the fine magnetometer 26b can be 1 (i.e., full weight); if the fine magnetometer 26b is found to be saturated, the weighting a assigned to the fine magnetometer 26b can be 0 (i.e., no weight); and if the fine magnetometer 26b is found to be in the non-linear operating range, the weighting a assigned to the fine magnetometer 26b can be between 0 and 1 (i.e., partial weight), depending on how close the fine magnetometer 26b is to saturation.

As discussed above, the management control loop 54 is configured for correcting factors that can change more slowly over time to optimize the cancellation of the outside magnetic field $B_{OUT}$. For example, the management control loop 54 may be configured for implementing adaptions to slow changes of the coarse feedback control loop 50 and fine feedback control loop 52 over time. The management control loop 54 is configured for identifying and determining parameters and coefficients of the signal acquisition unit 18a and the outside magnetic field $B_{OUT}$. The management control loop 54 is configured for employing computational algorithms to determine unknown parameters from the coarse error signals $SC_{ERR}$ and fine error signals $SF_{ERR}$ output by the coarse magnetometers 26a and fine magnetometers 26b, such as fitting of physical and calibrated mathematical and numerical models to the coarse error signals $SC_{ERR}$ and fine error signals $SF_{ERR}$ to identify missing or insufficiently known coefficients and parameters. Such parameters and coefficients can include offset and gain coefficients for the coarse magnetometers 26a, gain constants for the fine magnetometers 26b, actuator gains and offsets for the set of magnetic field actuators 28, electronics time delay latency coefficients in the coarse feedback control loop 50 and fine feedback control loop 52 (i.e., the amount of time between generating the coarse error signal $SC_{ERR}$ or fine error signal $SF_{ERR}$ and activating the set of magnetic field actuators 28), and other parameters of the signal acquisition unit 18a. The management control loop 54 may determine coefficients and parameters for different temporal and spatial ranges. Likewise, the gain that the set of magnetic field actuators 28 may have on the coarse magnetometers 26a and fine magnetometers 26b may differ with the placement and location offset of magnetic field actuators 28 (e.g., as the head of the user 12 moves or the support structure 24 deforms). The management control loop 54 may identify at least one, some, or all of the coefficients or parameters over these changing conditions.

In one exemplary instance, a mathematical and numerical model of the signal acquisition unit 18a, or a portion thereof, has some coefficients or parameters that are considered poorly or insufficiently known. In another exemplary instance, a mathematical and numerical model of the signal acquisition unit 18a does not have a predetermined structure, and the coefficients or parameters consist of transfer functions or linear mappings from one set of signals to another. The management control loop 54 may compare the response of a structured or unstructured model of the signal acquisition unit 18a to the measurements from the coarse magnetometers 26a and fine magnetometers 26b, and the coefficients or parameters may be varied until any disagreement between the mathematical model of the signal acquisition unit 18a and the actual measured signals is decreased. The coefficients or parameters of the mathematical model that achieve such a decrease in disagreement are the estimated parameters of the signal acquisition unit 18a (meaning, if the mathematical model with selected parameter values x, y, and z best matches the actual measured behavior of the system, then the values x, y, and z are a system identification estimate of the poorly or insufficiently known coefficients or parameters of the system). In determining the coefficients or parameters of the signal acquisition unit 18a, the management control loop 54 may employ weighted least squares, observer filters, Kalman filters, Wiener filters, or other filters. The management control loop 54 may employ time domain, frequency domain, recursive techniques, parametric and non-parametric methods, linear and nonlinear optimization techniques including gradient descent, matrix methods, convex methods, non-convex methods, neural networks, genetic algorithms, fuzzy logic, and machine learning methods.

The management control loop 54 may perform calibration techniques prior to operating the neural activity measurement system 10, or calibration techniques may be performed in real-time as the neural activity measurement system 10 operates. For example, prior to usage, the signal acquisition unit 18a may be calibrated by applying a known magnetic field in a controlled shielded setting (e.g., to characterize the coarse magnetometers 26a for their offsets and gain measurements). However, the properties of coarse magnetometers 26a, fine magnetometers 26b, or set of magnetic field actuators 28 may vary due to environmental variations, such as, e.g., variations in temperature, laser power (for magnetometers that utilize lasers), motion or deformation of the support structure 24, or other deformations, such as bending of the coarse magnetometers 26a, fine magnetometers 26b, or offset of magnetic field actuators 28 due to temperature or mechanical stresses. Thus, in addition to performing calibrations ahead of time, the management control loop 54 may perform calibrations techniques during system operation. For example, if the offsets and gains of the coarse magnetometers 26a change during usage of the neural activity measurement system 10, the management control loop 54 may estimate the offsets and gains of the coarse magnetometers 26a in real time (i.e., as the neural activity measurement system 10 is running), e.g., by estimating and comparing the offset of one coarse magnetometer against the measurements of other coarse or fine magnetometers. Further details discussing the calibration of coarse magnetometers are disclosed in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference.

It should be appreciated that, in the case where the signal acquisition unit 18a comprises multiple sets of magnetic field actuators 28 and processors 30, the components, along with the coarse feedback control loop 50, fine feedback control loop 52, and management control loop 54, illustrated in FIG. 4 may be duplicated. In this case, a subset of the coarse magnetometers 26a will be associated with each coarse feedback control loop 50, and a subset of the fine magnetometers 26b will be associated with each fine feedback control loop 52. Because the actuated magnetic field $B_{ACT}$ generated by each set of the magnetic field actuators 28 will affect all of the coarse magnetometers 26a and all of the fine magnetometers 26b, the processors 30 may communicate with each other to generate the proper noise-cancelling control signals C that will result in the composite cancelling magnetic field $B_{ACT}$ to be generated by the combination of sets of magnetic field actuators 28 to cancel the outside magnetic field $B_{OUT}$. Alternatively, a single processor 30 may be used to control all sets of the magnetic field actuators 26.

Another embodiment of a signal acquisition unit 18b takes advantage of the predictability and relatively slow variance of the amplitude and phase of the dominant low frequency components in a typical outside magnetic field $B_{OUT}$, including the essentially constant or slowly varying (0 to a few Hertz, or DC) Earth's magnetic field, which has a strength of approximately up to 50 μT, and time-varying magnetic fields of 60 Hz and its harmonics (120 Hz, 180 Hz, etc.) originating from electrical outlets and sockets, electrical equipment or electrical wires or connections in a laboratory, home, or office setting, which has amplitude of approximately 200 nT or greater.

Figure 5:
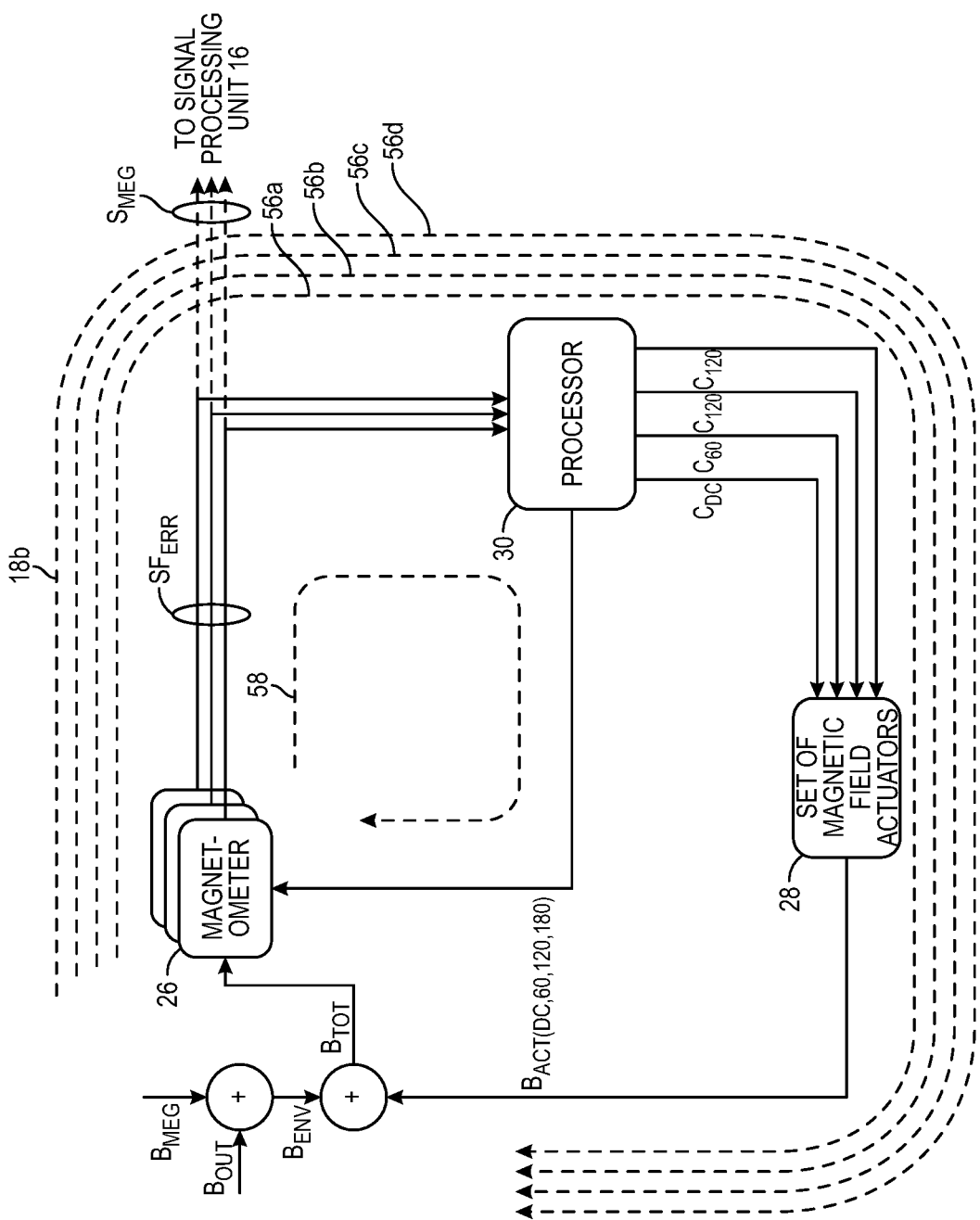
FIG. 5 is a block diagram of another exemplary embodiment of a signal acquisition unit used by the neural activity measurement system of FIG. 2.

In particular, and with reference to FIG. 5, the signal acquisition unit 18b is configured for at least partially cancelling the outside magnetic field $B_{OUT}$ in distinct frequency bands (namely at DC, and in 60 Hz, 120 Hz, 180 Hz, etc.) at the locations of the magnetometers 26 by employing a parallel set of feedback control loops 56 (in this case, one DC feedback control loop 56a and three harmonic feedback control loops 56b-56d). The signal acquisition unit 18b is also configured for managing the feedback control loops 56a-56d by employing a management control loop 58. It should be appreciated that the number of feedback control loops 56 may be more or less than four (as long as there is at least one feedback control loop 56 that cancels a harmonic of the outside magnetic field $B_{OUT}$), depending on the number of 60 Hz harmonics in the outside magnetic field $B_{OUT}$ to be cancelled, or alternatively, based on other sources of the outside magnetic field $B_{OUT}$, such as movement of the user 12.

The feedback control loops 56a-56d are implemented in the processor 30, with the feedback control loops 56a-56d coarsely controlling the set of magnetic field actuators 28 in response to input from the magnetometers 26. Although the set of feedback control loops 56a-56d are illustrated as receiving input from three magnetometers 26, it should be appreciated that the set of feedback control loop 56a-56d may receive input from more or less than three magnetometers 26, including only one magnetometer 26. In one embodiment, each of the magnetometers takes the form of a fine magnetometer 26b. In this case, the outside magnetic field $B_{OUT}$ can be cancelled using a suitable magnetic field cancellation technique (e.g., any of the techniques described in U.S. patent application Ser. No. 16/752,393, entitled "Neural Feedback Loop Filters for Enhanced Dynamic Range Magnetoencephalography (MEG) Systems and Methods," which is expressly incorporated herein by reference), broadband cancellation, and/or any of the harmonic frequency band cancellation techniques described below, such that the spatial components of the total residual magnetic field $B_{TOT}$ at the fine magnetometers 26b drop to a baseline level within the operating range of the fine magnetometers 26b.

In another embodiment, each of the magnetometers takes the form of a coarse magnetometer 26a. In the latter case, additional fine magnetometers 26b may be used to acquire the MEG signals $S_{MEG}$ representative of the spatial components of the MEG magnetic field $B_{MEG}$ for further processing by the signal processing unit 20 to identify and localize neural activity in the brain 14 of the user 12, but not used for cancellation of the outside magnetic field $B_{OUT}$.

Initially, the spatial components of the total residual magnetic field $B_{TOT}$ can be respectively detected by the magnetometers 26, which outputs error signals $S_{ERR}$ corresponding to the spatial components of the detected total residual magnetic field $B_{TOT}$, with each error signal $S_{ERR}$ containing the dominant DC, 60 Hz, 120 Hz, and 180 Hz frequency components. In one embodiment, the processor 30 acquires the error signals $S_{ERR}$ output by the magnetometers 26 in response to detecting the spatial components of the total residual magnetic field $B_{TOT}$, extracts characteristics of the dominant DC, 60 Hz, 120 Hz, and 180 Hz frequency components from each of the error signals $S_{ERR}$, computes the characteristics (namely the amplitude of the DC component, and the amplitude and phase of the 60 Hz, 120 Hz, and 180 Hz frequency components) of an actuated magnetic field $B_{ACT(DC,60,120,180)}$ estimated to minimize the error signals $S_{ERR}$ output by the magnetometers 26, and generates corresponding noise-cancelling control signals $C_{DC}$, $C_{60}$, $C_{120}$, and $C_{180}$ for output to the set of magnetic field actuators 28 for at least partially cancelling the outside magnetic field $B_{OUT}$ at DC, 60 Hz, 120 Hz, and 180 Hz at the fine magnetometers 26b, and ultimately suppressing the total residual magnetic field $B_{TOT}$ at DC, 60 Hz, 120 Hz, and 180 Hz to a baseline level at the fine magnetometers 26b.

In accordance with the noise-cancelling control signals $C_{DC}$, $C_{60}$, $C_{120}$, and $C_{180}$ output by the processor 30, the set of magnetic field actuators 28 generates the actuated magnetic field $B_{ACT(DC,60,120,180)}$ at DC, 60 Hz, 120 Hz, and 180 Hz, which combines with the outside magnetic field $B_{OUT}$ (along with weak MEG magnetic field $B_{MEG}$ from the brain 14) to create a total residual magnetic field $B_{TOT}$ at the magnetometers 26 having spatial components that are at the baseline level within the operating range of the magnetometers 26.

It should be appreciated that, in the illustrated embodiment, the magnetometers 26 are capable of detecting the total residual magnetic field $B_{TOT}$ in three dimensions (x, y, and z), and the set of magnetic field actuators 28 includes three magnetic field actuators 28a-28c (shown in FIG. 2) capable of generating the actuated magnetic field $B_{ACT}$ in three dimensions (x, y, and z). As such, each of the error signals S ERR respectively output by the magnetometers 26 to the processor 30, and each of the control signals $C_{DC}$, $C_{60}$, $C_{120}$, and $C_{180}$ output by the processor 30 to the respective magnetic field actuators 28a-28c, is a vector (i.e., comprises an x-component, y-component, and z-component), such that the outside magnetic field $B_{OUT}$ can be cancelled, and thus the total residual magnetic field $B_{TOT}$ suppressed, in three dimensions.

Notably, in a feedback control loop that reacts to oscillatory signals, the magnetometers, magnetic field actuators, and associated electronics (e.g., electronics that have longer latencies) should have a bandwidth that exceeds the speed of the oscillations. For instance, the magnetometers, magnetic field actuators, and associated electronics of a feedback control loop that is designed to respond to a measured oscillatory signal at 180 Hz should react substantially faster than $1/180^{th}$ of a second (i.e., 5 ms). In such an example, the feedback control loop may need to function with a bandwidth that is large compared to 180 Hz (i.e., a feedback control loop having a latency no more than 1 ms). However, feedback control loops that function substantially faster than 5 ms imposes restrictions on the magnetometers, magnetic field actuators, and associated electronics, and those restrictions can be severe and undesirable in terms of feasibility, weight, complexity, power, and cost. For instance, faster flux gate magnetometers may require more advanced, power hungry, expensive electronics. Likewise, OPMs have desired operating ranges and natural limits on bandwidth, and may not be feasibly operable at fast bandwidths, or the electronics that perform the calculations required for processing OPM outputs may not be able to function with sufficiently small (fast) latency.

For these reasons it is advantageous to enable operation of feedback control loops for noise inputs with fast oscillations using sensors, actuators, and electronics that have limited speed. In contrast, to a high bandwidth feedback control loop that attempts to directly compensate (i.e., respond directly to the raw underlying oscillatory components of the error signals) for the outside magnetic field $B_{OUT}$ at 60 Hz and harmonics thereof, which may cause phase shifts, and thus inaccuracies in the measurements and subsequent cancellation of the outside magnetic field $B_{OUT}$, if the magnetometers, magnetic field actuators, and associated electronics do not have sufficient bandwidth, instead the signal acquisition unit 18b may respond to the envelope amplitude and phase of the dominant frequency components (namely, the 60 Hz harmonics) of the error signals $S_{ERR}$, thereby enabling control of fast oscillatory signals with slower magnetometers, actuators, and/or electronics, as will be described in further detail below with respect to FIG. 10.

In particular, the processor 30 extracts the slowly varying amplitude and phase of the envelope of the dominant DC, 60 Hz, 120 Hz, and 180 Hz frequency components from each of the error signals $S_{ERR}$, and generates noise-cancelling control signals C Dc , $C_{60}$, $C_{120}$, and $C_{180}$ having a slowly varying amplitude and phase, such that the amplitude and phase of the actuated magnetic field $B_{ACT(DC,60,120,180)}$ at DC, 60 Hz, 120 Hz, and 180 Hz slowly varies in a similar fashion. Thus, despite the limited bandwidth and speed of the magnetometer 26, magnetic field actuators 28, and other electronics, the signal acquisition unit 18b is capable of effectively cancelling the outside magnetic field $B_{OUT}$. Furthermore, since the feedback control loops 56a-56d are operated at narrow bandwidths around DC, 60 HZ, 120 Hz, and 180 Hz, only noise at these narrow bandwidths and from the magnetometers 26, themselves, will be fed back into the system, which is in contrast to direct, broadband, feedback, where noise in the entire bandwidth of the feedback control loop is fed back into the system. This has the advantage of injecting less noise back into the system, and thus improving the signal to noise ratio of MEG magnetic field $B_{OUT}$ measurements.

The processor 30 employs the management control loop 58 for correcting additional factors that can change more slowly over time in a similar manner performed by the management control loop 54 of the signal acquisition unit 18a of FIG. 4, as applied to the parallel set of feedback control loops 56a-56d.

It should be appreciated that, in the case where the signal acquisition unit 18b comprises multiple sets of magnetic field actuators 28 and processors 30, the components, along with the parallel set of feedback control loops 56a-56d, and management control loop 58, illustrated in FIG. 5, may be duplicated. In this case, a subset of the magnetometer 26 will be associated with each set of feedback control loops 56a-56d. Because the actuated magnetic field $B_{ACT(DC,60,120,180)}$ generated by each set of the magnetic field actuators 28 will affect all of the magnetometers 26, the processors 30 may communicate with each other to generate the proper noise-cancelling control signals $C_{DC}$, $C_{60}$, $C_{120}$, and $C_{180}$ that will result in the composite cancelling magnetic field $B_{ACT(DC,60,120,180)}$ at DC, 60 Hz, 120 Hz, and 180 Hz to be generated by the combination of sets of magnetic field actuators 28 to cancel the outside magnetic field $B_{OUT}$. Alternatively, a single processor 30 may be used to control all sets of the magnetic field actuators 26.

It should also be appreciated that although the harmonic cancellation technique performed by the signal acquisition unit 18b has been described to cancel the outside magnetic field $B_{OUT}$ at 60 Hz, 120 Hz, and 180 Hz, additional harmonic feedback control loops can be added to cancel the outside magnetic field $B_{OUT}$ at 60 Hz, 120 Hz, and 180 Hz at additional harmonics, including 240 Hz, 300 Hz, 360 Hz . . . K*60 Hz . . . , where K is an integer. Furthermore, although the harmonic cancellation technique performed by the signal acquisition unit 18b has been described to cancel the outside magnetic field $B_{OUT}$ at harmonics of 60 Hz, other frequency harmonics can also be cancelled. For example, in Europe power line frequencies are 50 Hz, so alternative embodiments of the signal acquisition unit 18b may cancel the outside magnetic field $B_{OUT}$ at harmonics, including 50 Hz, 100 Hz, 150 Hz . . . K*50 Hz . . . .

It should also be appreciated that, although preferred, it may not be necessary for the harmonic cancellation technique performed by the signal acquisition unit 18b to exactly match the harmonic frequencies in the outside magnetic field $B_{OUT}$. For example, if the outside magnetic field $B_{OUT}$ contains a harmonic at 59 Hz (e.g., if the noise from electrical power in the room is actually 59 Hz, rather than at 60 Hz), but the harmonic cancellation technique is performed at harmonics of 60 Hz, then that mismatch between 59 Hz and 60 Hz will result in a slower "beat" frequency error of 1 Hz (i.e., 60 Hz–59 Hz=1 Hz) that will be contained in the error signals $S_{ERR}$ respectively output by the magnetometers 26. However, the DC feedback control loop 56a (which may be capable of cancelling frequencies up to 5 Hz) will effectively be able to cancel the outside magnetic field $B_{OUT}$ at 1 Hz, and therefore, correct for this beat frequency. In another example, if the outside magnetic field $B_{OUT}$ contains a harmonic at 182 Hz, but the harmonic cancellation technique is performed at harmonics of 60 Hz, then that mismatch between 180 Hz and 182 Hz will result in a slower "beat" frequency error of 2 Hz (i.e., 182 Hz–180 Hz=2 Hz) that will be contained in the error signals S ERR respectively output by the magnetometers 26. However, again, the DC feedback control loop 56a will effectively be able to cancel the outside magnetic field $B_{OUT}$ at 2 Hz, and therefore, correct for this beat frequency. Thus, the DC feedback control loop 56a can detect and correct for mismatches between anticipated and actual noise frequencies.

Still another embodiment of a signal acquisition unit 18c combines the advantages of the signal acquisition unit 18a illustrated in FIG. 4 and the signal acquisition unit 18b illustrated in FIG. 5; that is, the signal acquisition unit 18c takes advantage of the high dynamic range of the coarse magnetometers 26a to compensate for the relatively low dynamic range of the fine magnetometers 26b to cancel the large outside magnetic field $B_{OUT}$, while also taking advantage of high sensitivity of the fine magnetometers 26b to compensate for the low sensitivity of the coarse magnetometers 26a to measure the MEG signal $S_{MEG}$, and furthermore, takes advantage of the predictability and relatively slow variance of the amplitude and phase of the dominant low frequency components in a typical outside magnetic field $B_{OUT}$.

Figure 6:
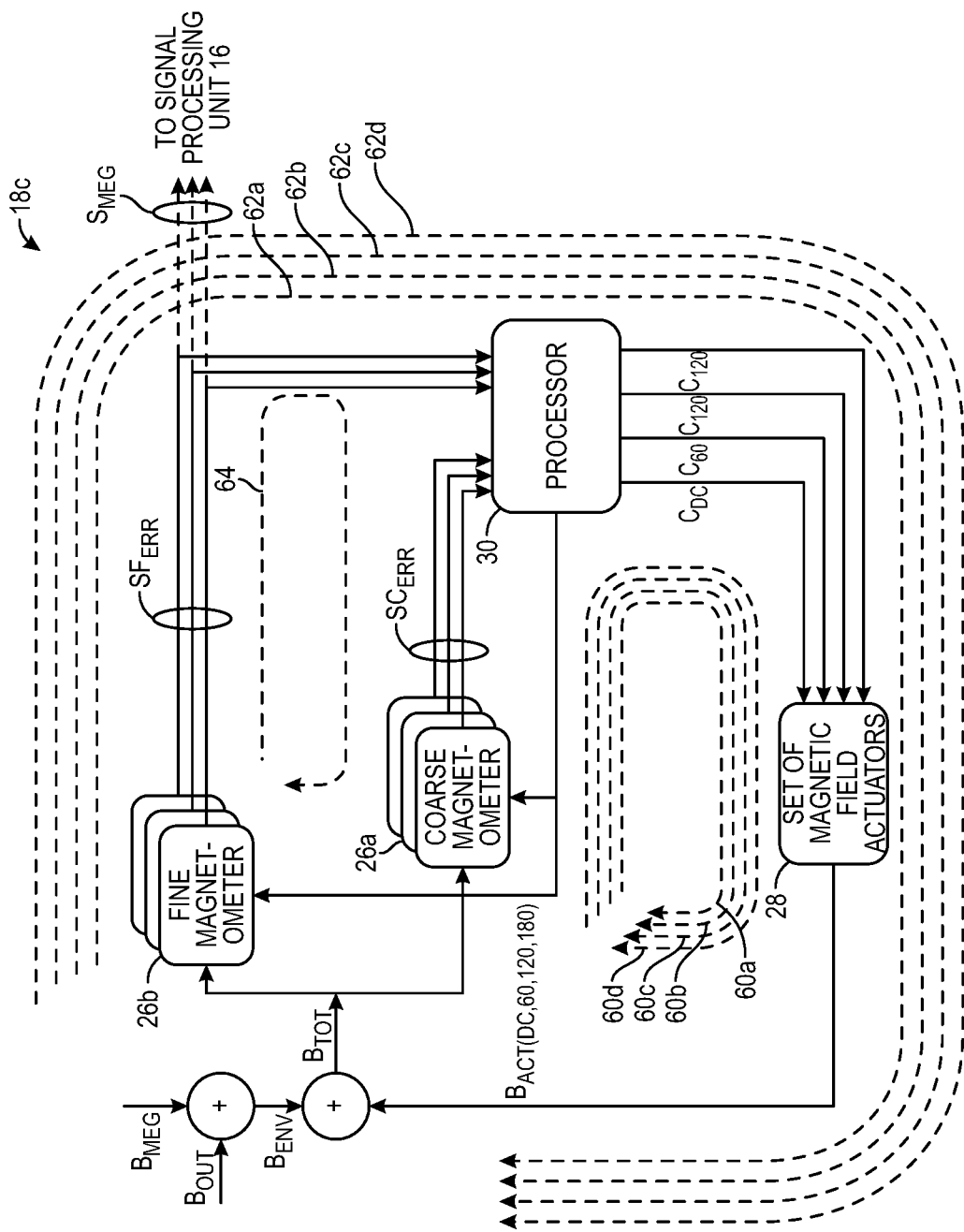
FIG. 6 is a block diagram of still another exemplary embodiment of a signal acquisition unit used by the neural activity measurement system of FIG. 2.

In particular, and with reference to FIG. 6, the signal acquisition unit 18c is configured for cancelling the outside magnetic field $B_{OUT}$ in distinct frequency bands (namely at DC, 60 Hz, 120 Hz, 180 Hz, etc.) at the locations of the fine magnetometers 26b by initially employing a parallel set of coarse feedback control loops 60 (in this case, one coarse DC feedback control loop 60a and three coarse harmonic feedback control loops 60b-60d) having relatively low sensitivities, but relatively high dynamic ranges, for coarsely cancelling the outside magnetic field $B_{OUT}$ at these distinct frequency bands, such that the spatial components of the total residual magnetic field $B_{TOT}$ at the fine magnetometers 26b drops to a baseline level within the operating range of the fine magnetometers 26b, and subsequently employing a parallel set of fine feedback control loops 62 (in this case, one fine DC feedback control loop 62a and three fine harmonic feedback control loops 62b-62d) having relatively low sensitivities, but low dynamic ranges that encompasses this baseline level for finely cancelling the outside magnetic field $B_{OUT}$ (e.g., by any of the techniques described in U.S. patent application Ser. No. 16/752,393, entitled "Neural Feedback Loop Filters for Enhanced Dynamic Range Magnetoencephalography (MEG) Systems and Methods," which is expressly incorporated herein by reference), broadband cancellation, and/or the harmonic frequency band cancellation techniques described below, such that the spatial components of the total residual magnetic field $B_{TOT}$ at the fine magnetometers 26b further drops from the baseline level to an even lower level. The signal acquisition unit 18c is also configured for managing the parallel set of coarse feedback control loops 60a-60d and parallel set of fine feedback control loops 62a-62d by employing a management control loop 64.

It should be appreciated that the number of coarse feedback control loops 60 or the number of fine feedback control loops 62 may be more or less than four, depending on the number of 60 Hz harmonics in the outside magnetic field $B_{OUT}$ to be cancelled, or alternatively, based on other sources of outside magnetic field $B_{OUT}$, such as movement of the user 12.

The set of coarse feedback control loops 60a-60d and set of fine feedback control loops 60a-60d are implemented in the processor 30, with the set of coarse feedback control loops 60a-60d coarsely controlling the set of magnetic field actuators 28 in response to input from the coarse magnetometers 26a, and the set of fine feedback control loops 62a-62d finely controlling the set of magnetic field actuators 28 in response to input from the fine magnetometers 26b. Although the set of coarse feedback control loops 60a-60d are illustrated as receiving input from three coarse magnetometers 26a, and the set of fine feedback control loops 62a-62d are illustrated as receiving input from three fine magnetometers 26b, it should be appreciated that the set of coarse feedback control loops 60a-60d can receive input from more or less coarse magnetometers 26a, including only one coarse magnetometer 26a, and set of fine feedback control loops 62a-62d can receive input from more or less fine magnetometers 26b, including only one fine magnetometer 26b. Furthermore, although set of coarse feedback control loops 60a-60d and set of fine feedback control loops 62a-62d are illustrated as receiving input from an equal number of coarse magnetometers 26a and fine magnetometers 26b, the set of coarse feedback control loops 60a-60d and set of fine feedback control loops 62a-62d may receive input from an unequal number of coarse magnetometers 26a and fine magnetometers 26b, including a number of coarse magnetometers 26a that is greater or less the number of fine magnetometers 26b.

Initially, due to the relatively low dynamic range of the fine magnetometers 26b, the magnitude of the total residual magnetic field $B_{TOT}$ is too great for the fine magnetometers 26b to detect the total residual magnetic field $B_{TOT}$. However, due to the relatively high dynamic range of the coarse magnetometers 26a, the spatial components of the total residual magnetic field $B_{TOT}$ can be respectively detected by the coarse magnetometers 26a, which outputs coarse error signals $SC_{ERR}$ corresponding to the spatial components of the detected total residual magnetic field $B_{TOT}$, with each coarse error signal $SC_{ERR}$ containing the dominant DC, 60 Hz, 120 Hz, and 180 Hz frequency components.

When the magnitude of the total residual magnetic field $B_{TOT}$ is above the dynamic range of the fine magnetometers 26b, the processor 30 acquires the coarse error signals $SC_{ERR}$ output by the coarse magnetometers 26a in response to detecting the spatial components of the total residual magnetic field $B_{TOT}$, extracts characteristics of the dominant DC, 60 Hz, 120 Hz, and 180 Hz frequency components from each of the coarse error signals $SC_{ERR}$, computes the characteristics (namely the amplitude of the DC component, and the amplitude and phase of the 60 Hz, 120 Hz, and 180 Hz frequency components) of the actuated magnetic field $B_{ACT(DC,60,120,180)}$ estimated to minimize the coarse error signals $SC_{ERR}$ output by the coarse magnetometers 26a, and generates corresponding noise-cancelling control signals $C_{DC}$, $C_{60}$, $C_{120}$, and $C_{180}$ for output to the set of magnetic field actuators 28 for at least partially cancelling the outside magnetic field $B_{OUT}$ at DC, 60 Hz, 120 Hz, and 180 Hz at the fine magnetometers 26b, and ultimately suppressing the total residual magnetic field $B_{TOT}$ at DC, 60 Hz, 120 Hz, and 180 Hz to a baseline level at the fine magnetometers 26b.

In one embodiment, the processor 30 may estimate the spatial components of the total residual magnetic field $B_{TOT}$ respectively at DC, 60 Hz, 120 Hz, and 180 Hz and at the fine magnetometers 26b based on the dominant DC, 60 Hz, 120 Hz, and 180 Hz frequency components extracted from the coarse error signal $SC_{ERR}$, e.g., using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", which is expressly incorporated herein by reference.

In accordance with the noise-cancelling control signals $C_{DC}$, $C_{60}$, $C_{120}$, and $C_{180}$ output by the processor 30, the set of magnetic field actuators 28 generates the actuated magnetic field $B_{ACT(DC,60,120,180)}$ at DC, 60 Hz, 120 Hz, and 180 Hz, which combines with the outside magnetic field $B_{OUT}$ (along with weak MEG magnetic field $B_{MEG}$ from the brain 14) to create a total residual magnetic field $B_{TOT}$ at the fine magnetometers 26b having spatial components at a baseline level within the operating range of the fine magnetometers 26b.

Once the spatial components of the total residual magnetic field $B_{TOT}$ at the fine magnetometers 26b are at the baseline level, they can be respectively detected by the fine magnetometers 26b, which outputs fine error signals $SF_{ERR}$ corresponding to the spatial components of the detected total residual magnetic field $B_{TOT}$, with each fine error signal $SF_{ERR}$ containing the dominant DC, 60 Hz, 120 Hz, and 180 Hz frequency components. The processor 30 then acquires the fine error signals $SF_{ERR}$ output by the fine magnetometers 26b in response to detecting the spatial components of the total residual magnetic field $B_{TOT}$, extracts characteristics of the dominant DC, 60 Hz, 120 Hz, and 180 Hz frequency components from each of the fine error signals $SF_{ERR}$, computes the characteristics (namely the amplitude of the DC component, and the amplitude and phase of the 60 Hz, 120 Hz, and 180 Hz frequency components) of the actuated magnetic field $B_{ACT(DC,60,120,180)}$ estimated to minimize the fine error signals $SF_{ERR}$ output by the fine magnetometers 26b, and generates corresponding noise-cancelling control signals $C_{DC}$, $C_{60}$, $C_{120}$, and $C_{180}$ for output to the set of magnetic field actuators 28 for finely cancelling the outside magnetic field $B_{OUT}$ at DC, 60 Hz, 120 Hz, and 180 Hz at the fine magnetometers 26b, and ultimately suppressing the total residual magnetic field $B_{TOT}$ at DC, 60 Hz, 120 Hz, and 180 Hz to a lower level than the baseline level at the fine magnetometers 26b.

In one embodiment, even when the spatial components of the total residual magnetic field $B_{TOT}$ at the fine magnetometers 26b is at the baseline level, and the fine error signals $SF_{ERR}$ output by the fine magnetometers 26b are being actively acquired, the processor 30 may be further configured for correcting or refining the fine error signals $SF_{ERR}$ using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", and/or U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which are expressly incorporated herein by reference.

In accordance with the noise-cancelling control signals $C_{DC}$, $C_{60}$, $C_{120}$, and $C_{180}$ output by the processor 30, the set of magnetic field actuators 28 generates the actuated magnetic field $B_{ACT(DC,60,120,180)}$ at DC, 60 Hz, 120 Hz, and 180 Hz, which combines with the outside magnetic field $B_{OUT}$ (along with weak MEG magnetic field $B_{MEG}$ from the brain 14) into a total residual magnetic field $B_{TOT}$ at the fine magnetometers 26b having spatial components at a level lower than the baseline level. At this point, the fine error signals $SF_{ERR}$ can serve as MEG signals SMEs representative of the spatial components of the MEG magnetic field $B_{MEG}$ for further processing by the signal processing unit 20 to identify and localize neural activity in the brain 14 of the user 12.

It should be appreciated that, in the illustrated embodiment, the coarse magnetometers 26a and fine magnetometers 26b are capable of detecting the total residual magnetic field $B_{TOT}$ in three dimensions (x, y, and z), and the set of magnetic field actuators 28 includes three magnetic field actuators 28a-28c (shown in FIG. 2) capable of generating the actuated magnetic field $B_{ACT}$ in three dimensions (x, y, and z). As such, each of the coarse error signals $SC_{ERR}$ and fine error signals $SF_{ERR}$ respectively output by the coarse magnetometers 26a and fine magnetometers 26b to the processor 30, and each of the control signals $C_{DC}$, $C_{60}$, $C_{120}$, and $C_{180}$ output by the processor 30 to the respective magnetic field actuators 28a-28c, is a vector (i.e., comprises an x-component, y-component, and z-component), such that the outside magnetic field $B_{OUT}$ can be cancelled, and thus the total residual magnetic field $B_{TOT}$ suppressed, in three dimensions.

In a preferred embodiment, instead of extracting the highly varying amplitude and phase of the dominant DC, 60 Hz, 120 Hz, and 180 Hz frequency components from each underlying coarse error signals $SC_{ERR}$ or each of the underlying fine error signals $SF_{ERR}$, the processor 30 extracts the slowly varying amplitude and phase of the envelope of the dominant DC, 60 Hz, 120 Hz, and 180 Hz frequency components from each of the coarse error signals $SC_{ERR}$ or each of the fine error signals $SF_{ERR}$, and generates noise-cancelling control signals $C_{DC}$, $C_{60}$, $C_{120}$, and $C_{180}$ having a slowly varying amplitude and phase, such that the amplitude and phase of the actuated magnetic field $B_{ACT(DC,60,120,180)}$ at DC, 60 Hz, 120 Hz, and 180 Hz slowly varies in a similar fashion.

Thus, it can be appreciated that, in contrast to a high bandwidth feedback control loop that attempts to directly compensate for the outside magnetic field $B_{OUT}$ at 60 Hz and harmonics thereof, which may cause phase shifts due to the finite bandwidth of a typical fine magnetometer, as discussed above with respect to the signal acquisition unit 18b, the signal acquisition unit 18c is capable of effectively cancelling the outside magnetic field $B_{OUT}$ despite the limited bandwidth of the magnetometer 26. Furthermore, since the coarse feedback control loops 60a-60d and the fine feedback control loops 62a-62d are operated at narrow bandwidths around DC, 60 HZ, 120 Hz, and 180 Hz, only noise at these narrow bandwidths and from the magnetometers 26, themselves, will be fed back into the system, which is in contrast to direct, broadband, feedback, where noise in the entire bandwidth of the feedback control loop is fed back into the system.

In an alternative embodiment, the signal acquisition unit 18c only employs the parallel set of coarse feedback control loops 60a-60d for cancelling the outside magnetic field $B_{OUT}$, such that the spatial components of the total residual magnetic field $B_{TOT}$ at the fine magnetometers 26b drop to a baseline level within the operating range of the fine magnetometers 26b. In this case, the processor 30 only uses the coarse error signals $SC_{ERR}$ output by the coarse magnetometers 26a to compute the characteristics of the actuated magnetic field $B_{ACT(DC,60,120,180)}$ at DC, 60 Hz, 120 Hz, and 180 Hz estimated to suppress the total residual magnetic field $B_{TOT}$ to near-zero at the fine magnetometers 26b, even after the spatial components of the total residual magnetic field $B_{TOT}$ at the fine magnetometers 26b are already at the baseline level, such that the fine magnetometers 26b remain in the operating range.

Whether the signal acquisition unit 18c employs both the parallel set of coarse feedback control loops 60a-60d and the parallel set of fine feedback control loops 62a-62d to cancel the outside magnetic field $B_{OUT}$, or employs only the parallel set of coarse feedback control loops 60a-60d to cancel the outside magnetic field $B_{OUT}$, it can be appreciated that the signal acquisition unit 18c is capable of coarsely canceling a large portion of the outside magnetic field $B_{OUT}$, while still being sensitive enough to measure the weaker MEG magnetic field $B_{MEG}$ generated by the neural activity in the brain 14 of the user 12.

The processor 30 employs the management control loop 64 to manage how the parallel set of coarse feedback control loops 60a-60d and the parallel set of fine feedback control loops 62a-62d are employed (e.g., how the coarse error signals $SC_{ERR}$ output by the coarse magnetometers 26a and the fine error signals $SF_{ERR}$ output by the fine magnetometers 26b are to be used) for optimal cancellation of the outside magnetic field $B_{OUT}$ at DC, 60 Hz, 120 Hz, and 180 Hz, and thus optimal suppression of the total residual magnetic field $B_{TOT}$ at DC, 60 Hz, 120 Hz, and 180 Hz. In this regard, the management control loop 64 may function in the same manner as the management control loop 54 of the signal acquisition unit 18a of FIG. 4. The processor 30 employs the management control loop 64 for correcting additional factors that can change more slowly over time in a similar manner performed by the management control loop 54 of the signal acquisition unit 18a of FIG. 4, as applied to the parallel set of coarse feedback control loops 60a-60d and parallel set of fine feedback control loops 62a-62d. Further details on optimal cancellation techniques are disclosed in U.S. Provisional Application Ser. No. 62/975,727, entitled "Optimal Methods to Feedback Control and Estimate Magnetic Fields to Enable a Wearable MEG System to Measure Magnetic Fields from the Brain", which is expressly incorporated herein by reference.

It should be appreciated that, in the case where the signal acquisition unit 18c comprises multiple sets of magnetic field actuators 28 and processors 30, the components, along with the parallel set of coarse feedback control loops 60a-60d, parallel set of fine feedback control loops 62a-62d, and management control loop 64, illustrated in FIG. 6 may be duplicated. In this case, a subset of the coarse magnetometers 26a will be associated with each parallel set of coarse feedback control loops 60a-60d, and a subset of the fine magnetometers 26b will be associated with each parallel set of fine feedback control loops 62a-62d. Because the actuated magnetic field $B_{ACT(DC,60,120,180)}$ generated by each set of the magnetic field actuators 28 will affect all of the coarse magnetometers 26a and all of the fine magnetometers 26b, the processors 30 may communicate with each other to generate the proper noise-cancelling control signals $C_{DC}$, $C_{60}$, $C_{120}$, and $C_{180}$ that will result in the composite cancelling magnetic field $B_{ACT(DC,60,120,180)}$ to be generated by the combination of sets of magnetic field actuators 28 at DC, 60 Hz, 120 Hz, and 180 Hz to cancel the outside magnetic field $B_{OUT}$. Alternatively, a single processor 30 may be used to control all sets of the magnetic field actuators 26.

It should also be appreciated that although the harmonic cancellation technique performed by the signal acquisition unit 18c has been described to cancel the outside magnetic field $B_{OUT}$ at 60 Hz, 120 Hz, and 180 Hz, additional coarse and fine harmonic feedback control loops can be added to cancel the outside magnetic field $B_{OUT}$ at 60 Hz, 120 Hz, and 180 Hz at additional harmonics, including 240 Hz, 300 Hz, 360 Hz . . . K*60 Hz . . . , where K is an integer. Furthermore, although the harmonic cancellation technique performed by the signal acquisition unit 18c has been described to cancel the outside magnetic field $B_{OUT}$ at harmonics of 60 Hz, other frequency harmonics can also be cancelled. For example, in Europe power line frequencies are 50 Hz, so alternative embodiments of the signal acquisition unit 18b may cancel the outside magnetic field $B_{OUT}$ at harmonics, including 50 Hz, 100 Hz, 150 Hz . . . K*50 Hz . . . . Furthermore, in the same manner described above with respect to the signal acquisition unit 18b of FIG. 5, the DC coarse feedback control loops 60a and DC feedback control loops 62a can detect and correct for mismatches between anticipated and actual noise frequencies.

It should be appreciated that the error signals $S_{ERR}$ output by the magnetometers 26 in the signal acquisition unit 18b or the coarse error signals $SC_{ERR}$ and fine error signals $SR_{ERR}$ respectively output by the coarse magnetometers 26a and fine magnetometers 26b in the signal acquisition units 18a, 18c (or alternatively, the estimated spatial components of the total residual magnetic field $B_{TOT}$ at the fine magnetometers 26b of the signal acquisition units 18a, 18c) can be processed in parallel (whether weighted or unweighted) by the processor 30 to generate the noise-cancelling control signals C (or $C_{DC}$, $C_{60}$, $C_{120}$, and $C_{180}$) or can be filtered (e.g., computing the selecting the worst-case (highest) error signal or performing a statistical analysis (e.g., mean, standard deviation, moments), etc.).

It should also be appreciated that, although the use of the signal acquisition units 18a-18c illustrated in FIGS. 4-6 lend themselves well to neural activity measurement systems, the signal acquisition units 18a-18c may find use in other applications, such as, e.g., other types of biomedical sensing, vehicle navigation, mineral exploration, non-destructive testing, detection of underground devices, asteroid mining, space exploration, etc. Thus, signal acquisition units 18a-18c can be adapted to measure neural signals generated from non-brain anatomical structures, as well as other types of biological signals and non-biological signals.

Figure 7:
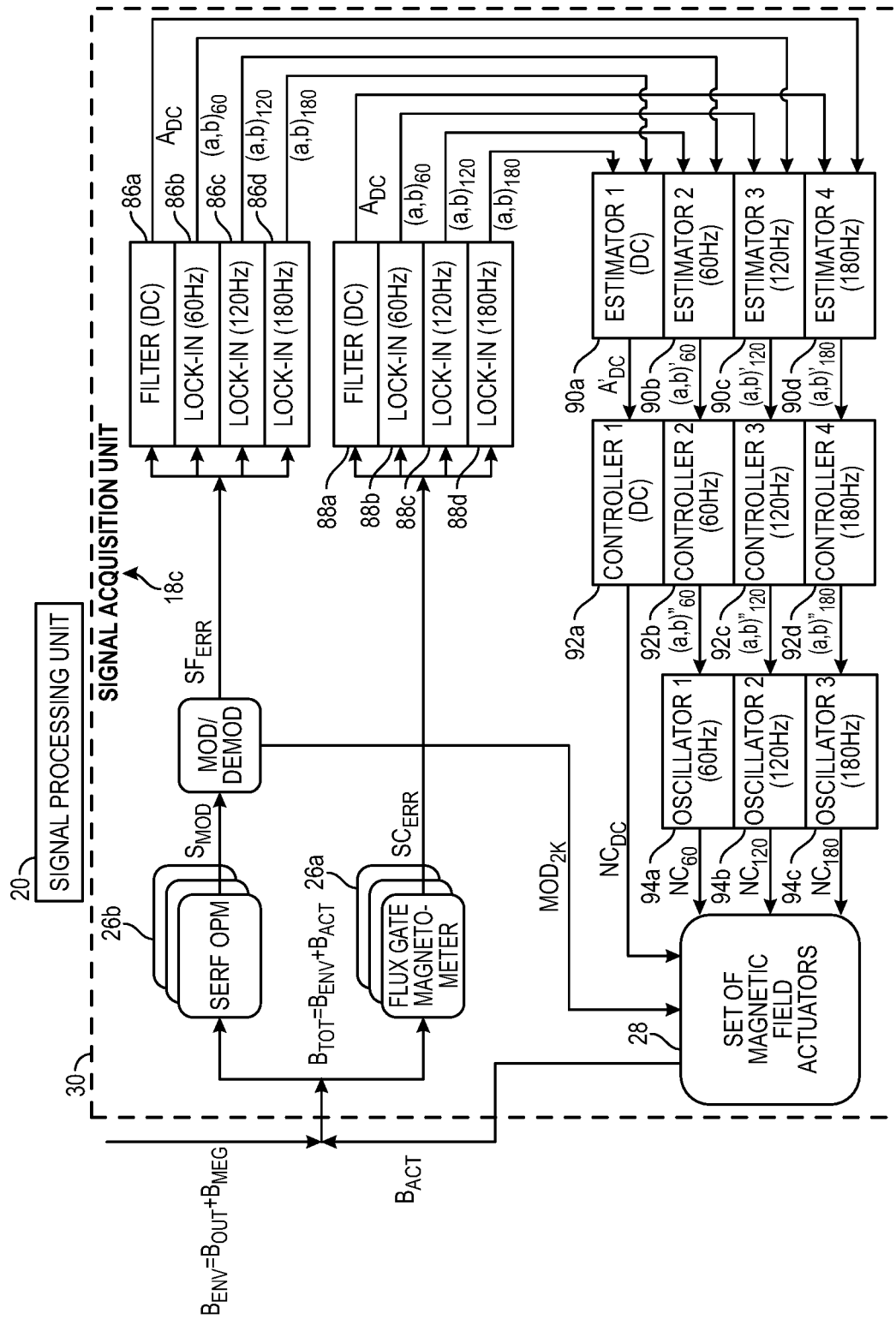
FIG. 7 is a detailed below diagram of the signal acquisition unit of FIG. 6.

Referring now to FIG. 7, an exemplary detailed embodiment of the signal acquisition unit 18c illustrated in FIG. 6 will be described. The signal acquisition unit 18c comprises the coarse magnetometers 26a, fine magnetometers 26b, a set of magnetic field actuators 28, and processor 30, which generally function to create the parallel set of coarse feedback control loops 60a-60d and the parallel set of fine feedback control loops 62a-62d in the same manner described above with respect to FIG. 6.

Each coarse magnetometer 26a coarsely detects a respective spatial component of the total residual magnetic field $B_{TOT}$, and outputs a coarse error signal $SC_{ERR}$ representative of the spatial component of the total residual magnetic field $B_{TOT}$ detected at that coarse magnetometer 26a. In the illustrated embodiment, each coarse magnetometer 26a takes the form of a flux gate magnetometer, which has a relatively low sensitivity (e.g., on the order of 100 fT), and thus, may not be capable of measuring weak magnetic fields generated by neural activity in the brain 14 of the user 12. However, a flux gate magnetometer has a relatively high dynamic sensitivity range (in the range of 100 fT to close to 100 μT), and thus, may operate in a large outside magnetic field. Although each of the coarse magnetometers 26a are described as taking the form of a flux gate magnetometer, other types of coarse magnetometers can be used, including, but not limited to, anisotropic magnetoresistance (AMR) sensors, tunnel magnetoresistance (TMR) sensors, Hall-effect sensors, nitrogen vacancy sensors, or any other magnetometer that can operate in a linear range over the amplitude range of typical outside magnetic field $B_{OUT}$.

Each fine magnetometer 26b finely detects a respective spatial component of the total residual magnetic field $B_{TOT}$, and outputs a fine error signal $SF_{ERR}$ representative of the spatial component of the total residual magnetic field $B_{TOT}$ detected at that fine magnetometers 26b. In the illustrated embodiment, each fine magnetometer 26b takes the form of a Spin Exchange Relaxation Free (SERF) Optically Pumped Magnetometer (OPM). Although a SERF OPM has a relatively small dynamic range (e.g., in the range of 1 ft to 200 nT), it has a relatively high sensitivity (on the order of 1 fT) to magnetic fields compared to flux gate magnetometers.

Figure 8:
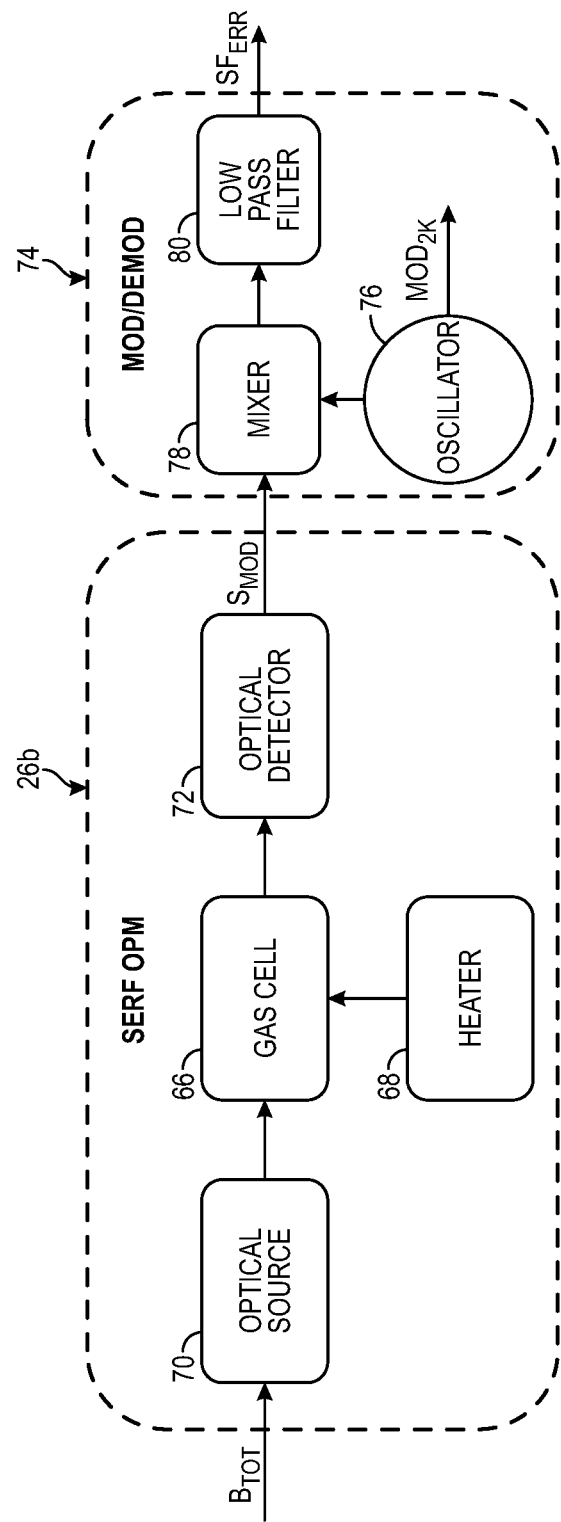
FIG. 8 is a block diagram of an exemplary Spin Exchange Relaxation Free (SERF) Optically Pumped Magnetometer (OPM) and modulator/demodulator used in the signal acquisition unit of FIG. 7.

Referring to FIG. 8, the SERF OPM 26b comprises an alkali metal gas cell 66, a heater 68, an optical source 70, and an optical detector 72.

The gas cell 66 is configured for containing an alkali metal vapor (for example, rubidium in natural abundance, isotopically enriched rubidium, potassium, or cesium, or any other suitable alkali metal such as lithium, sodium, or francium), quenching gas (for example, nitrogen) and buffer gas (for example, nitrogen, helium, neon, or argon). The heater 68 is configured for heating the gas cell 66.

The optical source 70 is configured for optically pumping and probing the alkali metal atoms, and may include, e.g., a laser, as well as optics (such as lenses, waveplates, collimators, polarizers, and objects with reflective surfaces) for beam shaping and polarization control and for directing the light from the optical source 104 to the gas cell 66 and optical detector 72. Examples of suitable optical sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source.

The optical detector 72 is configured for measuring the optical properties of the light field transmitted through gas cell 66, including amplitude, phase, or polarization, as quantified through optical absorption and dispersion curves, spectrum, or polarization or the like or any combination thereof. Examples of suitable optical detectors include, but are not limited to, a photodiode (PD), charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

As will be described in further detail below, the light transmitted through the gas cell 66 is modulated at a defined frequency, such that the optical detector 72 outputs the fine error signal $SF_{ERR}$, which is modulated with the same frequency in response to the modulated total residual magnetic field $B_{TOT}$ at the SERF OPM 26b. In this manner, the light travelling through the gas cell 66 is moved away from the low-frequency end of the spectrum in order to minimize low-frequency noise in the fine error signal $SF_{ERR}$, which may otherwise occur due to the high sensitivity of the SERF OPM 26b to low-frequency noise. Preferably, the light is modulated at a much greater frequency than the relaxation rate of the vapor (approximately 100 Hz) and a greater frequency than the expected frequency spectrum of neural activity in the brain 14 of the user 12. For example, the modulation frequency of the light may be, e.g., 2K Hz. As will also be described in further detail below, the fine error signal $SF_{ERR}$ output by the optical detector 106 may then be demodulated to shift the frequency components of the fine error signal $SF_{ERR}$ back to the low-frequency end of the spectrum.

Referring to FIGS. 7 and 8, the processor 30 comprises a modulator/demodulator 74 configured for modulating the light transmitted through the gas cell 66 from the optical source 70 to the optical detector 72, and for demodulating a modulated signal $S_{MOD}$ output by the optical detector 72 and outputting the fine error signal $SF_{ERR}$. In particular, the modulator/demodulator 74 comprises an oscillator 76 configured for sending an oscillatory signal $MOD_{2K}$ at a defined frequency to the set of magnetic field actuators 28, thereby modulating the actuated magnetic field $B_{ACT}$, and thus, the light transmitted through the gas cell 66 from the optical source 70 to the optical detector 72, thereby generating the modulated signal $S_{MOD}$. The modulator/demodulator 74 further comprises a mixer 78 configured for mixing the modulated signal $S_{MOD}$ and the oscillatory signal $MOD_{2K}$ to down-frequency shift the modulated signal $S_{MOD}$. The modulator/demodulator 74 further comprises a low-pass filter 80 configured for filtering the down-shifted modulated signal $S_{MOD}$ to yield the fine error signal $SF_{ERR}$.

It should be appreciated that each of the fine magnetometers 26b is preferably capable of detecting the total residual magnetic field $B_{TOT}$ in three dimensions (x, y, and z), and thus, the modulated signal $S_{MOD}$ output by each fine magnetometer 26b will be a directional vector. In this case, the processor 30 comprises two modulators/demodulators 74 respectively associated with the two of the orthogonal components (e.g., x and y) of the modulated signal $S_{MOD}$, with the oscillators 76 of the two modulators/demodulators 74 being out of phase by 90 degrees, thereby enabling quadrature detection of the x, y, and z directional components of the total residual magnetic field $B_{TOT}$ at the modulation frequency.

Figure 9:
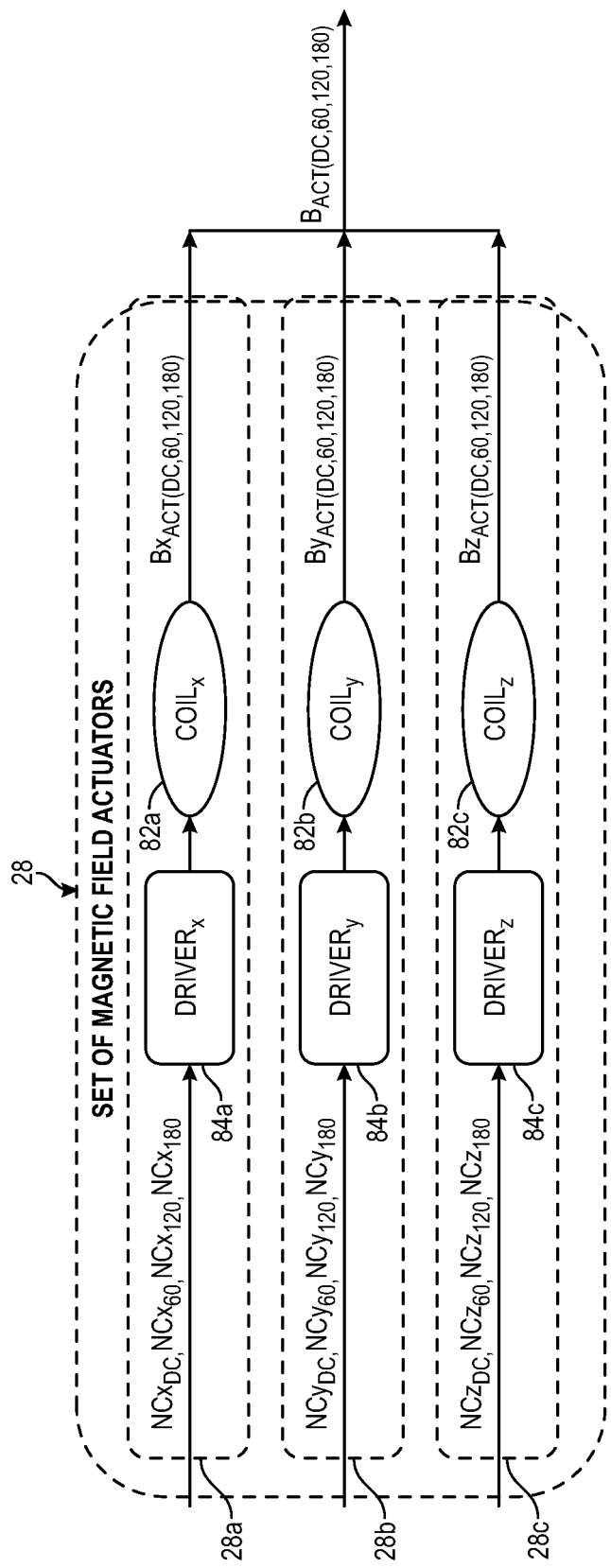
FIG. 9 is a block diagram of an exemplary set of magnetic field actuators used in the signal acquisition unit of FIG. 7.

Referring to FIG. 9, the set of magnetic field actuators 28 comprises three uniform magnetic field actuators 28a-28c, such that $0^{th}$ spatial order cancellation of the outside magnetic field $B_{OUT}$ in the x, y, and z directions can be achieved. The three uniform magnetic field actuators 28a-28c respectively comprise Helmholtz coils 82a-82c ($coil_x$, $coil_y$, $coil_z$) that are orthogonally arranged relative to each other to generate actuated magnetic fields $Bx_{ACT(DC,60,120,180)}$, $By_{ACT(DC,60,120,180)}$, and $Bz_{ACT(DC,60,120,180)}$ at DC, 60 Hz, 120 Hz, and 180 Hz respectively in the x, y, and z directions, which combine to create the actuated magnetic field $B_{ACT(DC,60,120,180)}$ illustrated in FIG. 7. The three uniform magnetic field actuators 28a-28c further respectively comprise associated drivers 84a-84c ($driver_x$, $driver_y$, $driver_z$) configured for delivering electrical currents at a defined amplitude (e.g., amperage, voltage, or some other variable) and frequency to the respective coils 82a-82c in response to noise-cancelling signals $NCx_{DC}$, $NCx_{60}$, $NCx_{120}$, and $NCx_{180}$, $NCy_{DC}$, $NCy_{60}$, $NCy_{120}$, and $NCy_{180}$, and $NCz_{DC}$, $NCz_{60}$, $NCz_{120}$, and $NCz_{180}$ output by the processor 30 of FIG. 7 (generically represented as $NC_{DC}$, $NC_{60}$, $NC_{120}$, and $NC_{180}$, thereby setting the actuation strengths of the magnetic field actuators 28a-28c. Optionally, the set of magnetic field actuators 28 may additionally comprise six (or any suitable number, such as five or nine) gradient magnetic field actuators and associated drivers (not shown), such that the $1^{st}$ spatial order cancellation of the outside magnetic field $B_{OUT}$ in the x, y, and z directions can also be achieved.

Referring back to FIG. 7, the processor 30 further comprises a set of four coarse filters 86 ((including a DC filter 86a (filter 1) and harmonic filters 86b-86d (filters 2-4)); a set of four fine filters 88 ((including a DC filter 88a (filter 1) and harmonic filters 88b-88d (filters 2-4)); a set of four estimators 90 (including a DC estimator 90a (estimator 1) and harmonic estimators 90b-90d (estimators 2-4)); a set of four controllers 92 (including a DC controller 92a (controller 1) and harmonic controllers 92b-92d (controllers 2-4); and three oscillators 94 (including harmonic oscillators 94a-94c) (oscillators 1-3)), and a feedback control loop manager 96. In the illustrated embodiment, these components, along with the modulator/demodulator 74, are digitally performed (e.g., in an FPGA), in which case, digital-to-analog converters (DAC) or analog-to-digital converters (ADC) (not shown) can be employed between the processor 30 and the external components, namely, the flux gate magnetometers 26a, SERF OPMs 26b, and magnetic field actuators 28.

For purposes of brevity in illustration and description, the processor 30 is described as processing the coarse error signals $SC_{ERR}$ and the fine error signals $SF_{ERR}$ respectively output from the coarse magnetometers 26a and fine magnetometers 26b in a scalar or one-dimensional manner. However, as described above, each of the magnetometers 26 is preferably capable of detecting the total residual magnetic field $B_{TOT}$ in three dimensions (x, y, and z), and thus, each of the coarse error signals $SC_{ERR}$ and the coarse error signals $SC_{ERR}$ output by each coarse magnetometer 26a or each fine magnetometer 26b is a directional vector. In this case, the elements of the processor 30 (i.e., the set of coarse filters 86, set of fine filters 88, set of estimators 90, set of controllers 92, oscillators 94, and a feedback control loop manager 96 will be duplicated for each of the three dimensions.

The coarse filters 86a-86d are respectively employed by the coarse feedback control loops 60a-60d, while the fine filters 88a-88d are respectively employed by the fine feedback control loops 62a-62d. The coarse filters 86a-86d are configured for extracting and outputting characteristics of the dominant DC, 60 Hz, 120 Hz, and 180 Hz frequency components of the coarse error signals $SC_{ERR}$ output by the flux gate magnetometers 26a, while the fine filters 86a-86d are configured for extracting and outputting characteristics of the dominant DC, 60 Hz, 120 Hz, and 180 Hz frequency components of the fine error signals $SF_{ERR}$ output by the SERF OPMs 26b.

Figure 10:
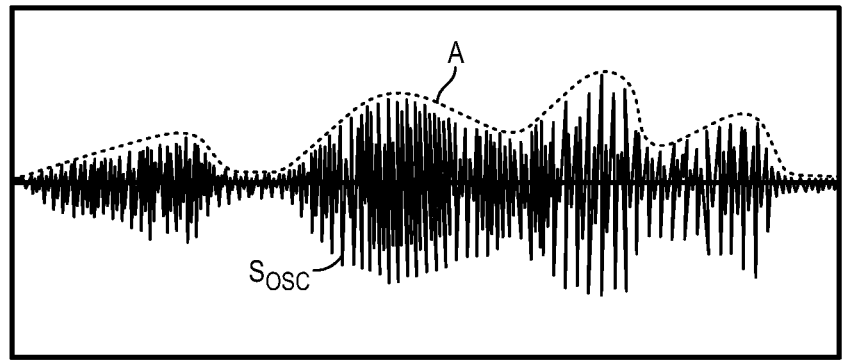
FIG. 10 is a diagram of an exemplary 180 Hz oscillatory signal in a total residual magnetic field detected by the signal acquisition unit of FIG. 7.

As discussed above with respect to FIG. 6, it is preferred that the signal processor unit 18c extract the slowly varying envelope amplitudes and phases of the dominant 60 Hz, 120 Hz, and 180 Hz frequency components, instead of the underlying raw oscillatory components, from each of the coarse error signals $SC_{ERR}$ and fine error signals $SF_{ERR}$, since the flux gate magnetometers 26a and SERF OPMs 26b have limited bandwidths. For example, as illustrated in FIG. 10, although the underlying raw 180 Hz oscillation $S_{OSC}$ of an exemplary signal may vary quickly, the envelope A and phase of the underlying 180 Hz oscillation $S_{OSC}$ may change much more slowly.

In one embodiment, the coarse harmonic filters 86b-86d and fine harmonic filters 88b-88d perform quadrature detection respectively on each of the coarse error signals $SC_{ERR}$ and fine error signals $SF_{ERR}$ to extract the envelope amplitudes and phases of the respective dominant 60 Hz, 120 Hz, and 180 Hz frequency components of each of the coarse error signals $SC_{ERR}$ and fine error signals $SF_{ERR}$. The extracted envelope amplitude and phase of each of the coarse error signals $SC_{ERR}$ and fine error $SF_{ERR}$ may be represented as the signal $y(t)=A(t)*\cos(\omega t+\varphi(t))$, where $\omega$ equals the frequency of the oscillation of interest of the signal (in this case, either 60 Hz, 120 Hz, or 180 Hz), t is time, and A and $\varphi$ are the magnitude and phase of the signal y, respectively. Equivalently, $y(t)=A(t)*\cos(\omega t+\varphi(t))$ may be expressed as $y(t)=a(t)*\cos(\omega t)+b(t)*\cos(\omega t)$.

A quadrature detection may extract the coefficients a and b as a function of time from the cosine and sinusoid terms of the quadrature signal y. One skilled in the art of signal processing would understand that the information contained in the amplitude and phase (A, $\varphi$) and contained in the two coefficients (a, b) is the same information, and is interrelated by trigonometric formulas. Thus, instead of outputting signals as quickly varying raw oscillations y(t) of a coarse error signals $SC_{ERR}$ or a fine error signals $SF_{ERR}$ at 60 Hz, 120 Hz, and 180 Hz, the coarse filters 86b-86d and the fine filters 88b-88d respectively output signals as the slowly varying a(t) and b(t) (or equivalently A(t) and $\varphi$ (t)) of the coarse error signals $SC_{ERR}$ and fine error signals $SF_{ERR}$ at 60 Hz, 120 Hz, and 180 Hz.

In the illustrated embodiment, the characteristics of each of the coarse error signals $SC_{ERR}$ extracted and output by the coarse filters 86a-86d and the characteristics of each of the fine error signals $SF_{ERR}$ extracted and output by the fine filters 88a-88d are preferably the DC amplitude and the sine and cosine coefficients $(a, b)_{60}$, $(a, b)_{120}$, and $(a, b)_{180}$ corresponding to the slowly varying a(t) and b(t) coefficients in the quadrature signal $y(t)=a(t)*\cos(\omega t)+b(t)*\cos(\omega t)$. Alternatively, the harmonic coarse filters 86b-86d may equivalently output the envelope amplitude and phase (A, $\omega)_{60}$, $(A, \varphi)_{120}$, and $(A, \varphi)_{180}$ corresponding to the slowly varying envelope amplitude A(t) and phases $\varphi(t)$ in the equivalent quadrature signal $y(t)=A(t)*\cos(\omega t+\varphi(t))$.

The DC coarse filter 86a or the DC fine filter 88a may take the form of a low-pass filter for extracting the DC component from each of the coarse error signals $SC_{ERR}$, while the harmonic coarse filters 86b-86d and harmonic fine filters 88b-88d may take the form of lock-in amplifiers respectively referenced to 60 Hz, 120 Hz, and 180 Hz for extracting the envelope amplitudes and phases from the respective dominant 60 Hz, 120 Hz, and 180 Hz frequency components of each of the coarse error signals $SC_{ERR}$ and each of the fine error signals $SF_{ERR}$.

In a preferred embodiment, it may be desirable to estimate the dominant DC, 60 Hz, 120 Hz, and 180 Hz frequency components in the total residual magnetic field $B_{TOT}$ at the respective SERF OPMs 26b (some of which may not be in their operating range), and provide this estimated information to the controllers 90a-90d instead of providing the actual measurements at the flux gate magnetometers 26a (i.e., directly from the coarse errors $SC_{ERR}$). This is done so that the outside magnetic field $B_{OUT}$ at the respective SERF OPMs 26b may be more accurately cancelled to minimize the total residual magnetic field $B_{TOT}$ at the respective SERF OPMs 26b even in the presence of bandwidth limitations on the magnetometers 26 and actuators 28. Furthermore, even if some of the SERF OPMs 26b are in their operating range, the fine error signals $SF_{ERR}$ output by each of these SERF OPMs 26b may be corrected or refined by estimating the dominant DC, 60 Hz, 120 Hz, and 180 Hz frequency components in the total residual magnetic field $B_{TOT}$ at the respective SERF OPMs (in effect, estimating the fine error signals $SF_{ERR}$ that should be output by each of these SERF OPMs 26b) based on the actual coarse error signals $SC_{ERR}$ and actual fine error signals $SF_{ERR}$ output by the flux gate magnetometers 26a and SERF OPMs 26b that are in-range.

Thus, the coarse feedback control loops 60a-60d and fine feedback control loops 62a-62d both preferably employ the set of estimators 90a-90d. The estimators 90a-90d are configured for respectively estimating the dominant DC, 60 Hz, 120 Hz, and 180 Hz frequency components of the spatial components in the total residual magnetic field $B_{TOT}$ respectively at the respective SERF OPMs 26b based on the characteristics (namely, the DC amplitude and sine and cosine coefficients $(a, b)_{60}$, $(a, b)_{120}$, and $(a, b)_{180}$ of the respective dominant DC, 60 Hz, 120 Hz, and 180 Hz frequency components) extracted by the coarse harmonic filters 86a-86d and fine harmonic filters 88a-88d from the coarse error signals $SC_{ERR}$ and fine error signals $SF_{ERR}$, and outputting the estimated characteristics (in this case, the estimated DC' amplitude and sine and cosine coefficients (a, b)'$_{60}$, (a, b)'$_{120}$, and (a, b)'$_{180}$) of the spatial components of the total residual magnetic field $B_{TOT}$ at the SERF OPMs 26b (in effect, estimating the fine error signals $SF_{ERR}$ that should be output by the respective out-of-range SERF OPMs 26b). The spatial components of the total residual magnetic field $B_{TOT}$ at the SERF OPMs 26b (i.e., the estimated DC' amplitude and sine and cosine coefficients (a, b)'$_{60}$, (a, b)'$_{120}$, and (a, b)'$_{180}$ output by the estimators 90a-90d) may be treated as an error signal to be controlled (to be brought to zero or to near-zero).

The estimators 90a-90d may infer the dominant DC, 60 Hz, 120 Hz, and 180 Hz frequency components of the spatial components in the total residual magnetic field $B_{TOT}$ respectively at the out-of-range SERF OPMs 26b from available measurements taken by the flux gate magnetometers 26a and available in-range SERF OPMs 26b (i.e., all available estimated DC amplitude and sine and cosine coefficients (a, b)'$_{60}$, (a, b)'$_{120}$, and (a, b)'$_{180}$ of the respective dominant DC, 60 Hz, 120 Hz, and 180 Hz frequency components extracted by the coarse harmonic filters 86a-86d and fine harmonic filters 88a-88d) using any suitable technique, such as, e.g., least squares, weighted least squares, system identification, optimization, or other methods such as neural networks, genetic algorithms, fuzzy logic, or machine learning, or other similar methods.

The set of estimators 90a-90d may estimate the dominant DC, 60 Hz, 120 Hz, and 180 Hz frequency components of the spatial components in the total residual magnetic field $B_{TOT}$ respectively at the out-of-range SERF OPMs 26b using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System".

The information output by the estimators 90a-90d (namely, the estimated DC' amplitude and sine and cosine coefficients (a, b)'$_{60}$, (a, b)'$_{120}$, and (a, b)'$_{180}$) may be provided to the set of controllers 92a-92d in parallel or may be filtered (e.g., computing the selecting the worst-case (highest) error signal or performing a statistical analysis (e.g., mean, standard deviation, moments), etc.) prior to being provided to the controllers 92a-92d.

In an alternative embodiment, the estimated sine and cosine coefficients (a, b)'$_{60}$, (a, b)'$_{120}$, and (a, b)'$_{180}$ of the respective dominant 60 Hz, 120 Hz, and 180 Hz frequency components of each of the coarse error signals $SC_{ERR}$ and fine error signals $SF_{ERR}$ may be provided to the set of controllers 92a-92d without performing the foregoing estimation function. In this case, the information extracted from the coarse error signals $SC_{ERR}$ and fine error signals $SF_{ERR}$ (in this case, the estimated sine and cosine coefficients (a, b)'$_{60}$, (a, b)'$_{120}$, and (a, b)'$_{180}$ of the respective dominant 60 Hz, 120 Hz, and 180 Hz frequency components) can be provided directly to the controllers 92a-92d.

The coarse feedback control loops 60a-60d and fine feedback control loops 62a-62d both employ the set of controllers 92a-92d. Based on the estimated characteristics (in this case, the estimated DC' amplitude and sine and cosine coefficients (a, b)'$_{60}$, (a, b)'$_{120}$, and (a, b)'$_{180}$) of the spatial components of the total residual magnetic field $B_{TOT}$ at the SERF OPMs 26b, the controllers 92a-92d are configured for determining amplitude levels and phases of the actuated magnetic field $B_{ACT}$ generated by the set of magnetic field actuators 28 that will minimize the dominant DC, 60 Hz, 120 Hz, and 180 Hz frequency components in the total residual magnetic field $B_{TOT}$ at the respective SERF OPMs. In effect, this minimizes the fine error signals $SF_{ERR}$ estimated at the out-of-range SERF OPMs 26b. The controllers 92a-92 are further configured for respectively outputting corresponding noise-cancelling control signals in the form of a DC" amplitude and sine and cosine coefficients (a"$_{60}$, b"$_{60}$, (a"$_{120}$, b"$_{120}$), and (a"$_{180}$, b"$_{180}$) at the appropriate harmonic, amplitude level, and phase, which can be subsequently applied as coefficients to a cosine signal and sinusoid signal, as will be described in further detail below.

Each of the controllers 92a-92d may take the form of a proportional integral derivative (PID) controller that generates the control signals DC", (a"$_{60}$, b"$_{60}$), (a"$_{120}$, b"$_{120}$), and (a"$_{180}$, b"$_{180}$) based on proportional, integral, and derivative terms. In this manner, past, present, and future estimated behaviors are taken into account to provide more accurate and stable control. Alternatively, the controllers 92a-92d may be a constant gain, proportional integral (PI), linear quadratic regulator (LQR), H2, H-infinity, or other linear and nonlinear controllers known to those of skill in the art of control systems.

In one advantageous embodiment, the controllers 92a-92d respectively integrate the estimated characteristics of the spatial components of the total residual magnetic field $B_{TOT}$ (in this case, the estimated DC' amplitude and sine and cosine coefficients (a, b)'$_{60}$, (a, b)'$_{120}$, and (a, b)'$_{180}$) at the SERF OPMs 26b (which serves as the error signal) over time to form integral error terms in accordance with $E(t)=\int e(\tau)d\tau$. Alternatively, a separate processing component can perform this integration function and provide the resulting integral error to the controllers 92a-92d. Both methods enable improved magnetic field cancellation, for the following reason. To ensure that the steady state error is low, or to effectively cancel slowly varying components of the outside magnetic field $B_{OUT}$, for proportional control (where the applied control signal is proportional to the error signal), it can be desirable to use high gain control to achieve cancellation of the outside magnetic field $B_{OUT}$. However, there is a limit to how high the gain can be set before undesirable effects, such as instability and actuator saturation, may occur. If the spatial components of the total residual magnetic field $B_{TOT}$ at the SERF OPMs 26b are not zero, and is instead some persistent positive or negative value at DC, 60 Hz, 120 Hz, or 180 Hz, then the integral error terms will grow over time. Thus, by providing the integral error terms to the controllers 92a-92d, or having the controllers 92a-92d carry out a time integral, in either case will be able to react to any persistent errors, without a need for high gain (which may be not feasible for other reasons such as instability or actuator saturation). The end result is that the spatial components of the total residual magnetic field $B_{TOT}$ at the SERF OPMs 26b will be driven to near-zero (because if it is not then any persistent error will continue to be integrated over time until the controllers 92a-92d do drive it to near-zero).

The coarse feedback control loops 60a-60d and fine feedback control loops 62a-62d both employ the set of oscillators 94a-94c. The control signal DC" output by the DC controller 92a, itself serves as a noise-cancelling drive signal $NC_{DC}$, whereas the oscillators 94a-94c are configured for generating noise-cancelling drive signals $NC_{60}$, $NC_{120}$, and $NC_{180}$ respectively having frequencies of 60 Hz, 120 Hz, and 180 Hz and at amplitudes contained in the respective noise-cancelling control signals (a"$_{60}$, b"$_{60}$), (a"$_{120}$, b"$_{120}$), and (a"$_{180}$, b"$_{180}$)

The noise-cancelling drive signals $NC_{60}$, $NC_{120}$, and $NC_{180}$ are fast oscillations at 60 Hz, 120 Hz, and 180 Hz that are multiplied by the slow noise-cancelling control signals (a"$_{60}$, b"$_{60}$), (a"$_{120}$, b"$_{120}$), and (a"$_{180}$, b"$_{180}$) output by the respective controllers 92b-92d, and thus, may take the form of $u(t)=a"(t)*\cos(\omega t)+b"(t)*\sin(\omega t)$, where a"(t) and b"(t) are the slow terms computed by the controllers 92b-92d and $\cos(\omega t)$ and $\sin(\omega t)$ are the fast terms generated by the oscillators 94a-94c. Alternatively, if the envelope and phase extracted from the coarse error signals $SC_{ERR}$ and each of the fine error signals $SF_{ERR}$ are expressed as amplitude and phase values $(A, \varphi)_{60}$, $(A, \varphi)_{120}$, and $(A, \varphi)_{180}$, noise-cancelling drive signals $NC_{60}$, $NC_{120}$, and $NC_{180}$ may take the form of $u(t)=A(t)*\cos(\omega t+\varphi(t))$, where $A(t)$ and $\varphi(t)$ are the slow terms computed by the controllers 92b-92d, and $\cos(\omega t)$ is the fast term generated by the oscillators 38a-38c.

Thus, it can be appreciated that each of the harmonic coarse feedback control loops 60b-60d and fine feedback control loops 60b-60d controls fast oscillatory signals by first extracting the slow varying terms (i.e., slowly varying sine and cosine coefficients a(t) and b(t) or equivalently the slowly varying amplitude A(t) and phase $\varphi(t)$) from the coarse error signal $SC_{ERR}$ or fine error signal $SF_{ERR}$ at 60 Hz, 120 Hz, and 180 Hz, estimating the slowly varying sine and cosine coefficients a(t) and b(t)) or equivalently the slowly varying amplitude A(t) and phase $\varphi(t)$ of the spatial components of the total residual magnetic field $B_{TOT}$ at the SERF OPMs 26b, generating slow control signals noise-cancelling control signals (i.e., the slowly varying amplitude a(t) and b(t) or two slowly varying amplitudes A(t) and $\varphi(t)$), and converting the slowly varying control signals into quickly varying noise-cancelling drive signals $NC_{60}$, $NC_{120}$, and $NC_{180}$ (i.e., u(t)).

The advantage of this exemplary "fast to slow and back to fast" control on the envelope and phase of an oscillatory signal (or on the slow coefficients of sine and cosine) is the ability to control fast signals with limited resources. Specifically, the fast-to-slow step performed by the harmonic coarse filters 86b-86d and harmonic fine filters 88b-88d to generate the slowly varying sine and cosine coefficients a(t) and b(t) or the slowly varying amplitude A(t) and phase $\varphi(t)$ may be accomplished cheaply and quickly with available compact electronics. Likewise, the slow-to-fast step performed by the oscillators 94a-94c to generate the quickly varying noise-cancelling drive signals $NC_{60}$, $NC_{120}$, and $NC_{180}$ can also be done cheaply and quickly with compact electronics. This technique allows the controllers 92b-92d to operate with slow signals, and the harmonic coarse feedback control loops 60b-60d and fine feedback control loops 60b-60d to operate at a lower bandwidth and with higher latencies. Control feedback control loops that operate substantially faster than the speed of the oscillations are therefore not necessary. The end result is effective control even of fast signals with sensors, actuators, and electronics that are small, cheap, light, and low power enough to be integrated into a wearable system.

The coarse feedback control loops 60a-60d and fine feedback control loops 62a-62d both employ the set of magnetic field actuators 28. In response to the noise-cancelling signals $NC_{DC}$, $NC_{60}$, $NC_{120}$, and $NC_{180}$, as well as the oscillatory signal $MOD_{2K}$ from the modulator/demodulator oscillator 66, the set of magnetic field actuators 28 is configured for generating the modulated actuated magnetic field $B_{ACT(DC,60,120,180))}$ at DC, 60 Hz, 120 Hz, and 180 Hz, such that the dominant DC, 60 Hz, 120 Hz, and 180 Hz frequency components of the outside magnetic field $B_{OUT}$ are at least partially cancelled at the SERF OPMs 26b.

It should be appreciated that the processor 30 will actually output a set of noise-cancelling drive signal $NC_{DC}$, $NC_{60}$, $NC_{120}$, and $NC_{180}$ to the set of magnetic field actuators 28 for each directional component, and thus, will output noise-cancelling signals $NCx_{DC}$, $NCx_{60}$, $NCx_{120}$, and $NCx_{180}$, $NCy_{DC}$, $NCy_{60}$, $NCy_{120}$, and $NCy_{180}$, and $NCz_{DC}$, $NCz_{60}$, $NCz_{120}$, and $NCz_{180}$ to the set of magnetic field actuators 28a-28c, as illustrated in FIG. 9, such that the set of magnetic field actuators 28a-28c generate and output actuated magnetic fields $Bx_{ACT(DC,60,120,180))}$, $By_{ACT(DC,60,120,180)}$, and $Bz_{ACT(DC,60,120,180)}$ at DC, 60 Hz, 120 Hz, and 180 Hz respectively in the x, y, and z directions, which combine to create the actuated magnetic field $B_{ACT(DC,60,120,180)}$ illustrated in FIG. 7.

The feedback control loop manager 96 is responsible for implementing the management control loop 64 discussed above with respect to FIG. 6; i.e., managing how the coarse feedback control loops 60b-60d and the fine feedback control loops 60b-60d are employed (e.g., how the coarse error signals $SC_{ERR}$ output by the flux gate magnetometers 26a and the fine error signals $SF_{ERR}$ output by the SERF OPMs 26b are to be used) for optimal cancellation of the outside magnetic field $B_{OUT}$, and thus optimal suppression of the total residual magnetic field $B_{TOT}$, and corrects additional factors that can change more slowly over time, such as, e.g., calibrating flux gate offset and gain drift, adapting to changing time delays in computations, etc.).

In one embodiment, the feedback control loop manager 96 performs the "sensor hand-off" procedure between the flux gate magnetometers 26a and SERF OPMs 26b, such that passage of the coarse error signals $SC_{ERR}$ output by the flux gate magnetometers 26a to the coarse filters 86a-86d can be switched on or off, and passage of the fine error signals $SF_{ERR}$ output by the SERF OPMs 26b to the fine filters 88a-88d can be individually switched on or off. In alternative embodiments, switching logic or a state machine may be uses to perform the "sensor hand-off" procedure.

In one embodiment, the flux gate magnetometers 26a and SERF OPMs 26b can be collectively turned on or off. For example, if one (or a predetermined number) of the SERF OPMs 26b are out-of-range, the feedback control loop manager 96 may prevent passage of all of the fine error signals $SF_{ERR}$ from the SERF OPMs 26b to the fine filters 88a-88d, and allow passage of all of the coarse error signals $SC_{ERR}$ from the flux gate magnetometers 26a to the coarse filters 86a-86d, in which case, the set of coarse feedback control loops 60a-60d will be fully enabled to perform coarse cancellation on the outside magnetic field $B_{OUT}$, and the set of fine feedback control loops 62a-62a will be fully disabled. If all of the SERF OPMs 26b are in-range, the feedback control loop manager 96 may allow passage of all of the fine error signals $SF_{ERR}$ from the SERF OPMs 26b to the fine filters 88a-88d, and prevent passage of all of the coarse error signals $SC_{ERR}$ from the flux gate magnetometers 26a to the coarse filters 86a-86d, in which case, the set of fine feedback control loops 62a-62d will be fully enabled to perform fine cancellation on the outside magnetic field $B_{OUT}$, and the set of coarse control loops 60a-60d will be fully disabled.

In another embodiment, the flux gate magnetometers 26a and SERF OPMs 26b can be individually turned on or off. For example, if one of SERF OPMs 26b is in-range, the feedback control loop manager 96 may allow passage of the fine error signal $SF_{ERR}$ from this in-range SERF OPM 26b to the fine filters 88a-88d, and prevent passage of the coarse error signal $SC_{ERR}$ from a flux gate magnetometers 26a in proximity to the in-range SERF OPM 26b to the coarse filters 86a-86d, and if one of the SERF OPMs 26b is out-of-range, the feedback control loop manager 96 may prevent passage of the fine error signal $SF_{ERR}$ output by this out-of-range SERF OPM 26b to the fine filters 88a-88d, and allow passage of the coarse error signal $SC_{ERR}$ from a flux gate magnetometer 26a in proximity to the out-of-range SERF OPM 26b to the coarse filters 86a-86d. In this case, the coarse feedback control loops 60a-60d and fine feedback control loops 62a-62d will be at least partially disabled to perform cancellation on the outside magnetic field $B_{OUT}$ in a range between fine cancellation and coarse cancellation.

It is contemplated that, for example, in an everyday environment (office, home, etc.), all SERF OPMs 26b will initially be out-of-range, in which case, the coarse feedback control loops 60a-60d will be full enabled to perform coarse cancellation on the outside magnetic field $B_{OUT}$, while the fine feedback control loops 62a-62d will be fully disabled. As SERF OPMs 26b come in-range, the extent to which the fine feedback control loops 62a-62d are enabled will increase, and the extent to which the coarse feedback control loops 60a-60d are disabled will increase, until the fine feedback control loops 62a-62d are fully enabled to perform fine cancellation on the outside magnetic field $B_{OUT}$, while the coarse feedback control loops 60a-60d will be fully disabled. Thereafter, some of the previously operational SERF OPMs 26b may go out-of-range (e.g., due to a sudden change in the outside magnetic field $B_{OUT}$), thereby decreasing the extent to which the fine feedback control loops 62a-62d are enabled, in which case, the extent to which the coarse feedback control loops 62a-62d is enabled may be increased. After compensating for such a change in the outside magnetic field $B_{OUT}$, the previously unavailable SERF OPMs 26b will come in-range, and as such, the fine feedback control loops 62a-62d will again be fully enabled to perform fine cancellation on the outside magnetic field $B_{OUT}$, while the coarse feedback control loops 60a-60d will again be fully disabled.

As discussed above with respect to the signal acquisition unit 18a illustrated in FIG. 4, instead of performing a "sensor hand-off" procedure, per se, the processor 30 may weight the SERF OPMs 26b on a continuous spectrum by assigning a weight α the SERF OPMs 26b. In this case, the processor 30 may optionally comprise variable weighting filters (not shown) The weighting filters individually weight the fine error signals $SF_{ERR}$ respectively output from the SERF OPMs 26b (e.g., between 0% and 100%) and output weighted fine error signals $SF'_{ERR}$ to the estimator 90a-90d.

As also discussed above with respect to the signal acquisition unit 18a illustrated in FIG. 4, the processor 30 may monitor different operating parameters of a magnetometer 26a to determine whether the fine magnetometer 26b, in a linear operating range, in a non-linear operating range, or is saturated (non-operational). In one embodiment, the feedback control loop manager 96 monitors the modulated signal $S_{MOD}$ output by the optical detector 56 of each SERF OPM 26b to whether the SERF OPM 26b is in a linear operating range, is in an unsaturated non-linear operating range, or is saturated, and assign a value to a weighting variable α (illustrated in FIG. 11) associated with each SERF OPM 26b based on this determination, such that the weighting filters may weight the fine error signals $SF_{ERR}$ respectively output from the SERF OPMs 26b in accordance with the values assigned to the weighting variables a associated with the SERF OPMs 26b.

For example, if the SERF OPM 26b is found to be in the linear operating range, the feedback control loop manager 96 may assign a value of 1 (full weight) to the weighting variable a associated with each SERF OPM 26b. If the SERF OPM 26b is found to be saturated, the feedback control loop manager 96 may assign a value of 0 (no weight) to the weighting variable a associated with each SERF OPM 26b. If the SERF OPM 26b is found to be in an intermediate unsaturated non-linear operating range, the feedback control loop manager 96 may assign a value between 0 and 1 (partial weight) to the weighting variable a associated with each SERF OPM 26b, depending on how close the SERF OPM 26b is to being in the linear range or saturated.

Figure 11:
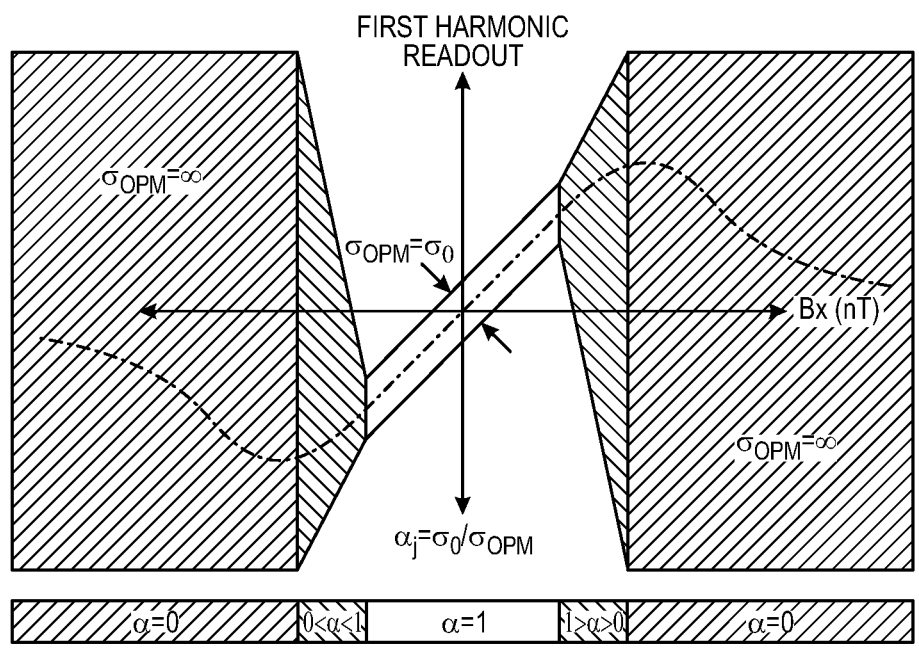
FIG. 11 is a diagram of an operating range of a SERF OPM used in the signal acquisition unit of FIG. 7.

For example, referring to FIG. 11, the first harmonic of the modulated signal $S_{MOD}$ output by a typical SERF OPM has been plotted against the magnitude of a magnetic field. The SERF OPM has an effective measurement variance $\sigma_{OPM}$ indicative of the accuracy of the SERF OPM in that the accuracy of the SERF OPM increases as the effective measurement variance $\sigma_{OPM}$ decreases, and conversely, decreases as the effective measurement variance $\sigma_{OPM}$ increases. Specifically, when the SERF OPM is subjected to a sufficiently high magnetic field (in the range α=0), that SERF OPM is saturated and provides no effective measurement of the magnetic field, and the effective SERF OPM measurement variance $\sigma_{OPM}$ is termed as infinite (infinitely large effective variance, i.e., at sufficiently high magnetic fields the SERF OPM provides no information and effectively has zero accuracy). Conversely, in the linear operating range of the SERF OPM when the magnetic field is small (α=1), then the effective measurement variance $\sigma_{OPM}$ of the SERF OPM can be defined as $\sigma_0$. In the intermediate range, when the magnetic field is high enough to drive the SERF OPM into its non-linear operating range, but the SERF OPM is not yet saturated, then the effective measurement variance $\sigma_{OPM}$ of the SERF OPM can be at a value between $\sigma_0$ and infinity.

The weighting variable $\alpha_j$ associated with a jth SERF OPM 26b can be given as the ratio $\sigma_0/\sigma_{OPM}$, such that the feedback control loop 84 assigns a value of 1 to the weighting variable a associated with the SERF OPM 26a when the effective measurement variance σOPM is at $\sigma_0$ in the linear range; and assigns a value of 0 to the weighting variable a associated with the SERF OPM 26a when the measurement variance $\sigma_{OPM}$ is effectively infinite and the SERF OPM is saturated. In the intermediate range, the disclosed scheme assigns a value of between 0 and 1 to the weighting variable a associated with the SERF OPM 26a when the effective measurement variance $\sigma_{OPM}$ is between $\sigma_0$ and infinity.

It is contemplated that, for example, in an everyday environment (office, home, etc.), all SERF OPMs 26b will initially be out-of-range, in which case, the values of the weighting variables a associated with the SERF OPMs 26b will be zero. As SERF OPMs 26b come in-range, the values of the weighting variables α associated with the SERF OPMs 26b will increase until they reach 1. Thereafter, some of the previously operational SERF OPMs 26b may go out-of-range (e.g., due to a sudden change in the outside magnetic field $B_{OUT}$), in which case, the values of the weighting variables a associated with the SERF OPMs 26b will decrease, possibly to near-zero. After compensating for such a change in the outside magnetic field $B_{OUT}$, the values of the weighting variables a associated with these SERF OPMs 26b may then increase back to 1 as the SERF OPMs 26b are brought back into their linear operating range.

Thus, it can be appreciated that the signal acquisition unit 18c takes advantage of the high dynamic range of the coarse feedback control loops 60a-60d to coarsely cancel a large portion of the outside magnetic field $B_{OUT}$, and the high sensitivity of the fine feedback control loops 62a-62d to finally cancel nearly all remaining portions of the outside magnetic field $B_{OUT}$. Furthermore, since the coarse feedback control loops 60a-60d and fine feedback control loops 62a-62d are operated at narrow bandwidths around DC, 60 HZ, 120 Hz, and 180 Hz, only noise at these narrow bandwidths and from the flux gate magnetometers 26a and SERF OPMs 26b, themselves, will be fed back into the system, which is in contrast to direct, broadband, feedback, where noise in the entire bandwidth of the feedback control loop is fed back into the system.

Figure 12:
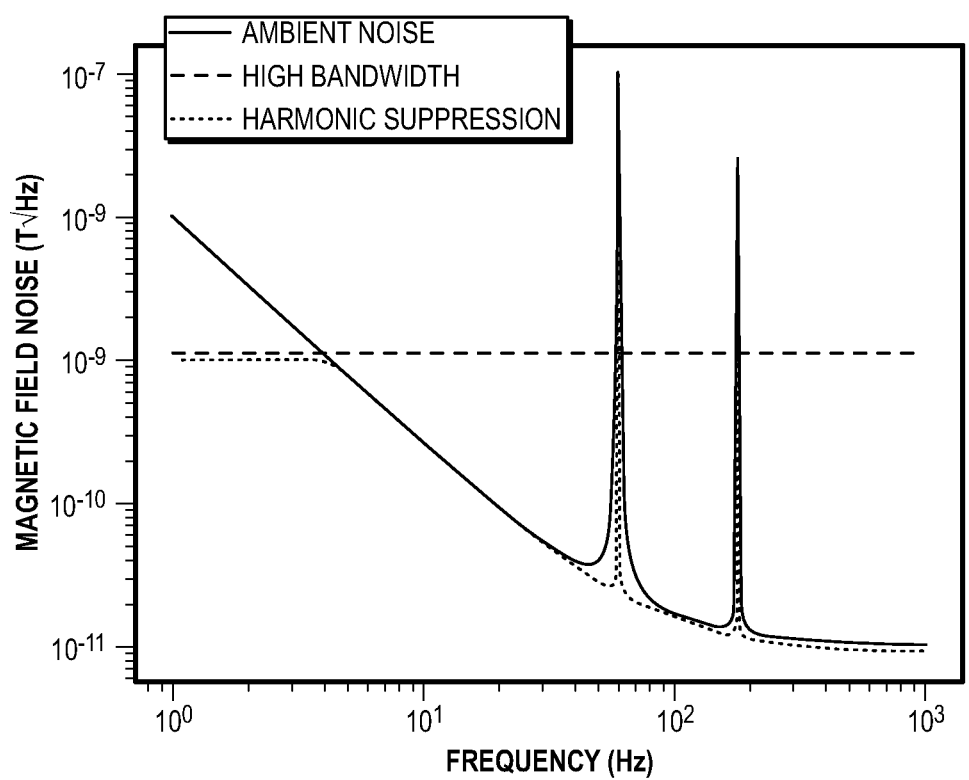
FIG. 12 is a diagram illustrating a trace representative of an outside magnetic field, including the Earth's magnetic field and 60 Hz harmonics from power sources, a trace representative of a broadband cancellation of the outside magnetic field, and harmonic magnetic field cancellation by the signal acquisition unit of FIG. 7.

For example, as shown in FIG. 12, exemplary ambient magnetic field noise is shown with a high level of low-frequency noise (caused by the Earth's magnetic field) with a gradually reducing envelope that spikes at 60 Hz and 120 Hz (caused by the harmonics of a 60 Hz power line). The intrinsic noise level of a typical low-cost flux gate magnetometer is shown to have a noise floor of about 1 nT/Hz$^{1/2}$, which is the expected noise level that a SERF OPM will experience when using direct high bandwidth feedback control loop to cancel the outside magnetic field $B_{OUT}$. An exemplary anticipated noise level that a SERF OPM will experience when using the harmonic feedback cancellation technique performed by the signal acquisition unit 18 is lower than the SERF OPM will experience when using direct high bandwidth feedback magnetic field cancellation.

Figure 13:
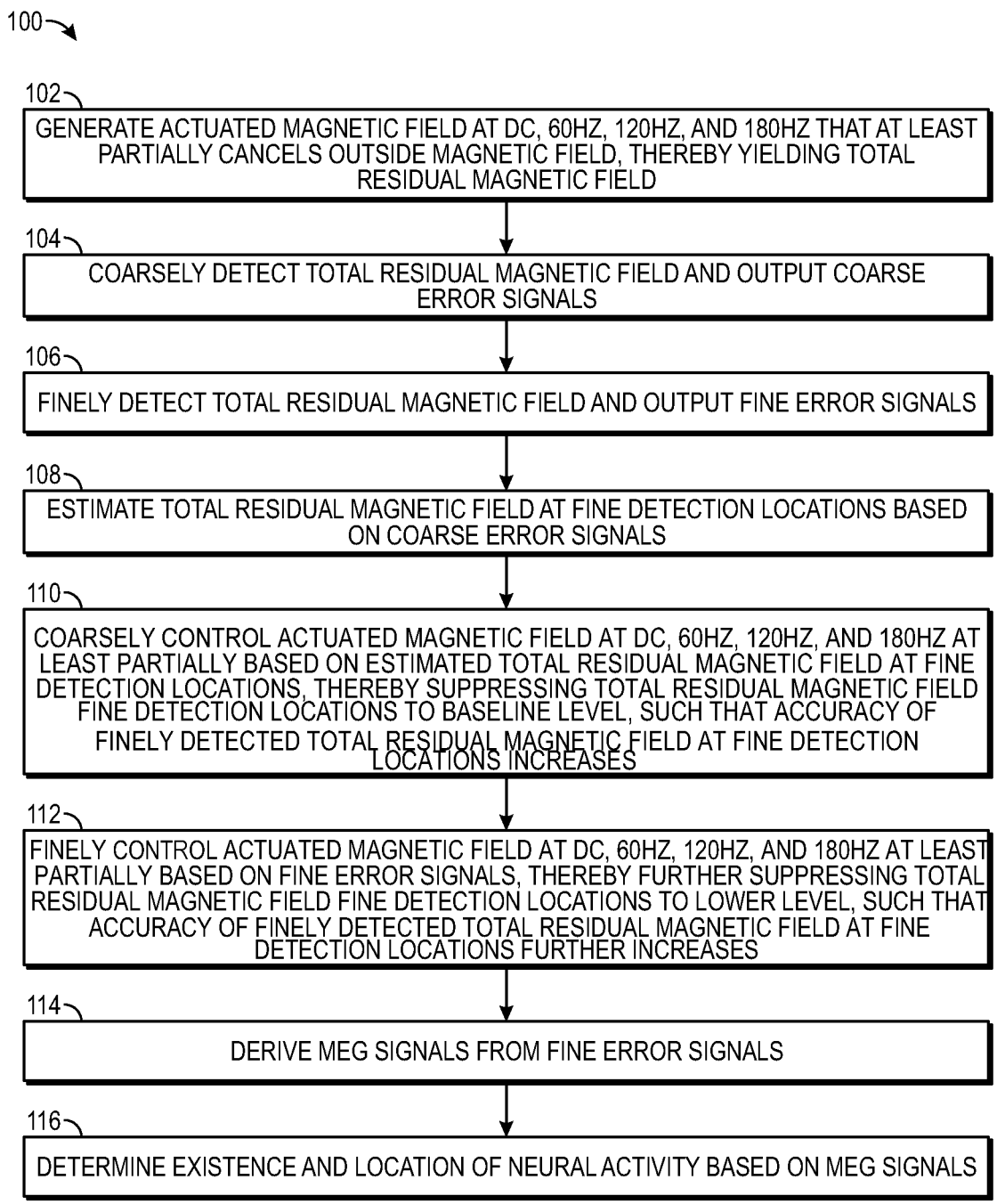
FIG. 13 is a flow diagram illustrating one exemplary method of operating the signal acquisition unit of FIG. 7.

Referring now to FIG. 13, one exemplary method 100 of identifying and localizing neural activity in the brain 14 of a user 12 will be described.

The method 100 comprises generating the actuated magnetic field $B_{ACT}$ at a plurality of distinct frequencies (e.g., DC, 60 Hz, 120 Hz, and 180 Hz) that at least partially cancels an outside magnetic field $B_{OUT}$ at the distinct frequencies (e.g., via the set of magnetic field actuators 28 of the signal acquisition unit 18c), thereby yielding a total residual magnetic field $B_{TOT}$ at the magnetometers 26 (step 102). In the preferred embodiment, the actuated magnetic field $B_{ACT}$ is generated in all three dimensions and is uniform, although in alternative embodiments, the actuated magnetic field $B_{ACT}$ may be generated in less three dimensions and may be non-uniform (e.g., a gradient).

The method 100 further comprises coarsely detecting the total residual magnetic field $B_{TOT}$ and outputting coarse error signals $SC_{ERR}$ (e.g., via the coarse magnetometers 26a of the signal acquisition unit 18c) (step 104), and finely detecting the total residual magnetic field $B_{TOT}$ and outputting fine error signals $SF_{ERR}$ (e.g. via the fine magnetometers 26b of the signal acquisition unit 18c) (step 106).

Next, the method 100 comprises coarsely controlling the actuated magnetic field $B_{ACT}$ at DC, 60 Hz, 120 Hz, and 180 Hz at least partially based on the coarse error signals $SC_{ERR}$. In one embodiment, because the fine error signals $SF_{ERR}$ may be initially inaccurate or even non-existent (e.g., if the fine magnetometers 26b are out-of-range), the method 100 comprises coarsely controlling the actuated magnetic field $B_{ACT}$ at DC, 60 Hz, 120 Hz, and 180 Hz by estimating the total residual magnetic field $B_{TOT}$ at the locations where the total residual magnetic field $B_{TOT}$ are finely detected (e.g., at the fine magnetometers 26b) based on the coarse error signals $SC_{ERR}$ (step 108), and coarsely controlling the actuated magnetic field $B_{ACT}$ at DC, 60 Hz, 120 Hz, and 180 Hz at least partially based on the estimated total residual magnetic field $B_{TOT}$ at the fine detection locations in a manner that suppresses the total residual magnetic field $B_{TOT}$ at DC, 60 Hz, 120 Hz, and 180 Hz at the fine detection locations to a baseline level (by cancelling the outside magnetic field $B_{OUT}$, e.g., via the coarse feedback control loop 50 and sending noise-cancelling control signals $NC_{DC}$, $NC_{60}$, $NC_{120}$, and $NC_{180}$ to the set of magnetic field actuators 28 of the signal acquisition unit 18c), such that the accuracy of the finely detected total residual magnetic field $B_{TOT}$ at the fine detection locations increases (e.g., the fine magnetometers 26b of the signal acquisition unit 18c come in-range) (step 110).

The method 100 further comprising finely controlling the actuated magnetic field $B_{ACT}$ at DC, 60 Hz, 120 Hz, and 180 Hz at least partially based on the fine error signals $SF_{ERR}$ in a manner that suppresses the total residual magnetic field $B_{TOT}$ at DC, 60 Hz, 120 Hz, and 180 Hz at the fine detection locations to a lower level (by further cancelling the outside magnetic field $B_{OUT}$, e.g., via the fine feedback control loop 52 and sending noise-cancelling control signals $NC_{DC}$, $NC_{60}$, $NC_{120}$, and $NC_{180}$ to the set of magnetic field actuators 28 of the signal acquisition unit 18c), such that the accuracy of the finely detected total residual magnetic field $B_{TOT}$ at the fine detection locations further increases (e.g., the fine magnetometers 26b of the signal acquisition unit 18c are further in-range) (step 112).

The method 100 further comprises deriving a plurality MEG signals $S_{MEG}$ from the fine error signals $SF_{ERR}$ (e.g., via the signal acquisition unit 18c) (step 114). That is, because the total residual magnetic field $B_{TOT}$ contains the MEG magnetic field $B_{MEG}$ from the brain 14 of the user 12, the fine error signals $SF_{ERR}$ will likewise contain the MEG signals $S_{MEG}$, which can be extracted from the fine error signals $SF_{ERR}$. The existence and location of neural activity in the brain 14 of the user 12 may then be determined based on the MEG signals $S_{MEG}$ (e.g., via the signal processing unit 20) (step 116).

It can be appreciated from the foregoing that, in general, fine control of the actuated magnetic field $B_{ACT}$ will be activated after initiating coarse control of the actuated magnetic field $B_{ACT}$. The coarse control and fine control of the actuated magnetic field $B_{ACT}$ may be managed in any one of a variety of manners to suppress the total residual magnetic field $B_{TOT}$ at the fine detection locations to the lower level.

Figure 14:
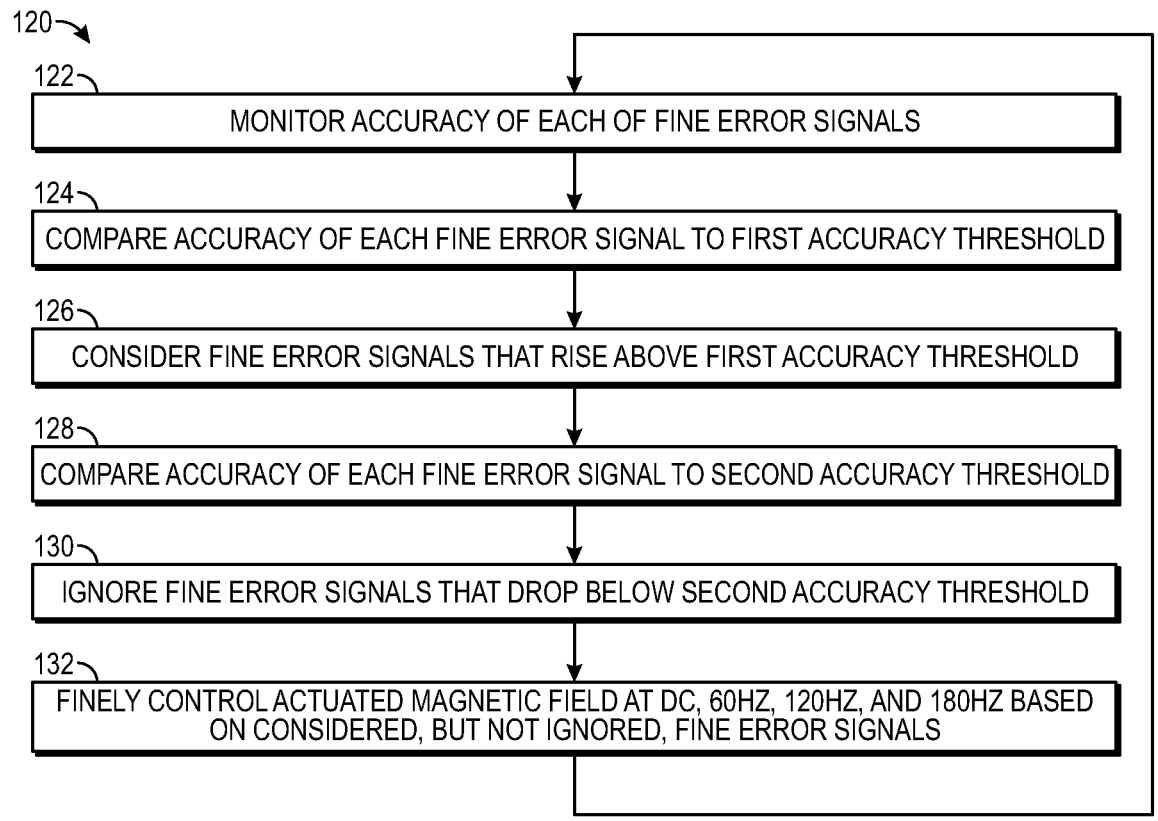
FIG. 14 is a flow diagram illustrating one exemplary method of managing the coarse and fine control of an actuated magnetic field in the method of FIG. 13.

For example, referring to FIG. 14, one exemplary method 120 for managing the control of the actuated magnetic field $B_{ACT}$ comprises determining an accuracy of each of the fine error signals $SF_{ERR}$ (step 122). The accuracy of the each of the fine error signals $SF_{ERR}$ may be monitoring, e.g., by periodically measuring the variance of the corresponding fine magnetometers 26b, as described above with respect to FIG. 11. The method 120 further comprises comparing each of the fine error signals $SF_{ERR}$ to a first accuracy threshold (step 124). If any of the fine error signals $SF_{ERR}$ have accuracies that rise above the first accuracy threshold, these fine error signals $SF_{ERR}$ will be considered (step 126). The method 120 further comprises comparing each of the fine error signals $SF_{ERR}$ to a second accuracy threshold (which may or may not be different from the first accuracy threshold) (step 128). If any of the fine error signals $SF_{ERR}$ have accuracies that drop below the second accuracy threshold, these fine error signals $SF_{ERR}$ will be ignored (step 130). The method 120 lastly comprises finely controlling the actuated magnetic field $B_{ACT}$ at DC, 60 Hz, 120 Hz, and 180 Hz based on the considered fine error signals $SF_{ERR}$, but not based on the ignored fine error signals $SF_{ERR}$ (step 132). The method 120 may then return to step 122, where the accuracies of all fine error signals $SF_{ERR}$ are again determined, compared to the first and second accuracy thresholds, and considered or ignored based on these comparisons when finely controlling the actuated magnetic field $B_{ACT}$ at DC, 60 Hz, 120 Hz, and 180 Hz.

Figure 15:
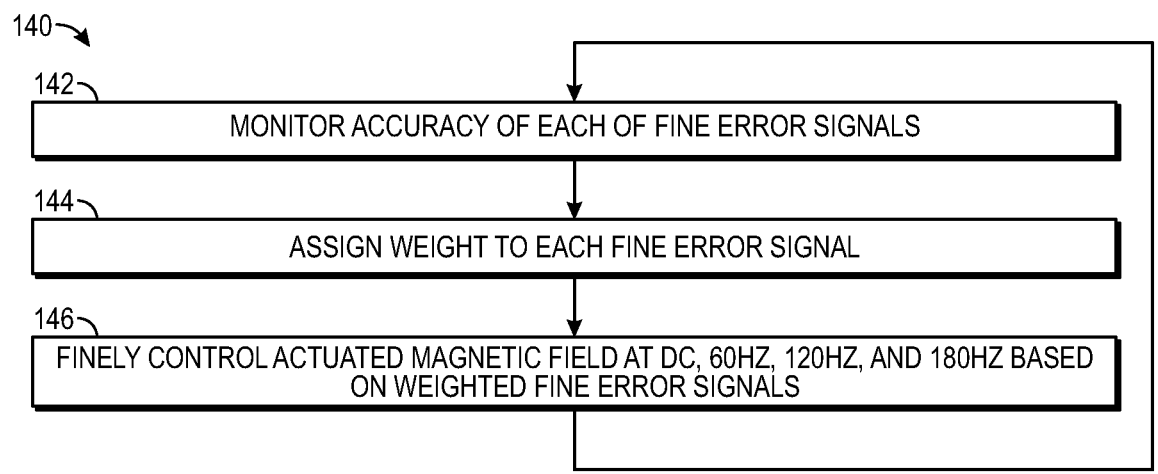
FIG. 15 is a flow diagram illustrating another exemplary method of managing the coarse and fine control of an actuated magnetic field in the method of FIGS. 13.

As another example, referring to FIG. 15, another exemplary method 140 for managing the control of the actuated magnetic field $B_{ACT}$ comprises monitoring an accuracy of each of the fine error signals $SF_{ERR}$ (step 142), and assigning a weighting (e.g., between 0 and 1) to each fine error signal $SF_{ERR}$ based on the determined accuracy of the fine error signal $SF_{ERR}$ (step 144). The accuracy of each fine error signal $SF_{ERR}$ may be determined based on whether the fine magnetometer 26b corresponding to the fine error signal $SF_{ERR}$ is in a linear operating range, in a non-linear operating range, or is saturated. The actuated magnetic field $B_{ACT}$ is then finely controlled at DC, 60 Hz, 120 Hz, and 180 Hz based on the weighted fine error signals $SF_{ERR}$ (step 146). The method 140 may then return to step 142, where the accuracies of all fine error signals $SF_{ERR}$ are again determined, the fine error signals $SF_{ERR}$ are weighted, and the actuated magnetic field $B_{ACT}$ is controlled at DC, 60 Hz, 120 Hz, and 180 Hz based on the weighted fine error signals $SF_{ERR}$.

Figure 16:
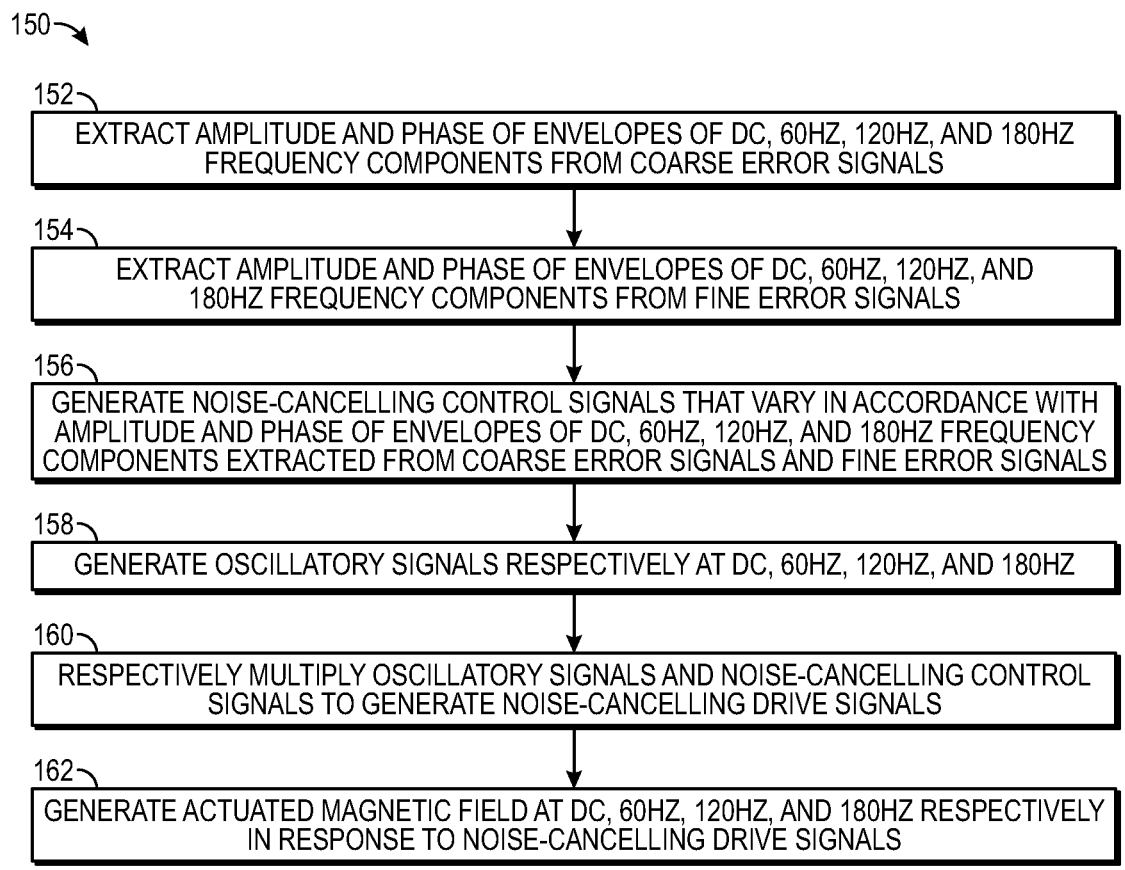
FIG. 16 is a flow diagram illustrating one exemplary method that operates on the slow-varying characteristics of error signals to control the actuated magnetic field.

Referring to FIG. 16, one exemplary method 150 operates on the slow-varying characteristics, instead of the underlying fast oscillatory signals, of the coarse error signals $SC_{ERR}$ and fine error signals $SF_{ERR}$, to control the actuated magnetic field $B_{ACT}$ at DC, 60 Hz, 120 Hz, and 180 Hz. In particular, the method 150 comprises extracting the amplitude and phase of envelopes of the DC, 60 Hz, 120 Hz, and 180 Hz frequency components from the coarse error signals $SC_{ERR}$ (step 152), and extracting the amplitude and phase of envelopes of the DC, 60 Hz, 120 Hz, and 180 Hz frequency components from the fine error signals $SF_{ERR}$ (step 154). The method 150 further comprises generating a plurality of noise-cancelling control signals that vary in accordance with the envelopes and phases of the DC, 60 Hz, 120 Hz, and 180 Hz frequency components extracted from each coarse error signal $SC_{ERR}$ and each fine error signal $SF_{ERR}$ (step 156). Any of the coarse error signals $SC_{ERR}$ and fine error signals $SF_{ERR}$ can be considered, ignored, or weighted in accordance with the methods 120 and 140 illustrated in FIGS. 14 and 15 when generating the noise-cancelling control signals. The method 150 further comprises generating oscillatory signals respectively at DC, 60 Hz, 120 Hz, and 180 Hz (step 158), and respectively multiplying the oscillatory signals and the slow-varying noise-cancelling control signals to generate a plurality of noise-cancelling drive signals (step 160). Lastly, the method 150 comprises generating the actuated magnetic field $B_{ACT}$ at DC, 60 Hz, 120 Hz, and 180 Hz respectively in response the noise-cancelling drive signals (step 162).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system, comprising:
   at least one magnetic field actuator configured for generating an actuated magnetic field that at least partially cancels an outside magnetic field, thereby yielding a total residual magnetic field;
   a plurality of coarse magnetometers respectively configured for coarsely detecting the total residual magnetic field and outputting a plurality of coarse error signals;
   a plurality of fine magnetometers respectively configured for finely detecting the total residual magnetic field and outputting a plurality of fine error signals;
   a coarse feedback control loop configured for coarsely controlling the actuated magnetic field at least partially based on at least one of the plurality of coarse error signals respectively output by at least one of the plurality of coarse magnetometers, thereby suppressing the total residual magnetic field at at least one of the plurality of fine magnetometers to a baseline level, such that the at least one of the plurality of fine magnetometers comes in-range;
   a fine feedback control loop configured for finely controlling the actuated magnetic field at least partially based on at least one of the plurality of fine error signals respectively output by the at least one of the plurality of fine magnetometers that has come in-range; and
   a management control loop configured for activating the fine feedback control loop to finely control the actuated magnetic field in a manner that further suppresses the total residual magnetic field at the at least one of the plurality of fine magnetometers that has come in-range to a lower level.

2. The system of claim 1, further comprising:
   a signal acquisition unit configured for being worn on a head of a user, the signal acquisition unit comprising a support structure, the at least one magnetic field actuator affixed to the support structure, the plurality of coarse magnetometers affixed to the support structure, and the plurality of fine magnetometers affixed to the support structure, the signal acquisition unit configured for deriving a plurality of magnetoencephalography (MEG) signals respectively from the plurality of fine error signals; and
   a signal processing unit configured for determining an existence of neural activity in the brain of the user based on the plurality of MEG signals.

3. The system of claim 2, wherein the plurality of coarse magnetometers is affixed to an outside of the support structure, and the plurality of fine magnetometers is affixed to an inside of the support structure.

4. The system of claim 1, wherein each of the plurality of coarse magnetometers is a flux gate magnetometer, and each of the plurality of fine magnetometers is an optically pumped magnetometer (OPM).

5. The system of claim 1, wherein the at least one magnetic field actuator comprises three orthogonal magnetic field actuators.

6. The system of claim 1, wherein each of the at least one magnetic field actuator comprises a uniform magnetic field actuator.

7. The system of claim 1, further comprising a processor containing the coarse feedback control loop and the fine feedback control loop.

8. The system of claim 1, wherein the coarse feedback control loop is configured for estimating the total residual magnetic field at at least one of the plurality of fine magnetometers based on the at least one coarse error signal, wherein the coarse feedback control loop is configured for coarsely controlling the actuated magnetic field at least partially based on the estimated total residual magnetic field at the at least one fine magnetometer.

9. The system of claim 1, wherein the management control loop is configured for determining whether each of the plurality of fine magnetometers is in-range or out-of-range, and finely controlling the actuated magnetic field based on the in-range or the out-of-range determination.

10. The system of claim 9, wherein finely controlling the actuated magnetic field based on the in-range or the out-of-range determination comprises considering the fine error signals output by the fine magnetometers that come in-range.

11. The system of claim 10, wherein finely controlling the actuated magnetic field based on the in-range or the out-of-range determination comprises ignoring the fine error signals output by the fine magnetometers that go out-of-range.

12. The system of claim 10, wherein each of the plurality of fine magnetometers operates in a linear range when in-range.

13. The system of claim 9, wherein finely controlling the actuated magnetic field based on the in-range or the out-of-range determination comprises determining whether the each of the plurality of fine magnetometers is in a linear operating range, in a non-linear operating range, or saturated, and assigning a weighting to the each of the plurality of fine magnetometers based on the linear operating range, the non-linear operating range, or the saturated determination.

14. A method, comprising:
generating an actuated magnetic field that at least partially cancels an outside magnetic field, thereby yielding a total residual magnetic field;
coarsely detecting the total residual magnetic field and outputting a plurality of coarse error signals;
finely detecting the total residual magnetic field and outputting a plurality of fine error signals;
coarsely controlling the actuated magnetic field at least partially based on at least one of the plurality of coarse error signals, thereby suppressing the total residual magnetic field at at least one detection location to a baseline level, such that an accuracy of at least one of the plurality of fine error signals increases; and
finely controlling the actuated magnetic field at least partially based on at least one of the plurality of fine error signals, thereby suppressing the total residual magnetic field at the at least one detection location to a lower level, such that the accuracy of the at least one fine error signal further increases.

15. The method of claim 14, further comprising:
deriving a plurality of magnetoencephalography (MEG) signals respectively from the plurality of fine error signals; and
determining an existence of neural activity in the brain of a user based on the plurality of MEG signals.

16. The method of claim 14, wherein the actuated magnetic field is generated in three dimensions.

17. The method of claim 14, wherein the actuated magnetic field is uniform.

18. The method of claim 14, further comprising estimating the total residual magnetic field at at least one detection location where the total residual magnetic field is finely detected based on the at least one coarse error signal, wherein the actuated magnetic field is coarsely controlled at least partially based on the estimated total residual magnetic field at the at least one detection location.

19. The method of claim 14, further comprising determining an accuracy of each of the plurality of fine error signals, and finely controlling the actuated magnetic field based on the accuracy determination.

20. The method of claim 19, wherein finely controlling the actuated magnetic field based on the accuracy determination comprises comparing the determined accuracies of the plurality of fine error signals to a first accuracy threshold, and considering the fine error signals having accuracies that rise above the first accuracy threshold when finely controlling the actuated magnetic field.

21. The method of claim 20, wherein finely controlling the actuated magnetic field based on the accuracy determination comprises comparing the determined accuracies of the plurality of fine error signals to a second accuracy threshold, and ignoring the fine error signals having accuracies that drop below the first accuracy threshold when finely controlling the actuated magnetic field.

22. The method of claim 20, wherein finely controlling the actuated magnetic field based on the comparison comprises assigning a weighting to the each of the plurality of fine error signals based on the comparison.

23. A system, comprising:
a signal acquisition unit configured for being worn on a head of a user, the signal acquisition unit comprising:
a support structure;
at least one magnetic field actuator affixed to the support structure, the at least one magnetic field actuator configured for generating an actuated magnetic field that at least partially cancels an outside magnetic field, thereby yielding a total residual magnetic field;
a plurality of coarse magnetometers affixed to an outside of the support structure, the plurality of coarse magnetometers respectively configured for coarsely detecting the total residual magnetic field and outputting a plurality of coarse error signals;
a plurality of fine magnetometers affixed to an inside of the support structure, the plurality of fine magnetometers respectively configured for finely detecting the total residual magnetic field and outputting a plurality of fine error signals;
a coarse feedback control loop configured for coarsely controlling the actuated magnetic field at least partially based on at least one of the plurality of coarse error signals respectively output by at least one of the plurality of coarse magnetometers;
a fine feedback control loop configured for finely controlling the actuated magnetic field at least partially based on at least one of the plurality of fine error signals respectively output by at least one of the plurality of fine magnetometers; and
a processor configured deriving a plurality of magnetoencephalography (MEG) signals respectively from the plurality of fine error signals; and
a signal processing unit configured for determining an existence of neural activity in the brain of the user based on the plurality of MEG signals.

24. A system, comprising:
at least one magnetic field actuator configured for generating an actuated magnetic field that at least partially cancels an outside magnetic field, thereby yielding a total residual magnetic field;
a plurality of coarse magnetometers respectively configured for coarsely detecting the total residual magnetic field and outputting a plurality of coarse error signals;
a plurality of fine magnetometers respectively configured for finely detecting the total residual magnetic field and outputting a plurality of fine error signals;
a management control loop configured for determining whether each of the plurality of fine magnetometers is in a linear operating range, in a non-linear operating range, or saturated, and assigning a weighting to the each of the plurality of fine magnetometers based on the linear operating range, the non-linear operating range, or the saturated determination;
a coarse feedback control loop configured for coarsely controlling the actuated magnetic field at least partially based on at least one of the plurality of coarse error signals respectively output by at least one of the plurality of coarse magnetometers; and a fine feedback control loop configured for finely controlling the actuated magnetic field at least partially based on at least one of the plurality of fine error signals respectively output by the plurality of fine magnetometers and the weighting assigned by the management control loop to the plurality of fine magnetometers.

25. A method, comprising:
generating an actuated magnetic field that at least partially cancels an outside magnetic field, thereby yielding a total residual magnetic field;
coarsely detecting the total residual magnetic field and outputting a plurality of coarse error signals;
finely detecting the total residual magnetic field and outputting a plurality of fine error signals;
estimating the total residual magnetic field at at least one detection location where the total residual magnetic field is finely detected based on at least one of the plurality of coarse error signals;
coarsely controlling the actuated magnetic field at least partially based on the estimated total residual magnetic field at the at least one detection location; and
finely controlling the actuated magnetic field at least partially based on at least one of the plurality of fine error signals.

26. A method, comprising:
generating an actuated magnetic field that at least partially cancels an outside magnetic field, thereby yielding a total residual magnetic field;
coarsely detecting the total residual magnetic field and outputting a plurality of coarse error signals;
finely detecting the total residual magnetic field and outputting a plurality of fine error signals;
coarsely controlling the actuated magnetic field at least partially based on at least one of the plurality of coarse error signals;
determining an accuracy of each of the plurality of fine error signals; and
finely controlling the actuated magnetic field at least partially based on at least one of the plurality of fine error signals and the accuracy determination.

27. The method of claim 26, wherein finely controlling the actuated magnetic field based on the accuracy determination comprises comparing the determined accuracies of the plurality of fine error signals to a first accuracy threshold, and considering the fine error signals having accuracies that rise above the first accuracy threshold when finely controlling the actuated magnetic field.

28. The method of claim 27, wherein finely controlling the actuated magnetic field based on the accuracy determination comprises comparing the determined accuracies of the plurality of fine error signals to a second accuracy threshold, and ignoring the fine error signals having accuracies that drop below the first accuracy threshold when finely controlling the actuated magnetic field.

29. The method of claim 27, wherein finely controlling the actuated magnetic field based on the comparison comprises assigning a weighting to the each of the plurality of fine error signals based on the comparison.

* * * * *